US010416162B2

(12) United States Patent
Huang et al.

(10) Patent No.: US 10,416,162 B2
(45) Date of Patent: Sep. 17, 2019

(54) HER2 DIAGNOSTIC METHODS

(75) Inventors: Weidong Huang, Pleasanton, CA (US);
Jeff Sperinde, El Granada, CA (US);
Michael Bates, San Carlos, CA (US);
Colombe Chappey, San Francisco, CA (US); John William Winslow, El Granada, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 308 days.

(21) Appl. No.: 12/340,436

(22) Filed: Dec. 19, 2008

(65) Prior Publication Data

US 2009/0191559 A1 Jul. 30, 2009

Related U.S. Application Data

(60) Provisional application No. 61/121,817, filed on Dec. 11, 2008, provisional application No. 61/121,480, filed on Dec. 10, 2008, provisional application No. 61/015,608, filed on Dec. 20, 2007.

(51) Int. Cl.
*G01N 33/574* (2006.01)

(52) U.S. Cl.
CPC ..... *G01N 33/574* (2013.01); *G01N 33/57415* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,318,846 A | 3/1982 | Khanna et al. |
| 4,650,750 A | 3/1987 | Giese |
| 4,720,455 A | 1/1988 | Babu et al. |
| 4,968,603 A | 11/1990 | Slamon et al. |
| 4,997,928 A | 3/1991 | Hobbs, Jr. |
| 5,340,716 A | 8/1994 | Ullman et al. |
| 5,360,819 A | 11/1994 | Giese |
| 5,480,968 A | 1/1996 | Kraus et al. |
| 5,516,636 A | 5/1996 | McCapra |
| 5,516,931 A | 5/1996 | Giese et al. |
| 5,536,834 A | 7/1996 | Singh et al. |
| 5,565,324 A | 10/1996 | Still et al. |
| 5,565,552 A | 10/1996 | Madga et al. |
| 5,599,681 A | 2/1997 | Epstein et al. |
| 5,602,273 A | 2/1997 | Giese et al. |
| 5,622,929 A | 4/1997 | Willner et al. |
| 5,677,171 A | 10/1997 | Hudziak et al. |
| 5,709,994 A | 1/1998 | Pease et al. |
| 5,763,602 A | 6/1998 | Li et al. |
| 5,772,997 A | 6/1998 | Hudziak et al. |
| 5,811,098 A | 9/1998 | Plowman et al. |
| 5,945,526 A | 8/1999 | Lee et al. |
| 5,968,511 A | 10/1999 | Akita et al. |
| 5,986,076 A | 11/1999 | Rothschild et al. |
| 6,001,673 A | 12/1999 | Marcinkiewicz |
| 6,096,723 A | 8/2000 | Menchen et al. |
| 6,191,278 B1 | 2/2001 | Lee et al. |
| 6,204,007 B1 | 3/2001 | Owens et al. |
| 6,251,581 B1 | 6/2001 | Ullman et al. |
| 6,322,980 B1 | 11/2001 | Singh |
| 6,346,384 B1 | 2/2002 | Pollner |
| 6,372,907 B1 | 4/2002 | Lee et al. |
| 6,514,700 B1 | 2/2003 | Singh |
| 6,627,400 B1 | 9/2003 | Singh et al. |
| 6,630,296 B2 | 10/2003 | Xue et al. |
| 6,649,351 B2 | 11/2003 | Matray et al. |
| 6,673,550 B2 | 1/2004 | Matray et al. |
| 6,682,877 B2 | 1/2004 | Singh |
| 6,682,887 B1 | 1/2004 | Singh |
| 6,686,152 B2 | 2/2004 | Singh et al. |
| 6,770,439 B2 | 8/2004 | Singh et al. |
| 6,818,399 B2 | 11/2004 | Singh et al. |
| 6,846,645 B2 | 1/2005 | Xue et al. |
| 6,916,612 B2 | 7/2005 | Singh et al. |
| 6,949,347 B2 | 9/2005 | Singh et al. |
| 6,955,874 B2 | 10/2005 | Singh et al. |
| 7,001,725 B2 | 2/2006 | Singh et al. |
| 7,037,654 B2 | 5/2006 | Chenna et al. |
| 7,041,459 B2 | 5/2006 | Singh et al. |

(Continued)

FOREIGN PATENT DOCUMENTS

| | | |
|---|---|---|
| AU | 2001279222 | 8/2001 |
| CA | 2403326 | 11/2001 |

(Continued)

OTHER PUBLICATIONS

Mukherjee (J Clin Oncology, 2005, vol. 23, No. 16S, p. 553).*
Harries et al. (Endrocrine-related cancer, 2002, vol. 9, pp. 75-85).*
Baselga (Oncology, 2001, 61 (suppl 2):14-21.*
Jahanzeb (Clinical Breast Cancer, 2003, vol. 1, pp. 28-38).*
Buzdar (J Clin Oncolgy, 2005, vol. 23, pp. 3676-3685).*
Fountzilas et al. (Annals of Oncology, 2001, vol. 12:1545-1551).*
Mukherjee et al (Proc. Amer. Assoc. Cancer Research, 2005, vol. 46, abstract #3688).*
Toi et al (Journal of Clinical Oncology, 2007, ASCO Annual Meeting proceedings part I, vol. 25, No. 18S (Jun. 20 Supplement), 2007: Abstract 1025).*
Bates et al (Journal of Clinical oncology, 2007, ASCO Annual meeting Proceedings part I. vol. 25, No. 18S (Jun. 20 Supplement) 2007: abstract 10557).*

(Continued)

*Primary Examiner* — Laura B Goddard
(74) *Attorney, Agent, or Firm* — Kilpatrick Townsend & Stockton LLP

(57) ABSTRACT

In certain aspects, the present invention provides methods for determining whether a Her-2 positive cancer is likely to respond to treatment with a Her2-acting agent and/or whether a patient with a Her-2 positive cancer is likely to have a slow disease progression. In other aspects, the present invention is drawn to methods for determining whether a subject with a Her-2 positive cancer is unlikely to respond to treatment with at least one chemotherapeutic agent in addition to a Her2-acting agent and/or whether a patient with a Her-2 positive cancer is likely to have a fast disease progression.

21 Claims, 47 Drawing Sheets

(56) References Cited

U.S. PATENT DOCUMENTS

| | | | |
|---|---|---|---|
| 7,045,311 B2 | 5/2006 | Ciambrone et al. | |
| 7,105,308 B2 | 9/2006 | Chan-Hui et al. | |
| 7,135,300 B2 | 11/2006 | Chan-Hui et al. | |
| 7,160,735 B2 | 1/2007 | Dehlinger et al. | |
| 7,217,531 B2 | 5/2007 | Singh et al. | |
| 7,255,999 B2 | 8/2007 | Singh et al. | |
| 7,279,585 B2 | 10/2007 | Singh et al. | |
| 7,312,034 B2 | 12/2007 | Virgos et al. | |
| 7,348,010 B2 | 3/2008 | Zielinski et al. | |
| 7,358,052 B2 | 4/2008 | Singh | |
| 7,371,376 B1 | 5/2008 | Fendly | |
| 7,402,397 B2 | 7/2008 | Chan-Hui et al. | |
| 7,402,398 B2 | 7/2008 | Pidaparthi et al. | |
| 7,402,399 B2 | 7/2008 | Mukherjeei et al. | |
| 7,446,185 B2 | 11/2008 | Nelson | |
| 7,537,938 B2 | 5/2009 | Kirakossian et al. | |
| 7,648,828 B2 | 1/2010 | Chan-Hui et al. | |
| 7,700,299 B2 | 4/2010 | Moecks et al. | |
| 7,771,929 B2 | 8/2010 | Singh et al. | |
| 7,939,267 B2 | 5/2011 | Moore et al. | |
| 8,093,216 B2 | 1/2012 | Clinton | |
| 8,189,031 B2 | 6/2012 | Chan-Yui et al. | |
| 8,247,180 B2 | 8/2012 | Pidaparthi et al. | |
| 8,349,574 B2 | 1/2013 | Bates et al. | |
| 8,389,227 B2 | 3/2013 | Lopez et al. | |
| 8,470,542 B2 | 6/2013 | Sperinde et al. | |
| 8,741,586 B2 | 6/2014 | Arribas Lopez et al. | |
| 2002/0013126 A1 | 1/2002 | Raso | |
| 2002/0045738 A1 | 4/2002 | Singh et al. | |
| 2002/0045748 A1 | 4/2002 | Singh et al. | |
| 2002/0058263 A1 | 5/2002 | Singh et al. | |
| 2002/0146726 A1 | 10/2002 | Matray et al. | |
| 2003/0059863 A1 | 3/2003 | Clinton | |
| 2003/0092012 A1 | 5/2003 | Chenna et al. | |
| 2003/0170734 A1 | 9/2003 | Williams et al. | |
| 2003/0170915 A1 | 9/2003 | Singh et al. | |
| 2003/0175747 A1 | 9/2003 | Singh | |
| 2003/0203408 A1 | 10/2003 | Williams et al. | |
| 2003/0207300 A1 | 11/2003 | Matray et al. | |
| 2003/0235832 A1 | 12/2003 | Chenna et al. | |
| 2004/0029139 A1 | 2/2004 | Singh | |
| 2004/0052811 A1 | 3/2004 | Zielinski et al. | |
| 2004/0067498 A1 | 4/2004 | Chenna et al. | |
| 2004/0091850 A1 | 5/2004 | Boone et al. | |
| 2004/0166529 A1 | 8/2004 | Singh et al. | |
| 2004/0175765 A1 | 9/2004 | Singh et al. | |
| 2004/0197815 A1 | 10/2004 | Singh et al. | |
| 2004/0197835 A1* | 10/2004 | Chan-Hui | G01N 33/542 435/7.2 |
| 2004/0229293 A1 | 11/2004 | Chan-Hui et al. | |
| 2004/0229294 A1 | 11/2004 | Chan-Hui et al. | |
| 2004/0229299 A1 | 11/2004 | Badal et al. | |
| 2004/0229380 A1 | 11/2004 | Chan-Hui et al. | |
| 2004/0241686 A1 | 12/2004 | Nelson | |
| 2004/0248150 A1 | 12/2004 | Singh et al. | |
| 2004/0248151 A1 | 12/2004 | Bacus et al. | |
| 2004/0248325 A1 | 12/2004 | Bukusoglu | |
| 2004/0265858 A1 | 12/2004 | Singh et al. | |
| 2005/0048553 A1 | 3/2005 | Chenna et al. | |
| 2005/0130238 A1 | 6/2005 | Chan-Hui et al. | |
| 2005/0130246 A1 | 6/2005 | Salimi-Moosavi et al. | |
| 2005/0131006 A1 | 6/2005 | Mukherjee et al. | |
| 2005/0170438 A1 | 8/2005 | Chan-Hui et al. | |
| 2005/0226872 A1 | 10/2005 | Adam et al. | |
| 2006/0127928 A1 | 6/2006 | Bacus et al. | |
| 2006/0199231 A1 | 9/2006 | Moore et al. | |
| 2006/0204966 A1 | 9/2006 | Spector et al. | |
| 2006/0212956 A1 | 9/2006 | Crocker et al. | |
| 2006/0223107 A1 | 10/2006 | Chenna et al. | |
| 2006/0275305 A1* | 12/2006 | Bryant | 424/155.1 |
| 2007/0037228 A1 | 2/2007 | Moecks et al. | |
| 2007/0059785 A1 | 3/2007 | Bacus et al. | |
| 2007/0203408 A1 | 8/2007 | Say et al. | |
| 2007/0292419 A1 | 12/2007 | Hellmann | |
| 2008/0131883 A1 | 6/2008 | Adams et al. | |
| 2008/0182255 A1 | 7/2008 | Baker et al. | |
| 2008/0187948 A1 | 8/2008 | Chan-Hui et al. | |
| 2008/0233602 A1 | 9/2008 | Chan-Hui et al. | |
| 2008/0254497 A1* | 10/2008 | Singh | 435/29 |
| 2008/0311674 A1 | 12/2008 | Singh et al. | |
| 2009/0011432 A1 | 1/2009 | Chan-Hui et al. | |
| 2009/0011440 A1 | 1/2009 | Mukherjee et al. | |
| 2009/0092617 A1 | 4/2009 | Bock et al. | |
| 2009/0111127 A1 | 4/2009 | Chan-Hui et al. | |
| 2009/0155818 A1 | 6/2009 | Pidaparthi et al. | |
| 2009/0173631 A1 | 7/2009 | Boone et al. | |
| 2009/0191559 A1 | 7/2009 | Huang et al. | |
| 2009/0311262 A1 | 12/2009 | Lopez et al. | |
| 2010/0143927 A1 | 6/2010 | Sperinde et al. | |
| 2010/0210034 A1 | 8/2010 | Bates et al. | |
| 2010/0233732 A1 | 9/2010 | Bates et al. | |
| 2010/0291594 A1 | 11/2010 | Chan-Hui et al. | |
| 2011/0180408 A1 | 7/2011 | Badel et al. | |
| 2011/0318380 A1 | 12/2011 | Brix et al. | |

FOREIGN PATENT DOCUMENTS

| | | | |
|---|---|---|---|
| CN | 1639192 | | 7/2005 |
| CN | 1928563 | | 3/2007 |
| CN | 101115836 | | 1/2008 |
| CN | 101230390 | | 7/2008 |
| EP | 0484027 | | 12/1996 |
| EP | 1278760 | | 6/2008 |
| EP | 1540347 | | 9/2009 |
| EP | 2293819 | | 3/2011 |
| EP | 1918386 | | 10/2011 |
| EP | 2330131 | | 10/2014 |
| ES | 2342646 | A1 | 7/2010 |
| JP | 2006-521821 | | 9/2006 |
| JP | 2006-508336 | | 11/2012 |
| JP | 05117165 | | 1/2013 |
| WO | WO 93/016185 | A2 | 8/1993 |
| WO | WO 99/31140 | | 6/1999 |
| WO | WO 00/66607 | | 11/2000 |
| WO | WO 00/69460 | | 11/2000 |
| WO | WO 01/15730 | | 3/2001 |
| WO | WO 01/083502 | | 11/2001 |
| WO | WO 01/084157 | | 11/2001 |
| WO | WO 02/012547 | | 2/2002 |
| WO | WO 02/094998 | | 11/2002 |
| WO | WO 02/095356 | | 11/2002 |
| WO | WO 03/006947 | | 1/2003 |
| WO | WO 03/032867 | | 4/2003 |
| WO | WO 03/033741 | | 4/2003 |
| WO | WO 03/042398 | | 5/2003 |
| WO | WO 03/042657 | | 5/2003 |
| WO | WO 03/042658 | | 5/2003 |
| WO | WO 03/042699 | | 5/2003 |
| WO | WO 03/051669 | | 6/2003 |
| WO | WO 03/076649 | | 9/2003 |
| WO | WO 03/085374 | | 10/2003 |
| WO | WO 04/008099 | | 1/2004 |
| WO | WO 04/010842 | | 2/2004 |
| WO | WO 04/011900 | | 2/2004 |
| WO | WO 04/061131 | | 7/2004 |
| WO | WO 04/061446 | | 7/2004 |
| WO | WO 04/063700 | | 7/2004 |
| WO | WO 04/068116 | | 8/2004 |
| WO | WO 04/087887 | | 10/2004 |
| WO | WO 04/091384 | | 10/2004 |
| WO | WO 04/092353 | | 10/2004 |
| WO | WO 2004/091384 | * | 10/2004 |
| WO | WO 05/011607 | | 2/2005 |
| WO | WO 05/019470 | | 3/2005 |
| WO | WO 05/037071 | | 4/2005 |
| WO | WO 05/045058 | | 5/2005 |
| WO | WO 05/072507 | | 8/2005 |
| WO | WO 06/044748 | | 4/2006 |
| WO | WO 06/052788 | | 5/2006 |
| WO | WO 2006/068640 | | 6/2006 |
| WO | WO 06/084018 | | 8/2006 |
| WO | WO 2007/035842 | * | 3/2007 |
| WO | WO 2007/041502 | | 4/2007 |
| WO | WO 08/145338 | | 12/2008 |

(56) References Cited

FOREIGN PATENT DOCUMENTS

| WO | WO 09/070772 | 6/2009 |
| --- | --- | --- |
| WO | WO 09/086197 | 7/2009 |
| WO | WO 10/000565 A1 | 1/2010 |
| WO | WO 10/065568 | 6/2010 |
| WO | WO 10/083463 | 7/2010 |
| WO | WO 10/083470 | 7/2010 |

OTHER PUBLICATIONS

Toi et al (Journal of Clinical Oncology, 2007, ASCO Annual Meeting proceedings part I, vol. 25, No. 18S (Jun. 20 Supplement), 2007: Abstract 1025, Poster.*
Chan-Hui et al (Clinical Immunology, 2004, 111:162-174).*
Samur et al (Turk J Med Sci, 2003, 33:363-368).*
Yakut et al (International Journal of Hematology and Oncology, 2006, 16:1-8).*
Thermo Scientific data sheet for Ab-8 (clone e2-4001) (Nov. 27, 2001).*
Thermo Scientific data sheet for Ab-15 (clone 3B5) (Nov. 9, 2007).*
Thermo Scientific data sheet for Ab-17 (clone e2-4001 + clone 3B5) (May 30, 2006).*
Joshi et al (Cytometry Part A, May 2007, 71A:273-285).*
Li et al (Cancer Research, Aug. 2007, 67:7646-7653).*
Birle et al (Molecular Cancer Ther. 2006, 5:2494-2502).*
Hedley et al (Clinical Cancer Research, 2003, 9:5666-5674).*
Atkinson, A., et al., "Biomarkers and Surrogate Endpoints: Preferred Definitions and Conceptual Framework," Clinical Pharmacology & Therapeutics, 2001, 69(3):89-95.
"Theory and Practice of Histological Techniques," 1977, (Bancroft, J.D. & Stevens, A., eds.), Churchill Livingstone, Edinburgh.
Baselga, J., et al., "Phase II Study of Weekly Intravenous Recombinant Humanized Anti-p185$^{HER2}$ Monoclonal Antibody in Patients With HER2/neu-Overexpressing Metastatic Breast Cancer," Clin. Oncol., 1996, 14(3):737-744.
Beutner, S., et al., "Synthetic Singlet Oxygen Quenchers," Meth. Enzymol., 2000, 319:226-241.
Blume-Jenson, P. and Hunter, I., "Oncogenic Kinase Signalling," Nature, 2001, 411:355-365.
Citri, A., et al., "The Deaf and the Dumb: The Biology of ErbB-2 and ErbB-3," Experimental Cell Research, 2003, 284(1):54-65.
Cobleigh, M., et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," J. Clin. Oncol., 1999, 17(9):2639-2648.
Di Mascio, P., et al., "Singlet Molecular Oxygen Production in the Reaction of Peroxynitrite With Hydrogen Peroxide," FEBS Letters, 1994, 355:287-289.
Frank, R. and Hargreaves, R., "Clinical Biomarkers in Drug Discovery and Development," Nature Reviews Drug Discovery, 2003, 2:566-580.
George, S., et al., "G-Protein-Coupled Receptor Oligomerization and Its Potential for Drug Discovery," Nature Reviews Drug Discovery, 2002, 1:808-820.
Giese, R., "Electrophoric Release Tags: Ultrasensitive Molecular Labels Providing Multiplicity," Trends Anal. Chem., 1983, 2(7):165-168.
Goldenberg, M., "Trastuzumab, a Recombinant DNA-Derived Humanized Monoclonal Antibody, A Novel Agent for the Treatment of Metastatic Breast Cancer," Clin. Therap., 1999, 21(2):309-318.
Protective Groups in Organic Synthesis, 3$^{rd}$ Edition, 1991, (Greene, T. and Wuts, P. eds.), John Wiley & Sons, New York.
Antibodies: A Laboratory Manual, 1988, (Harlow, E. and Lane, D. eds.), Cold Spring Harbor Laboratory Press, New York.
Herbst, R., and Shin, D.M., "Monoclonal Antibodies to Target Epidermal Growth Factor Receptor-Positive Tumors. A New Paradigm for Cancer Therapy," Cancer, 2002, 94(5):1593-1611.
Basic Methods in Antibody Production and Characterization, 2001, (Howard, G. and Bethell D. eds.), CRC Press.

Schaap, A., et al., "Polymer-Based Sensitizers for Photooxidations. II," J.Amer. Chem. Soc., 1975, 97:3741-3745.
Kanofsky, J., "Singlet Oxygen Production by Lactoperoxidase: Evidence from 1270 nm Chemiluminescence," J. Biol. Chem., 1983, 258(10):5991-5993.
Lee, L., et al., "New Energy Transfer Dyes for DNA Sequencing," Nucleic Acids Research, 1997, 25(14):2816-2822.
Manual of Histological Staining Methods of the Armed Forces Institute of Pathology, 3$^{rd}$ Edition, 1960, (Luna, L.G. ed.), McGraw-Hill Book Company (Blakiston Division), New York.
Martin, J. and Burch, P., "Production of Oxygen Radicals by Photosensitization," Meth. Enzymol., 1990, 186:635-645.
McCormick, F. "Signalling Networks That Cause Cancer," Trends Cell Biol., 1999, 9:M53-M56.
Mellado, M., et al., "Chemokine Signaling and Functional Responses: The Role of Receptor Dimerization and TK Pathway Activation," Ann. Rev. Immunol., 2001, 19:397-421.
High Resolution Chromatography: A Practical Approach, 1999, (Millner, P. ed.), Oxford University Press, New York.
Neckers, L. and Ivy, S., "Heat Shock Protein 90," Curr. Opin. Oncol., 2003, 15(6):419-424.
HPLC of Macromolecules: A Practical Approach, 1989, (Oliver, R. ed.), Oxford University Press, Oxford, England.
Histochemistry: Theoretical and Applied, 4$^{th}$ ed., 1980, (Pearse, A. ed.), Churchill Livingstone, Edinburgh.
Petricoin, E., et al., "Clinical Proteomics: Translating Benchside Promise Into Bedside Reality," Nature Reviews Drug Discovery, 2002, 1:683-695.
Pierlot, C., et al., "Naphthalene Endoperoxides as Generators of Singlet Oxygen in Biological Media," Meth. Enzymol., 2000, 319:3-20.
Schlessinger, J., "Cell Signaling by Receptor Tyrosine Kinases," Cell, 2000, 103:211-225.
Semba, K., et al., "A v-erbB-Related Protooncogene, c-erbB-2, Is Distinct From the c-erbB-1/Epidermal Growth Factor-Receptor Gene and Is Amplified in a Human Salivary Gland Adenocarcinoma," Proc. Natl. Acad. Sci. USA, 1985, 82:6497-6501.
Shak, S., "Overview of the Trastuzumab (Herceptin) Anti-HER2 Monoclonal Antibody Clinical Program in HER2-Overexpressing Metastatic Breast Cancer," Sem. Oncol., 1999, 26(4):71-77.
Shi, E., et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Abstracts—Poster Session II, Dec. 2007, 106(Suppl. 1):S87-S88.
Sidransky, D., "Emerging Molecular Markers of Cancer," Nature Reviews Cancer, 2002, 2:210-219.
Slamon, D., et al., "Use of Chemotherapy Plus a Monoclonal Antibody Against HER2 for Metastatic Breast Cancer That Overexpresses HER2," N. Eng. J. Med., 2001, 344(11):783-792.
Practical HPLC Method Development, 1988, (Snyder, L., et al. eds.), John Wiley & Sons, New York.
Strong, L., et al., "Antibody-Targeted Photolysis: Photophysical, Biochemical, and Pharmacokinetic Properties of Antibacterial Conjugates," Ann. New York Acad. Sci., 1994, 745:297-320.
Ullman, E., et al., "Luminescent Oxygen Channeling Immunoassay: Measurement of Particle Binding Kinetics by Chemiluminescence," Proc. Natl. Acad. Sci. USA, 1994, 91:5426-5430.
Vogel, C., et al., "Efficacy and Safety of Trastuzumab As a Single Agent in First-Line Treatment of HER2-Overexpressing Metastatic Breast Cancer," J. Clin. Oncol., 2002, 20:719-726.
The Immunoassay Handbook, 1994, (Wild, D. ed.), Stockton Press, New York.
Column Handbook for Size Exclusion Chromatography, 1999, (Wu, C.S. ed.), Academic Press, San Diego.
Yamamoto, T., et al., "Similarity of Protein Encoded by the Human c-erb-B-2 Gene to Epidermal Growth Factor Receptor," Nature, 1986, 319:230-234.
Yarden, Y., "The EGFR Family and Its Ligands in Human Cancer: Signalling Mechanisms and Therapeutic Opportunities," Eur. J. Cancer, 2001, 37:S3-S8.

(56) References Cited

OTHER PUBLICATIONS

Yarden, Y. and Sliwkowski, M.X., "Untangling the ErbB Signalling Network," Nature Reviews Molecular Cell Biology, 2001, 2:127-137.
Yarmush, M., et al., "Antibody Targeted Photolysis," Crit. Rev. Therapeutic Drug Carrier Sys., 1993, 10(3):197-252.
Zhang, X., et al., "Synthesis of Releasable Electrophore Tags for Applications in Mass Spectrometry," Bioconjugate Chem., 2002, 13:1002-1012.
Therasse, P., et al., "New Guidelines to Evaluate the Response to Treatment in Solid Tumors," J. Natl. ancer Institute, 92(3):205-216.
Nagy, P., et al., "Lipid Rafts and the Local Density of ErbB Proteins Influence the Biological Role of Homo- And Heteroassociations of ErbB2," J. Cell Science, 2002, 115:4251-4262.
Tandon, S., et al., "Her-2 /neu Oncogene Protein and Prognosis in Breast Cancer," J. Clin. Oncol., 1989, 7(8): 1120-1128.
Armed Forces Institute of Pathology Advanced Laboratory Methods in Histology and Pathology, Armed Forces Institute of Pathology, American Registry of Pathology, (Mikel, U.V. ed.), 1994, Washington, DC.
International Search Report and Written Opinion dated Mar. 17, 2009 for corresponding PCT application PCT/US2008/087828.
Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," American Society of Clinical Oncology (ASCO) Conference 2007, Jun. 1-5, Chicago, IL.
Bates, M. et al., "Identification of a Subpopulation of Metastatic Breast Cancer Patients with Very High HER2 Expression Levels and Possible resistance to Trastuzumab," Annals of Oncology, published online Feb. 2, 2011.
Joensuu, H. et al., "Very High Quantitative Tumor HER2 Content and Outcome in Early Breast Cancer," Annals of Oncology, published online Feb. 1, 2011.
Toi, M. et al., "The Use of ErbB/HER Activation Status as Prognostic Markers in Breast Cancer Patients Treated with Trastuzumab," American Society of Clinical Oncology (ASCO) Conference 2005, May 13-17, Orlando, FL.
Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK.
Toi, M. et al., "Differential Survival following Trastuzumab Treatment based on Quantitative HER2 Expression and HER2:HER2 Dimerization in a Clinic-Based Cohort of Patients with Metastatic Breast Cancer," American Society of Clinical Oncology (ASCO) Conference 2007, Jun. 1-5, Chicago, IL.
Bates, M.P., et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," Journal of Clinical Oncology, 2007, 25:18S.
Dua, R., et al., "Profiling HER-Family Receptor Dimerization in HER2 Overexpressing Cells that Coexpress Mutated EGFR Receptors," Breast Cancer Research and Treatment, 2007, 106(1):S203.
Dua, R., et al., "Patterns of HER-Family Receptor Dimerization Intrastuzumab Susceptible and Trastuzumab Resistant Cell Lines," Journal of Clinical Oncology, 2007, 25:18S.
Eli, L., et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, 2007, 106(1):S87-S88.
Huang, W., et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, 2007, 106(1)S86.
Wallweber, J., et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, 2007, 106(1):S207.
Winslow, J., et al., "Characterization of a Novel Proximity Immunoassay for the Quantitative Determination of HER2 Protein Expression and HER2 Homodimerization in Famalin-Fixed, Paraffin-Embedded Breast Cancer Tissue," Breast Cancer Research and Treatment, 2007, 106(1):S88.
Toi, M., et al., "Differential Survival Following Trastuzumab Treatment Based on Quantitative HER2 Expression and HER2 Dimerization in a Clinic-Based Cohort of Patients With Metastatic Breast Cancer," Journal of Clinical Oncology, 2007, 25:18S.
Extended European Search Report dated Apr. 5, 2011 for corresponding European Application No. 08868829.6.
Bates, M.P., et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," J. of Clinical Oncology, 2007 (Jun. 20, 2007 Supplement), 25:18S (Abstract).
Dua, R., et al., "Profiling HER-Family Receptor Dimerization in HER2 Overexpressing Cells that Coexpress Mutated EGFR Receptors," Breast Cancer Research and Treatment, Dec. 13, 2007, 106(1):S203 (Abstract).
Dua, R., et al., "Profiling HER-Family Receptor Dimerization in HER2 Overexpressing Cells that Coexpress Mutated EGFR Receptors," 30th Annual San Antonio Breast Cancer Symposium, Dec. 13-16, 2007; San Antonio, TX, USA (Poster).
Dua, R., et al., "Patterns of HER-Family Receptor Dimerization Intrastuzumab Susceptible and Trastuzumab Resistant Cell Lines," J. of Clinical Oncology, Jun. 20, 2007, 25:18S (Abstract).
Dua, R., et al., "Patterns of HER-Family Receptor Dimerization Intrastuzumab Susceptible and Trastuzumab Resistant Cell Lines," American Society of Clinical Oncology (ASCO) Conference 2007, Jun. 1-5, Chicago, IL, USA (Poster).
Eli, L., et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Dec. 13, 2007, 106(1):S87-S88 (Abstract).
Eli, L., et al., "Development of Novel Proximity-Based Immunoassays for the Detection of HER Heterodimerization in Breast Cancer Cell Line Lysates and Formalin-Fixed, Paraffin-Embedded Tissue," 30th Annual San Antonio Breast Cancer Symposium, Dec. 13-16, 2007; San Antonio, TX, USA (Poster).
Huang, W., et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, Dec. 13, 2007, 106(1):S86 (Abstract).
Huang, W., et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," 30th Annual San Antonio Breast Cancer Symposium, Dec. 13-16, 2007; San Antonio, TX, USA (Poster).
Toi, M., et al., "Differential Survival Following Trastuzumab Treatment Based on Quantitative HER2 Expression and HER2 Dimerization in a Clinic-Based Cohort of Patients With Metastatic Breast Cancer," J. of Clinical Oncology, 2007 (Jun. 20, 2007 Supplement), 25:18S (Abstract).
Wallweber, J., et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, Dec. 13, 2007, 106(1):S207 (Abstract).
Wallweber, J., et al., "Increased Detection of Breast Cancer Markers Human Epidermal Growth Factor Receptor Dimer and Downstream Signaling Proteins Utilizing the VeraTag Technology with Dextran Modified Antibodies," 30th Annual San Antonio Breast Cancer Symposium, Dec. 13-16, 2007; San Antonio, TX, USA (Poster).
Winslow, J., et al., "Characterization of a Novel Proximity Immunoassay for the Quantitative Determination of HER2 Protein Expression

(56) References Cited

OTHER PUBLICATIONS and HER2 Homodimerization in Famalin-Fixed, Paraffin-Embedded Breast Cancer Tissue," Breast Cancer Research and Treatment, Dec. 13, 2007, 106(1):S88 (Abstract).
Winslow, J., et al., "Characterization of a Novel Proximity Immunoassay for the Quantitative Determination of HER2 Protein Expression and HER2 Homodimerization in Famalin-Fixed, Paraffin-Embedded Breast Cancer Tissue," 30th Annual San Antonio Breast Cancer Symposium, Dec. 13-16, 2007; San Antonio, TX, USA (Poster).
Mukherjee, A. et al., "Correlation of ErbB activation status and clinical response in Herceptin treated breast cancer patients," Proc. Amer. Canc. Res., Apr. 16-20, 2005, 46: 3688 (Abstract).
Mukherjee, A. et al., "Correlation of ErbB activation status and clinical response in Herceptin treated breast cancer patients," 96th Annual Meeting of the American Association for Cancer Research, Apr. 16-20, 2005, Anaheim/Orange County, CA, USA (Poster).
Wolff, A.C., et al., "American Society of Clinical Oncology/College of American Pathologists Guideline Recommendations for Human Epidermal Growth Factor Receptor 2 Testing in Breast Cancer," J. of Clinical Oncology, Jan. 1, 2007, 25(1): 118-145 (published online Dec. 11, 2006).
Amler, L. et al., "Downregulation of HER3 may predict clinical benefit in ovarian cancer from pertuzumab, a HER2 dimerization-inhibiting antibody," 2008, Molecular Markers Meeting, Amer. Soc. Clin. Onc., Abstract 25.
Anido, J. et al., "Biosynthesis of Tumorigenic HER2 C-terminal Fragments by Alternative Initiation of Translation," 2006, EMBO J., 25:3234-3244.
Arkin, M. and Moasser, M., "HER-2-directed, small-molecule antagonists," 2008, Curr. Opin. Investig. Drugs, 9(12):1264-1276.
Bagashawe, K. et al., "A Cytotoxic Agent Can Be Generated Selectively At Cancer Sites," 1987, Brit. J. Cancer, 58:(6):700-703.
Bianco, R. et al., "Rational bases for the development of EGFR inhibitors for cancer treatment," 2007, Int. J. Biochem. Cell Biol., 39:1416-1431.
Bioconjugate Techniques, 1996, Hermanson, G., ed., Academic Press, New York.
Burgess, A. et al., "An Open-and-Shut Case? Recent Insights into the Activation of EGF/ErbB Receptors," 2003, Mol. Cell, 12:541-552.
Burgess, A., "EGFR family: Structure physiology signalling and therapeutic targets," 2008, Growth Factors 26:263-274.
Britten, C.D., "Targeting ErbB receptor signaling: A pan-ErbB approach to cancer," 2004, Molec. Canc. Ther., 3(10):1335-1342.
Cappuzzo, F. et al., "HER3 genomic gain and sensitivity to gefitinib in advanced non-small-cell lung cancer patients," 2005, Brit. J. Cancer, 93:1334-1340.
Carden, C.P. et al., "From Darkness to Light with Biomarkers in Early Clinical Trials of Cancer Drugs," 2009, Clin. Pharmacol. Ther., 85(2):131-133.
Carter, P. et al., "Humanization of an Anti-p185$^{HER2}$ Antibody for Human Cancer Therapy," 1992, Proc. Natl. Acad. Sci. USA, 89:4285-4289.
Carter, P. and Senter, P., "Antibody-Drug Conjugates for Cancer Therapy," 2008, The Cancer Journal, 14(3):154-169.
De Alava, E. et al., "Neuregulin Expression Modulates Clinical Response to Trastuzumab in Patients With Metastatic Breast Cancer," 2007, J. Clin. Oncol., 25(19):2656-2663.
Dhani, N. and Siu, L., "Clinical trials and biomarker development with molecularly targeted agents and radiotherapy," 2008, Cancer Metastasis Rev., 27:339-349.
Engvall, E., "Enzyme-Linked Immunosorbent Assay, ELISA," 1977, In: Biomedical Applications of Immobilized Enzymes and Proteins, (Chang, T. ed.), 2:87-96, Plenum Press, New York.
Fuchs, I. et al., Epidermal Growth Factor Receptor Changes During Breast Cancer Metastasis, 2006, Anticancer Res., 26:4397-4402.
Garcia-Castillo, J., et al., "HER2 Carboxyl-Terminal Fragments Regulate Cell Migration & Cortactin Phosphorylation," 2009, J. Biol. Chem., 284(37):25301-25313.

Gee, J. and Knowlden, J., "Adam Metalloproteases and EGFR Signalling," 2003, Breast Cancer Res., 5:223-224.
Genbank accession No. X03363, "Human c-erb-B-2 mRNA."
Graham, F. et al., "Characteristics of a Human Cell Line Transformed by DNA from Human Adenovirus Type 5," 1977, J. Gen. Virol., 36:59-74.
Haugland, R., Handbook of Fluorescent Probes and Research Products, 2002, 9th Ed.(Gregory, J. ed.), Molecular Probes, Eugene, OR.
Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, Dec. 13, 2007, 106(1 Suppl.):S86 (Abstract 2007).
Huang, W. et al., "Comparison of Central HER-2 Tests With Quantitative HER-2 Expression and HER-2 Homodimer Measurements Using a Novel Proximity Based Assay," 2008 Arch. Pathol. Lab. Med. 132 (Sep.):1476 (CAP Abstract 40).
Huang, W. et al., "Comparison of Central HER-2 Tests With Quantitative HER-2 Expression and HER-2 Homodimer Measurements Using a Novel Proximity Based Assay," American College of Pathologist (CAP) Annual Meeting, Sep. 25-28, 2008 (Poster 40).
International Search Report and Written Opinion dated Mar. 1, 2010, corresponding to International Application No. PCT/US10/21272.
International Search Report and Written Opinion dated May 25, 2010, corresponding to International Application No. PCT/US09/66295.
International Search Report and Written Opinion dated Jun. 2, 2010, corresponding to International Application No. PCT/US10/21281.
International Prelimary Report on Patentability dated Dec. 2, 2011, corresponding to International Application No. PCT/US10/21272.
Joensuu, H. et al., "Adjuvant Docetaxel or Vinorelbine with or without Trastuzumab for Breast Cancer," 2006, N. Engl. J. Med., 354:809-820.
Kraus, M. et al., "Isolation and characterization of ERBB3, a third member of the ERBB/epidermal growth factor receptor family: Evidence for overexpression in a subset of human mammary tumors," 1989, Proc. Natl. Acad. Sci. USA, 86:9193-9197.
Kreitman, R., "Immunotoxins for Targeted Cancer Therapy," 2006, AAPS J., 18:E532-E551.
Latch, D. and McNeill, K. "Microheterogeneity of Singlet Oxygen Distributions in Irradiated Humic Acid Solutions," 2006, Science, 311:1743-1747.
Lee, J. et al., "Biomarker Assay Translation from Discovery to Clinical Studies in Cancer Drug Development: Quantification of Emerging Protein Biomarkers," 2007, In: Advances in Cancer Research (Woude, G. et al.), eds., 96:269-298.
Lee-Hoeflich, S. et al., "A Central Role for HER3 in HER2-Amplified Breast Cancer: Implications for Targeted Therapy," 2008, Cancer Res., 68(14):5878-5887.
Lipton, A. et al., "HER2 protein expression predicts response to trastuzumab in FISH-positive patients," 2008 Cancer Res., 69(2 Suppl):Abstract 32.
Liu, P. et al. , "Identification of ADAM10 As a Major Source of HER2 Ectodomain Sheddase Activity in HER2 Overexpressing Breast Cancer Cells," 2006, Cancer Biol. Therapy, (5)6:657-664.
Lizardi, P. et al., "Mutation Detection and Single-Molecule Counting Using Isothermal Rolling-Circle Amplification," 1998 Nat. Genet., 19:225-232.
Ludwig, J. and Weinstein, J., "Biomarkers in Cancer Staging, Prognosis and Treatment Selection," 2005, Nature Reviews Cancer, 5:845-856.
Ma, C. and Bose, R., "Current and Future Roles of Lapatinib in HERs-Positive Breast Cancer," 2008, E-Updates in HER1 and HER2 Targeting in Breast Cancer, vol. 2 (Sep. 1).
Makhija, S. et al., "HER pathway gene expression analysis in a phase II study of pertuzumab + gemcitabine vs. gemcitabine + placebo in patients with platinum-resistant epithelial ovarian cancer," 2008, J. Clin. Oncol. (May 20 Supplement), 26:ASCO Abstract 5552.
Menendez, J. and Lupu, R., "Transphosphorylation of kinase-dead HER3 and breast cancer progression: a new standpoint or an old concept revisited?," 2007, Breast Cancer Research, 9:111 (5 pp.).

(56) References Cited

OTHER PUBLICATIONS

Mignot, G. et al., "Prospects for Exosomes in Immunotherapy of Cancer," 2006, J. Cell. Mol. Med., 10(2):376-388.
Molina, M. et al., "NH²-terminal Truncated HER-2 Protein But Not Full-Length Receptor Is Associated With Nodal Metastasis in Human Breast Cancer," 2002, Clin. Can. Res., 8:347-353.
Monoclonal Antibodies. Hybridomas: A New Dimension in Biological Analyses, 1980, (Kennett, R. et al., eds.), Plenum Press, New York.
Mosesson, Y. et al., "Oncogenic Growth Factor Receptors: Implications for Signal Transduction Therapy," 2004, Semin. Cancer Biol., 14:262-270.
NCBI Accession No. NM_001982.2, Homo sapiens v-erb-b2 erythroblastic leukemia viral oncogene homolog 3 (avian) (ERBB3), transcript variant 1, mRNA.
NCBI Accession No. P00533 (protein) Epidermal growth factor.
NCBI Accession No. P21860 (protein) Receptor tyrosine-protein kinase erbB-3.
NCBI Accession No. X03363, Human c-erb-B-2 mRNA.
Normanno, N. et al., "Epidermal growth factor receptor (EGFR) signaling in cancer," 2006, Gene, 366:2-16.
Ono, M. and Kuwano, M., "Molecular Mechanisms of Epidermal Growth Factor Receptor (EGFR) Activation and Response to Gefitinib and Other EGFR-Targeting Drugs," 2006, Clin. Cancer Res., 12:7242-7251.
Osipo, C. et al., "Role for HER2/neu and HER3 in fulvestrant-resistant breast cancer," 2007, Int. J. Oncol., 30:509-520.
Pedersen, K. et al., "A Naturally Occurring HER2 Carboxy-Terminal Fragment Promotes Mammary Tumor Growth and Metastasis," 2009, Mol. Cell. Biol., 29(12):3319-3331.
Plowman, G. et al., "Molecular cloning and expression of an additional epdermal growth factor receptor-related gene," 1990, Proc. Natl. Acad. Sci. USA, 87:4905-4909.
Practical Nonparametric Statistics, 1999, 3rd Ed. (Conover, W.J., ed.) John Wiley & Sons, New York.
"Radioimmunoassay and Saturation Analysis," 1974, British Medical Bulletin, (Sonksen, P.H. ed.), 30:1-103.
Riechmann, L. et al., "Reshaping Human Antibodies for Therapy," 1988, Nature, 332:323-327.
Romond, E., "Trastuzumab Plus Adjuvant Chemotherapy for Operable HER2-Positive Breast Cancer," 2005, N. Engl. J. Med., 353(16):1673-1684.
Sahin, U. et al., "Distinct Roles for ADAM10 and ADAM17ln Ectodomain Shedding of Six EGFR Ligands," 2004, J. Cell Biol., 164(5):769-779.
Saez, R. et al., "p95HER-2 Predicts Worse Outcome in Patients With HER-2-Positive Breast Cancer," 2006, Clin. Cancer Res., 12(2):424-431.
Scaltriti, M. et al., "Expression of p95HER2, a Truncated Form of the HER2 Receptor, and Response to Anti-HER2 Therapies in Breast Cancer," 2007, J Natl. Can. Ins., 99:628-38.
Senter, P. et al., "Anti-Tumor Effects of Antibody-Alkaline Phosphatase Conjugates in Combination With Etoposide Phosphate," 1988, Proc. Natl. Acad. Sci. USA, 85:4842-4846.
Sergina, N. et al., "Escape from HER-family tyrosine kinase inhibitor therapy by the kinase-inactive HER3," 2007, Nature, 445:437-441.
Sims, M. etal., "A Humanized CD18 Antibody Can Block Function Without Cell Destruction," 1993, J. Immunol.,151:2296-2308.
Sithanandam, G. and Anderson, L., "The ERBB3 receptor in cancer and cancer gene therapy," 2008, Cancer Gene Ther., 15:413-448.
Spector, N. et al., "HER2 Therapy. Small Molecule HER-2 Tyrosine Kinase Inhibitors," 2007, Breast Cancer Res., 9:205-212.
Stern, D., "ERBB3/HER3 and ERBB2/HER2 Duet in Mammary Development and Breast Cancer," 2008, J. Mammary Gland Biol. Neoplasia, 13:215-223.
Taylor, D. and Black, P., "Inhibition of Macrophage Ia Antigen Expression by Shed Plasma Membrane Vesicles From Metastatic Murine Melanoma Lines," 1985, J. Natl. Cancer Inst., 74:859-867.
Tovey, S. et al., "Low expression of HER2 protein in breast cancer is biologically significant," 2006, J. Pathol., 210:358-362.
Voller, A et al., "Enzyme Immunoassays With Special Reference to ELISA Techniques," 1978, J. Clin. Pathol., 31:507-520.
Wallweber, J. et al., "Increased Detection of Breast Cancer Markers Human Epidermal Growth Factor Receptor Dimer and Downstream Signaling Proteins Utilizing the Vera Tag Technology with Dextran Modified Antibodies," Breast Cancer Research and Treatment, Dec. 13, 2007, 106(1):S207.
Xia, W. et al., "Truncated ErbB2 Receptor (p95$^{Erb82}$) Is Regulated by Heregulin Through Heterodimer Formation With ErbB3 Yet Remains Sensitive to the Dual EGFR/ErbB2 Kinase Inhibitor GW572016," 2004, Oncogene, 23(3):646-653.
Xu, F. et al., "The Outcome of Heregulin-induced Activation of Ovarian Cancer Cells Depends on the Relative Levels of HER-2 and HER-3 Expression," 1999, Clin. Cancer Res., 5:3653-3660.
Yuan, C. et al., "Purification of Her-2 Extracellular Domain and Identification of Its Cleavage Site," 2003, Prot. Expr & Purif., 29:217-222.
Zabrecky, J. et al., "The Extracellular Domain of p185/neu Is Released From the Surface of Human Breast Carcinoma Cells, SK-BR-3," 1991, J. Biol. Chem., 266(3):1716-1720.
Zola, H., "Monoclonal Antibodies: A Manual of Techniques," 1987, CRC Press, Boca Raton, Florida.
Biernat, W. et al., "Quantitative HER2 levels and steroid receptor expression in primary breast cancers and in matched brain metastases," 2012 J. Clin. Oncol. 30 (Jun. 20 Suppl.): Abstract 603.
Biernat, W. et al., "Quantitative HER2 levels and steroid receptor expression in primary breast cancers and in matched brain metastases," 35$^{th}$ Annual American Society of Clinical Oncology (ASCO) Conference, May 31-Jun. 4, 2012; Chicago, IL (Poster 603).
Huang, W. et al., "Quantitative HER2 measurement and PI3K mutation profile in matched primary and metastatic breast cancer tissues," 2012 J. Clin. Oncol. 30 (Jun. 20 Suppl.): Abstract 614.
Huang, W. et al., "Quantitative HER2 measurement and PI3K mutation profile in matched primary and metastatic breast cancer tissues," 35$^{th}$ Annual American Society of Clinical Oncology (ASCO) Conference, May 31-Jun. 4, 2012, Chicago, IL (Poster 614).
Sperinde, J. et al., "A comparative study of p95-HER2 carboxy terminal fragment (CTF) detected by immunohistochemistry and VeraTag immunoassays in human breast tumors," In: Proc. Am. Assoc. Cancer Res., Mar. 31, 2012-Apr. 4, 2012, Chicago, IL. Philadelphia (PA): AACR; Cancer Res. 2012, 72(8 Suppl): Abstract 687.
Sperinde, J. et al., "A comparative study of p95-HER2 carboxy terminal fragment (CTF) detected by immunohistochemistry and VeraTag immunoassays in human breast tumors," 103$^{rd}$ Annual American Association for Cancer Research (AACR) Conference, Mar. 31-Apr. 4, 2012, Chicago, IL (Poster 687).
Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 2012 J. Clin. Oncol. 30 (Jun. 20 Suppl.): Abstract 608.
Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 35$^{th}$ Annual American Society of Clinical Oncology (ASCO) Conference, May 31-Jun. 4, 2012, Chicago, IL (Poster 608).
Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," 2011 J. Clin. Oncol. 29(15)(May 20 Suppl.): Abstract 586.
Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," American Society of Clinical Oncology (ASCO) Annual Meeting, Jun. 3-7, 2011, Chicago, IL (Poster 586).

(56) References Cited

OTHER PUBLICATIONS

Cook, J.W. et al., "Mutations in the catalytic domain of PI3 kinase and correlation with clinical outcome in trastuzumab-treated metastatic breast cancer (MBC)," 2011 J. Clin. Oncol. 29(15)(May 20 Suppl.): Abstract 582.
Cook, J.W. et al., "Mutations in the catalytic domain of PI3 kinase and correlation with clinical outcome in trastuzumab-treated metastatic breast cancer (MBC)," American Society of Clinical Oncology (ASCO) Annual Meeting, Jun. 3-7, 2011, Chicago, IL (Poster 582).
Duchnowska, R. et al., "Correlation between Quantitative HER2 Protein Expression and Risk of Brain Metastases in HER2-Positive Advanced Breast Cancer Patients Receiving Trastuzumab-Containing Therapy," Cancer Research, Dec. 15, 2011, 71(24 Suppl. 3):291s (Abstract P2-12-05).
Duchnowska, R. et al., "Correlation between Quantitative HER2 Protein Expression and Risk of Brain Metastases in HER2-Positive Advanced Breast Cancer Patients Receiving Trastuzumab-Containing Therapy," Annual San Antonio Breast Cancer Symposium, Dec. 6-10, 2011, San Antonio, TX, USA (Poster P2-12-05).
Huang, W. et al., "Comparison of four HER2 testing methods in detection of HER2-positive breast cancer: results in the FinHer study cohort," Cancer Research, Dec. 15, 2011, 71(24)(Suppl. 3):187s-188s (Abstract P1-07-01).
Huang, W. et al., "Comparison of four HER2 testing methods in detection of HER2-positive breast cancer: results in the FinHer study cohort," Annual San Antonio Breast Cancer Symposium, Dec. 6-10, 2011, San Antonio, TX, USA (Poster P1-07-01).
Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Cancer Research, Dec. 15, 2011, 71(24)(Suppl. 3):192s-193s (Abstract P1-07-12).
Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Annual San Antonio Breast Cancer Symposium, Dec. 6-10, 2011, San Antonio, TX, USA (Poster P107-12).
Shi, Y. et al., "Quantitative measurement of HER3-PI3K complex and total p85α subunit in formalin-fixed, paraffin-embedded (FFPE) tissues using VeraTag™ immunoassays," American Association for Cancer Research Special Conference: Targeting PI3K/mTOR Signaling in Cancer, Feb. 24-27, 2011, San Francisco, CA: Poster.
Wallweber, J. et al., "Subclassification of squamous cell carcinomas of the head and neck based on HER/ErbB and c-MET receptor protein expression and activation profiles," In: Proc. Am. Assoc. Cancer Res. AACR, Apr. 2-6, 2011, Orlando, FL: Abstract LB-323.
Wallweber, J. et al., "Subclassification of squamous cell carcinomas of the head and neck based on HER/ErbB and c-MET receptor protein expression and activation profiles," American Association for Cancer Research (AACR) Annual Meeting, Apr. 2-6, 2011, Orlando, FL (Poster LB-323).
Duchnowska, R. et al., "Correlation between quantitative HER2 Protein level and the risk of brain metastases (BM) in patients (ots) with metastatic breast cancer (MBC) treated with trastuzumab-containing therapy," 2010 J. Clin. Oncol. 28(15s) (Jun. 20 Suppl.): Abstract 1030.
Duchnowska, R. et al., "Correlation between quantitative HER2 Protein level and the risk of brain metastases (BM) in patients (ots) with metastatic breast cancer (MBC) treated with trastuzumab-containing therapy," American Society of Clinical Oncology (ASCO) Annual Meeting, Jun. 4-8, 2010, Chicago, IL (Poster 1030).
Wallweber, J., "Quantitative assessment of HER/erbB receptor protein expression and activation status in FFPE tumor samples identifies an activated HER1 signature in squamous cell carcinomas of the head and neck," In: Proc. Am. Assoc. Cancer Res. AACR, Apr. 17-21, 2010, Washington, D.C.: Abstract LB-66.
Wallweber, J., "Quantitative assessment of HER/erbB receptor protein expression and activation status in FFPE tumor samples identifies an activated HER1 signature in squamous cell carcinomas of the head and neck," American Association for Cancer Research (AACR) Annual Meeting, Apr. 17-21, 2010, Washington, D.C. (Poster LB-66).
Bates, M. et al., "Relationship between Quantitative HER2 Protein Expression and Clinical Outcomes in ER-Positive and ER-Negative Sub-Groups of Patients with Trastuzumab," Dec. 15, 2009, Cancer Research 69(24)(Suppl. 1): Abstract 5136.
Bates, M. et al., "Relationship between Quantitative HER2 Protein Expression and Clinical Outcomes in ER-Positive and ER-Negative Sub-Groups of Patients with Trastuzumab," $32^{nd}$ Annual San Antonio Breast Cancer Symposium, Dec. 9-13, 2009, San Antonio, TX, USA (Poster 5136).
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," In: Proc. Am. Assoc. Cancer Res. AACR, Apr. 18-22, 2009, Denver, CO: Abstract 5427.
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," American Association of Cancer Research (AACR) Annual Meeting, Apr. 18-22, 2009, Denver, CO (Poster 5427).
Joensuu, H. et al. "Breast cancer patients with very high tumor HER2 expression levels might not benefit from treatment with trastuzumab plus chemotherapy: A retrospective exploratory analysis of the FinHer trial," Dec. 15, 2009, Cancer Research 69(24)(Suppl. 1): Abstract 5083.
Joensuu, H. et al. "Breast cancer patients with very high tumor HER2 expression levels might not benefit from treatment with trastuzumab plus chemotherapy: A retrospective exploratory analysis of the FinHer trial," $32^{nd}$ Annual San Antonio Breast Cancer Symposium, Dec. 10-13, 2009, San Antonio, TX, USA.
Williams, S. et al., "Profiling PI3K-Akt pathway activation in formalin fixed, paraffin-embedded cell line models and breast and ovarian tumors using a novel proximity assay," In: Proc. Am. Assoc. Cancer Res. AACR, Apr. 18-22, 2009, Denver, CO: Abstract 5251.
Williams, S. et al., "Profiling PI3K-Akt pathway activation in formalin fixed, paraffin-embedded cell line models and breast and ovarian tumors using a novel proximity assay," American Association of Cancer Research (AACR) Annual Meeting, Apr. 18-22, 2009, Denver, CO (Poster 5251).
Lipton, A. et al., "Multiple Subtypes of HER-2/Neu-Positive Metastatic Breast Cancer," Cancer Research, Dec. 15, 2009, 69(24 Suppl. 1): Abstract 2030.
Lipton, A. et al., "Multiple Subtypes of HER-2/Neu-Positive Metastatic Breast Cancer," $32^{nd}$ Annual San Antonio Breast Cancer Symposium, Dec. 9-13, 2009, San Antonio, TX, USA (Poster 2030).
Shi, Y. et al., "Quantitative, sensitive, and reproducible measurement of epidermal growth factor receptor/HER1 homodimerization and total expression in formalin-fixed, paraffin-embedded tumors using a novel proximity-based assay," In: Proc. Am. Assoc. Cancer Res. AACR, Apr. 18-22, 2009, Denver, CO: Abstract 5244.
Shi, Y. et al., "Quantitative, sensitive, and reproducible measurement of epidermal growth factor receptor/HER1 homodimerization and total expression in formalin-fixed, paraffin-embedded tumors using a novel proximity-based assay," American Association of Cancer Research (AACR) Annual Meeting, Apr. 18-22, 2009 Denver, CO (Poster 5244).
Leitzel, A. et al., "Discordant HER2 Total and HER2 Homodimer Levels by HERmark Analysis in Matched Primary and Metastatic Breast Cancer FFPE Specimens," Cancer Research, Dec. 15, 2009, 69(24 Suppl. 1): Abstract 2132.
Leitzel, A. et al., "Discordant HER2 Total and HER2 Homodimer Levels by HERmark Analysis in Matched Primary and Metastatic Breast Cancer FFPE Specimens," $32^{nd}$ Annual San Antonio Breast Cancer Symposium, Dec. 9-13, 2009, San Antonio, TX, USA (Poster 2132).
Badal, M.Y. et al., "Measurement of the HER3-PI3K complex as a marker of PI3K-Akt pathway activation in formalin fixed, paraffin-embedded cell line models and breast and ovarian tumors using a novel proximity assay," American Association for Cancer Research

(56) References Cited

OTHER PUBLICATIONS (AACR) Special Conference on Targeting the PI3K-Kinase Pathway in Cancer, Nov. 11-14, 2008, Cambridge, MA, USA (Poster).
Bates, M., et al., "Quantitative HER2 homodimer levels correlate with time to first recurrence in HER2-positive breast cancer patients who did not receive trastuzumab in the adjuvant setting," Cancer Res. Jan. 15, 2009, 69(2 Suppl. 1): Abstract 1074.
Bates, M. et al., "Quantitative HER2 homodimer levels correlate with time to first recurrence in HER2-positive breast cancer patients who did not receive trastuzumab in the adjuvant setting," 31$^{st}$ Annual San Antonio Breast Cancer Symposium, Dec. 10-14, 2008, San Antonio, TX, USA (Poster 1074).
Eli, L. et al., "Development of novel-proximity-based immunoassays for activated HER1, HER2, HER1-HER2 heterodimers in formalin-fixed, paraffin-embedded (FFPE) cells," 2008 Eur. J. Cancer 6(Oct. 12):30 (Abstract 88).
Eli, L. et al., "Development of novel-proximity-based immunoassays for activated HER1, HER2, HER1-HER2 heterodimers in formalin-fixed, paraffin-embedded (FFPE) cells," International Conference on Molecular Targets and Cancer Therapeutics, AACR-NCI-EORTC, Oct. 21-24, 2008, Geneva, Switzerland (Poster 88).
Joensuu, H. et al., "Quantitative measurement of HER2 expression and HER2 homodimer using a novel proximity based assay: comparison with HER2 status by immunohistochemistry and chromogenic in situ hybridization in the FinHer study," Cancer Research, Jan. 15, 2009, 69(2 Suppl. 1): Abstract 2071.
Joensuu, H. et al., "Quantitative measurement of HER2 expression and HER2 homodimer using a novel proximity based assay: comparison with HER2 status by immunohistochemistry and chromogenic in situ hybridization in the FinHer study," 31$^{st}$ Annual San Antonio Breast Cancer Symposium, Dec. 10-14, 2008, San Antonio, TX, USA (Poster 2071).
Lipton, A. et al., "HER2 protein expression predicts response to trastuzumab in FISH-positive patients," Cancer Research, Jan. 15, 2009, 69(2 Suppl. 1): Abstract 32.
Lipton, A. et al., "HER2 protein expression predicts response to trastuzumab in FISH-positive patients," 31$^{st}$ Annual San Antonio Breast Cancer Symposium, Dec. 10-14, 2008, San Antonio, TX, USA (Oral Presentation 32).
Leitzel K., et al., "Use of total HER2 and HER2 homodimer levels to predict response to trastuzumab," J. Clin. Oncol. 2008 (May 20 Suppl.): Abstract 1002.
Leitzel, K. et al., "Total HER2 and HER2 homodimer levels predict response to trastuzumab," American Society of Clinical Oncology (ASCO) Annual Meeting, May 30-Jun. 3, 2008, Chicago, OL (Oral Presentation 1002).
Mukherjee, A. et al., "Proximity-based assays for the detection of activated HER3, HER2/3 heterodimers and HER3/PI3K complexes in FFPE cell line controls and tumors," Cancer Research, Jan. 15, 2009, 69(2 Suppl. 1): Abstract 4040.
Mukherjee, A. et al., "Proximity-based assays for the detection of activated HER3, HER2/3 heterodimers and HER3/PI3K complexes in FFPE cell line controls and tumors," 31$^{st}$ Annual San Antonio Breast Cancer Symposium, Dec. 10-14, 2008, San Antonio, TX, USA (Poster 4040).
Shi, Y. et al., "Development of highly quantitative, sensitive, and reproducible assays for the detection of EGFR/HER1 and ErbB3/HER3 in in formalin-fixed, paraffin-embedded cells," 2008 Eur. J. Cancer 6(Oct. 12):34-35 (Abstract 103).
Shi, Y. et al., "Development of highly quantitative, sensitive, and reproducible assays for the detection of EGFR/HER1 and ErbB3/HER3 in in formalin-fixed, paraffin-embedded cells," International Conference on Molecular Targets and Cancer Therapeutics, AACR-NCI-EORTC, Oct. 21-24, 2008, Geneva, Switzerland, Poster 103.
Bates, M.P. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," 2007 J. Clin. Oncol. 25(18S) (Jun. 20 Suppl.): Abstract 10557.
Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," American Society of Clinical Oncology (ASCO) Annual Meeting, Jun. 2-5, 2007, Chicago, IL (Poster 10557).
Hameed, M.R. et al., "The ERB family receptor dimerization in glioblastoma—An eTag assay analysis of 23 cases," 2006 J. Clin. Oncol. 24(18S) (Jun. 20 Suppl.): Abstract 1582.
Hameed, M.R. et al., "The ERB family receptor dimerization in glioblastoma—An eTag assay analysis of 23 cases," American Society of Cancer Oncology (ASCO) Annual Meeting, Jun. 2-6, 2006, Atlanta, GA (Poster 1582).
Jimeno, A. et al., "Combined targeted therapy shows increased efficacy in a novel in vivo pancreas cancer model," American Association for Cancer Research (AACR) Annual Meeting, Apr. 1-6, 2006, Washington, D.C. (Abstract 2181).
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA: Abstract A121.
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA (Poster A121).
Shi, Y., "Analysis of ErbB/HER receptor pathways in formalin-fixed and paraffin-embedded cancer cell lines using multiplexed eTag™ assays," 2005 J. Clin. Oncol. 23(16S) (Jun. 1 Suppl.): Abstract 9565.
Shi, Y.. et al., "Analysis of ErbB/HER receptor pathways in formalin-fixed and paraffin-embedded cancer cell lines using multiplexed eTag™ assays," American Society of Clinical Oncology (ASCO) Annual Meeting, May 13-17, 2007, Orlando, FL (Poster 9565).
Mukherjee, A., "The Use of ErbB/HER Activation Status as Prognostic Markers in Breast Cancer Patients Treated with Trastuzumab," 2005 J. Clin. Oncol. 23(16S) (Jun. 1 Suppl.): Abstract 553.
Mukherjee, A. et al., "The use of ErbB activation Status as Prognostic Markers in Breast Cancer Patients Treated with Trastuzumab," American Society of Clinical Oncology (ASCO) Annual Meeting, May 13-17, 2005, Orlando, FL (Poster 553).
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA: Abstract A127.
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA (Poster A127).
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA: Abstract A124.
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA (Poster A124).
Salimi-Moosavi, H. et al., "IC50 determination for receptor-targeted compounds and downstream signaling," In: Proc. Am. Assoc. Cancer Res. AACR, Apr. 16-20, 2005, Anaheim, CA: Abstract 4567.
Shi, Y. et al., "Multiplexed assay for assessing ErbB/HER receptor pathways in formalin-fixed and paraffin-embedded cancer cell lines," In: Proc. Am. Assoc. Cancer Res. AACR Apr. 16-20, 2005 Anaheim, CA: Abstract 5762.
Shi, Y. et al., "Multiplexed assay for assessing ErbB/HER receptor pathways in formalin-fixed and paraffin-embedded cancer cell lines," American Association for Cancer Research (AACR) Annual Meeting, Apr. 16-20, 2005, Anaheim, CA (Poster 5762).

(56) References Cited

OTHER PUBLICATIONS

Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA: Abstract B17.

Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA (Poster B17).

Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK (Poster 1025).

Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA: Abstract A123.

Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA (Poster A123).

Duchnowska, R. et al., "Correlation between quantitative HER2 protein expression and risk of brain metastasis in HER2-positive advanced breast cancer patients receiving trastuzumab-containing therapy," Oncologist 17(1):26-35 (2012) (pub. online Jan. 10, 2012).

Han, S-W, "Correlation of HER2, p95HER2 and HER3 expression and treatment outcome of lapatinib plus capecitabine in HER2-positive metastatic breast cancer," PLoS One 7(7):e39943 (2012) (pub. online Jul. 27, 2012).

Bates, M. et al., "Identification of a Subpopulation of Metastatic Breast Cancer Patients with Very High HER2 Expression Levels and Possible resistance to Trastuzumab," Ann. Oncol., 22(9):2014-2020 (2011) (pub. online Feb. 11, 2011).

DeFazio-Eli, L. et al., "Quantitative assays for the measurement of HER1-HER2 heterodimerization and phosphorylation in cell lines and breast tumors: applications for diagnostics and targeted drug mechanism of action," Breast Canc. Res. 13:R44 (2011) (pub. Apr. 15, 2011).

Dua, R. et al., "Detetion of hepatocyte growth factor (HGF) ligand-C-met receptor activation in formalin-fixed, paraffin-embedded specimens by a novel proximity assay," PLoS One 6(1): e15932 (2011) (pub. online Jan. 21, 2011).

Joensuu, H. et al., "Very high quantitative tumor HER2 content and outcome in early breast cancer," Ann. Oncol. 22(9): 2007-2013 (2011) (pub. online Feb. 1, 2011).

Ghosh, M. et al., "Trastuzumab has preferential activity against breast cancers driven by HER2 homodimers," Cancer Res. 71(5):1871 (2011) (pub. online Feb. 15, 2011).

Mukherjee, A. et al., "Profiling the HER3/PI3K Pathway in Breast Tumors Using Proximity-Directed Assays Identifies Correlations between Protein Complexes and Phosphoproteins," PLoS One 6(1): e16443 (2011) (pub. online Jan. 28, 2011).

Dua, R. et al., "EGFR over-expression and activation in high HER2, ER negative breast cancer cell lines induces trastuzumab resistance," Breast Cancer Res. Treat. 122(3):6850697 (2010) (pub. online Oct. 27, 2009).

Jain, A. et al., "HER kinase axis receptor dimer partner switching occurs in response to EGFR tyrosine kinase inhibition despite failure to block cellular proliferation," Cancer Res. 70(5):1989-1999 (2010) (pub. online Feb. 16, 2010).

Huang, Q. et al., "Comparison of central HER2 testing with quantitative total HER2 expression and HER2 homodimer measurement using a novel proximity based assay," Am. J. Clin. Pathol. 134:303-311 (2010) (pub. Aug. 2010).

Larson, J.S. et al., "Analystical validation of a highly senstivie, accurate, and reproducible assay (HERmark®) for the measurement of HER2 total protein and HER2 homodimers in FFPE breast cancer tumor specimens," Pathol. Res. Intl, 2010: Article ID 814176 (2010) (pub. online Jun. 28, 2010).

Lipton, A. et al., "Quantitative HER2 protein levels predict outcome in fluorescence in situ hybridization-positive patients with metastatic breast cancer treated with trastuzumab," Cancer 116:5168-5178 (2010) (pub. online Nov. 3, 2010).

Mamluk, R. et al., "Anti-tumor effect of CT-322 as an adnectin inhibitor of vascular endothelial growth factor receptor-2," MAbs 2(2):199-208 (2010) (pub. online Mar. 1, 2010).

Sperinde, J. et al., "Quantitation of p95HER2 in paraffin sections by using a p95-specific antibody and correlation with outcome in a cohort of trastuzumab-treated breast cancer patients," Clin. Canc. Res. 16(16):4226-4235 (2010) (pub. online Jul. 27, 2010).

Toi, M. et al., "Differential survival following trastuzumab treatment based on quantitative HER2 expression and HER2 homodimers in a clinic-based cohort of patients with metastatic breast cancer," BMC Cancer 10:56 (2010) (pub. Feb. 23, 2010) (10 pages).

Desmedt, C. et al., "Quantitation of HER2 expression or HER2:HER2 dimers and differential survival in a cohort of metastatic breast cancer patients carefully selected for trastuzumab treatment primarily by FISH," Diagn. Mol. Pathol. 18(1):22-29 (2009) (pub. Mar. 2009).

Shi, Y. et al., "A novel proximity assay for the detection of proteins and protein complexes: quantitation of HER1 and HER2 total protein expression and homodimerization in formalin-fixed, paraffin-embedded cell lines and breast cancer tissue," Diagn. Mol. Pathol. 18(1):11-21 (2009) (pub. Mar. 2009).

Chan-Hui, P-Y et al., "Applications of eTag™ assay platform to systems biology approaches in molecular oncology and toxicology studies," Clin. Immun. 111:162-174 (2004) (pub. online Mar. 11, 2004).

Tian, H. et al., "Multiplex mRNA assay using electrophoretic tags for high-throughput gene expression analysis," Nucl. Acid Res. 32(16):e126 (pub. online Sep. 8, 2004).

Arribas, J. et al., "HER2 Fragmentation and Breast Cancer Stratification," Clin. Cancer Res. 16(16):4071-4073 (2010).

Arribas, J. et al., "p97HER2 and Breast Cancer," Cancer Res. 71(5):1-5 (2011).

Bacus, S. et al., "The expression of HER B receptors and their ligands as predicting factors for response to chemotherapy," European J. Cancer 36(5):Abstract S103 (2000).

Baselga, J., "Herceptin® Alone or in Combination with Chemotherapy in the Treatment of HER2-Positive Metastatic Breast Cancer: Pivotal Trials," Oncology 61(supp 2):14-21 (2001).

Buck, E. et al., "Inactivation of Akt by the epidermal growth factor receptor inhibitor erlotinib is mediated by HER-3 in pancreatic and colorectal tumor cell lines and contributes to erlotinib sensitivity," Mol. Cancer Ther. 5(8):2051-2059 (2006).

Christianson, T. et al., "NH2-terminally Truncated HER 2/neu Protein: Relationship with Shedding of the Extracellular Domain and with Prognostic Factors in Breast Cancer," Cancer Res. 58:5123-5129 (1998).

Frolov, A. et al., "ErbB3 Expression and Dimerization with EGFR Influence Pancreatic Cancer Cell Sensitivity to Erlotinib," Cancer Biol. Ther. 6(4):e1-e7 (2007).

Fuchs, B. et al., "Epithelial-to-Mesenchymal Transition and Integrin-Linked Kinase Mediate Sensitivity to Epidermal Growth Factor Receptor Inhibition in Human Hepatoma Cells," Cancer Res. 68:2391-2399 (2008).

Hamburger, A., "The Role of ErbB3 and its Binding Partners in Breast Cancer Progression and Resistance to Hormone and Tyrosine Kinase Directed Therapies," J. Mammary Gland Biol. Neoplasia, 13:225-233 (2008).

Harris, J. and Chess, R., "Effect of Pegylation on Pharmaceuticals," Nat. Rev. Drug Discov. 2:214-221 (2003).

"HER3/ErbB3 (1B2) Rabbit mAb," Apr. 2, 2010, XP055072082, retrieved from the Internet: URL:http://www.cellsignal.com/pdf/4754 (retrieved on Jul. 19, 2013).

(56) References Cited

OTHER PUBLICATIONS

Jahanzeb, M., "Trastuzumab-Based Combinations in metastatic Breast Cancer: How to Make a Choice," Clin. Breast Cancer, 4(1):28-38 (2003).
Knowlden, J.M. et al., "c-erbB3 and c-erbB4 expression is a feature of the endocrine responsive phenotype in clinical breast cancer," Oncogene 17:1949-1957 (1998).
"Mouse (monoclonal) anti-ErbB3/Her3 (C-terminus) Product Analysis Sheet," Nov. 1, 2008, XP055072081, retrieved from the Internet: URL:http//userimg.fantibody.com/files/ts/dixfile/2013-05/29/15/feSxnJ4wJXnFFnWz.pdf (retrieved on Jul. 19, 2013).
Ning, L., "Recent advances of dual tyrosine kinases inhibitor lapatinib in breast cancer therapy," J. Intl. Oncol. 34(5):362-365 (2007).
Prigent, S. et al., "Expression of the c-cerb-3 protein in normal human adult and fetal tissues," Oncogene 7(7):1273-1278 (1992).
Rajkumar, T. et al., "Expression of the c-erbB-3 protein in gastrointestinal tract tumours determined by monoclonal antibody RTJI," J. Pathol. 170(3):271-278 (1993).
Reschke, M. et al., "HER3 is a determinant for poor prognosis in melanoma," Clin. Cancer Res. 14(16):5188-5197 (2008).
Winslow J. et al., "Characterization of a novel proximity immunoassay for the quantitative determination of HER2 protein expression and HER2 homodimerization in formalin-fixed, paraffin-embedded breast cancer tissue," Breast Cancer Research and Treatment, Dec. 13, 2007, 106(1):S88.
Canadian Patent Application No. 2,711,843, Office Action, dated Nov. 8, 2013.
Chinese Patent Application No. 201080009544.4, Office Action, dated Sep. 26, 2013.
Chinese Patent Application No. 201080009544.4, Office Action, dated Jun. 19, 2014.
Chinese Patent Application No. 201080009543.X, Office Action, dated Jun. 24, 2014.
European Patent Application No. 10732178.8, Extended European Search Report, dated Aug. 28, 2012.
European Patent Application No. 09831007.1, Supplemental Search Report, dated Mar. 6, 2013.
European Patent Application No. 09831007.1, Examination Report, dated Feb. 17, 2014.
European Patent Application No. 10732178.8, Examination Report, dated Mar. 10, 2014.
European Patent Application No. 10732178.8, Office Action dated Feb. 27, 2013.
Intl. Application No. PCT/EP2009/056976, International Search Report, dated Dec. 12, 2009.
Israel Patent Application No. 216731, Office Action, dated Jul. 30, 2014.
Israel Patent Application No. 216731, Office Action, dated Jan. 29, 2014.
Israel Patent Application No. 216731, Office Action, dated Feb. 24, 2013.
Japanese Patent Application No. 2011-546408, Office Action, dated Jul. 18, 2013.
Singapore Patent Application No. 2011092582, Written Opinion, dated Sep. 22, 2014.
Singapore Patent Application No. 2011092582, Written Opinion, dated May 30, 2013.
Singapore Patent Application No. 201105100-0, Examination Report, dated Mar. 4, 2013.
Singapore Patent Application No. 201105100-0, Written Opinion, dated Jun. 15, 2012.
U.S. Appl. No. 13/911,329, Office Action, dated Oct. 16, 2014.
International Application No. PCT/EP2009/056976, International Search Report Dated Dec. 7, 2009.
Fornier, M. et al., "Serum HER2 extracellular domain in metastatic breast cancer patients treated with weekly trastuzumab and paclitaxel: association with HER2 status by immunohistochemistry and fluorescence in situ hybridization and with response rate," Annals of Oncol. 16:234-239 (2005).
Kostler, W. et al., "Monitoring of Serum Her-2/neu Predicts Response and Progression-Free Survival to Trastuzumab-Based Treatment in Patients with Metastatic Breast Cancer," Clinical Cancer Res. 10:1618-1624 (2004).
Smith, B. et al., "The efficacy of Herceptin therapies is influenced by the expression of other erbB receptors, their ligands and the activation of downstream signaling proteins," British J. Cancer 91:1190-1194 (2004).
Canadian Patent Application No. 2,711,843, Office Action, dated Aug. 13, 2015.
Canadian Patent Application No. 2,764,386, Office Action, dated Jul. 9, 2015.
U.S. Appl. No. 12/688,766, Office Action dated Apr. 3, 2014.
U.S. Appl. No. 12/688,766, Office Action dated Mar. 27, 2013.
U.S. Appl. No. 12/688,766, Office Action dated Jul. 10, 2012.
U.S. Appl. No. 14/322,317, Office Action, dated Dec. 16, 2015.
Canada Patent Application No. 2,711,843, Office Action, dated Jun. 27, 2016.

* cited by examiner

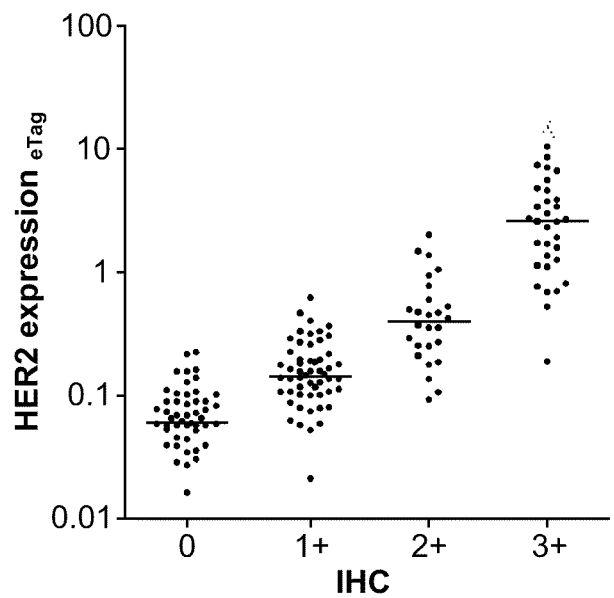
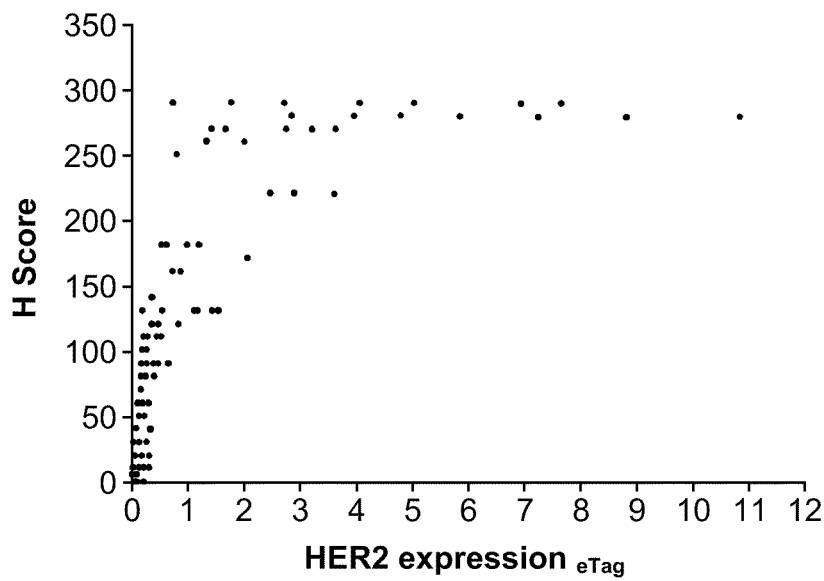
FIG. 6

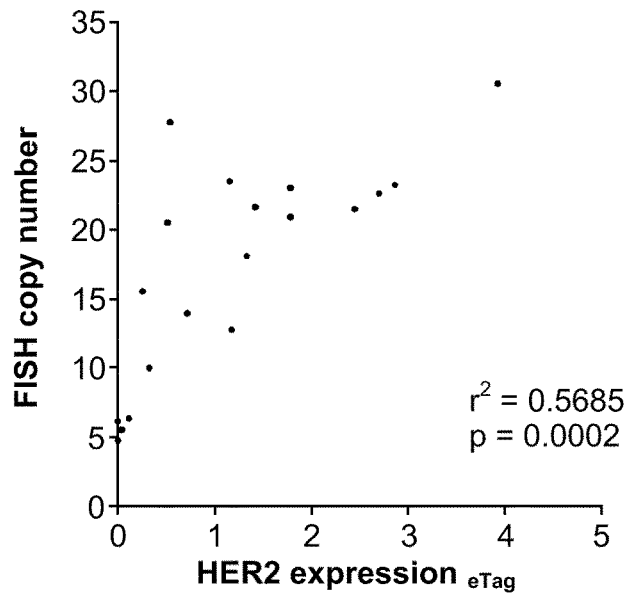
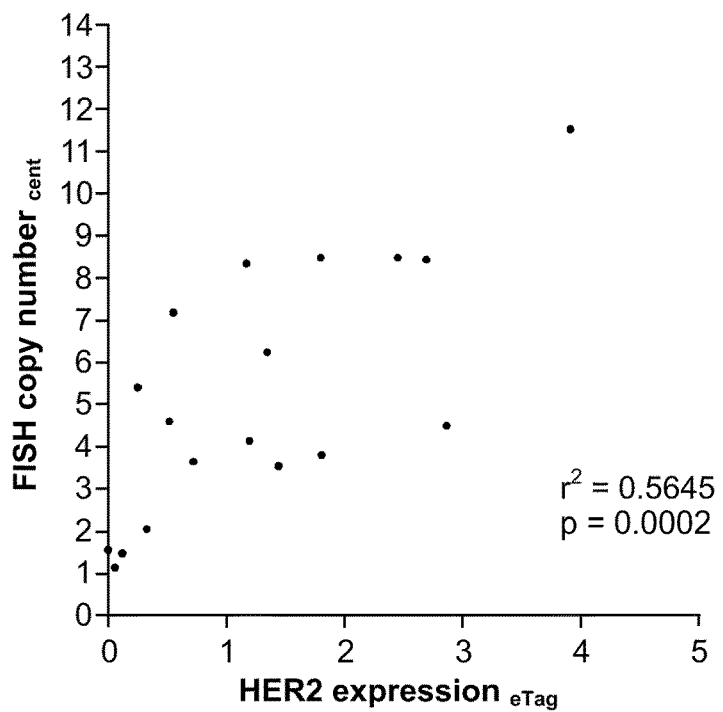
FIG. 7A a)
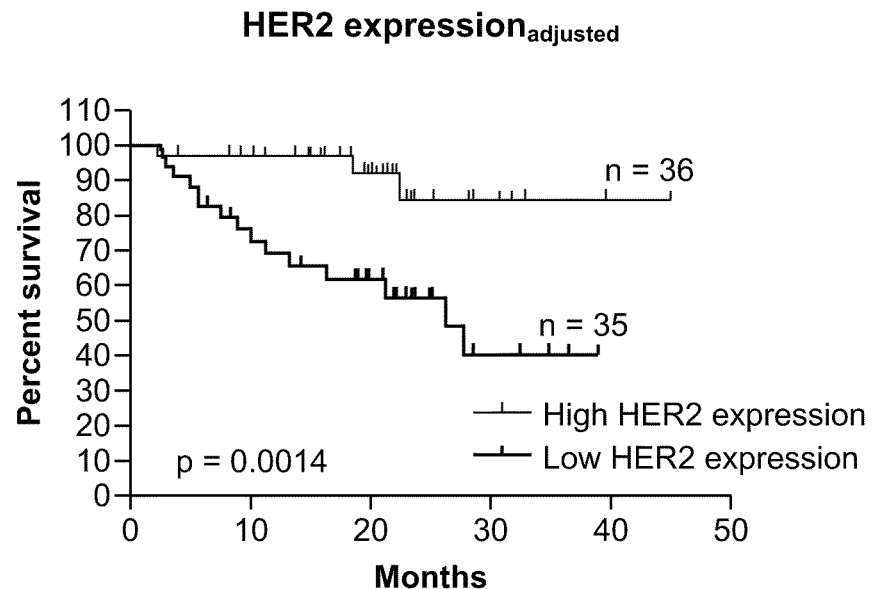
b)
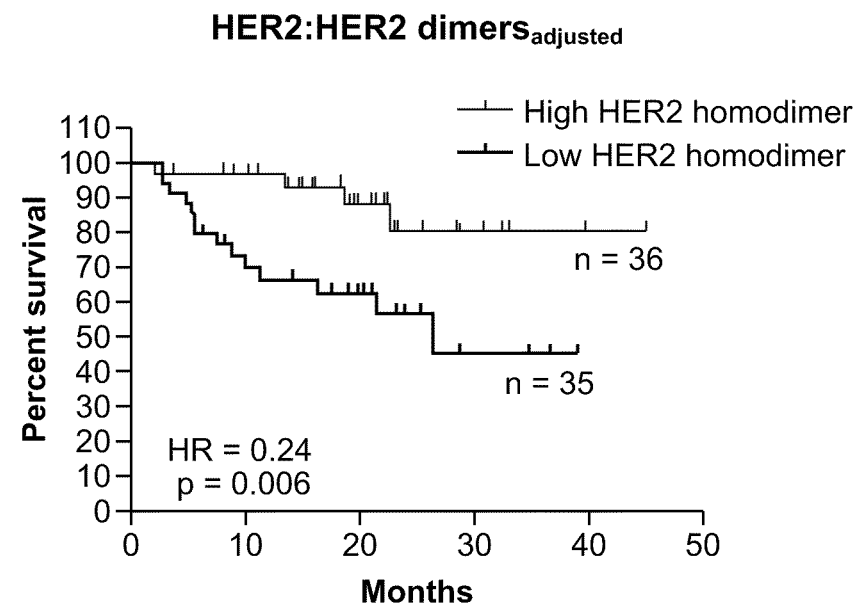
FIG. 10 a)
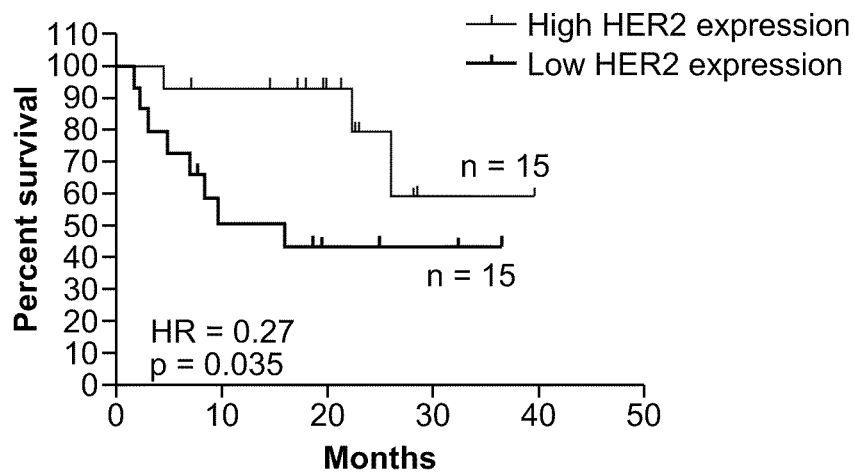
b)
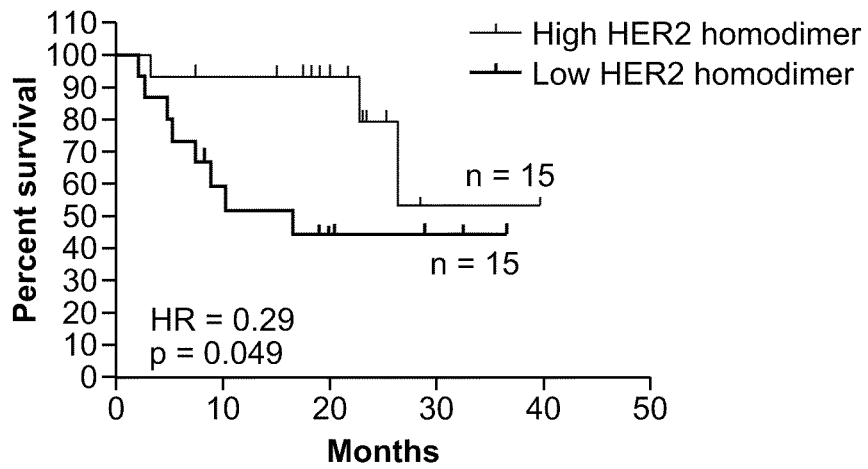
FIG. 11

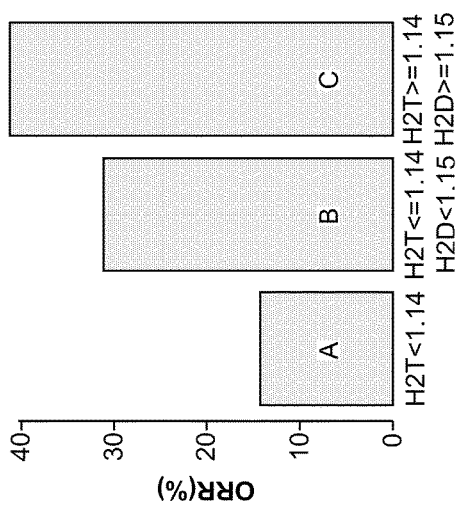
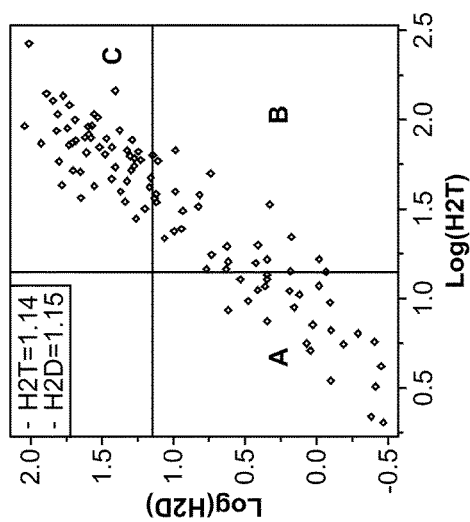
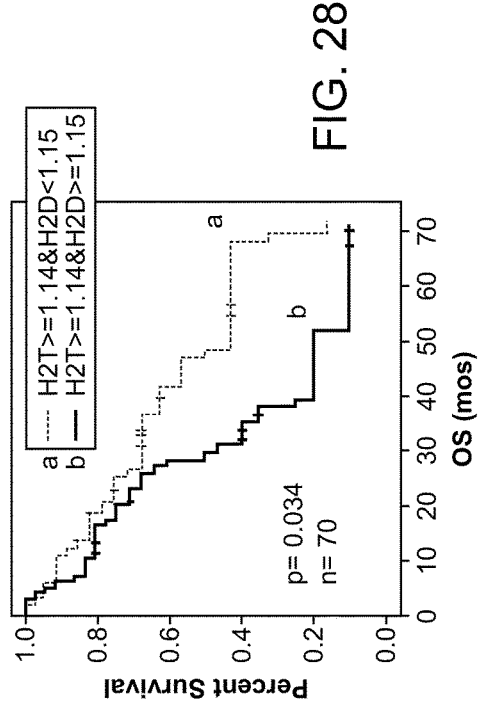
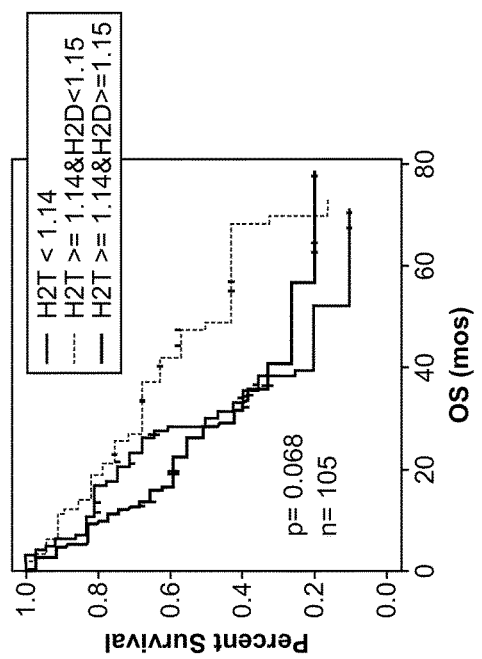
FIG. 28

| Cohort characteristics ||
|---|---|
| Characteristic | Number (range, %) |
| Total patients | 103 |
| Mean follow-up (months) | 34.3 (1 1.8-77.9) |
| Mean age | 55.3 (27.6-85.4) |
| H2T (> cutoff) | 70 (69) |
| H2D (> cutoff) | 68 (67) |
| Number of metastatic sites | |
| < 3 | 61 (59) |
| ≥ 3 | 42 (41) |
| Hormonal status | |
| ER+ PR+ | 35 (34) |
| ER+ PR- | 2 (2) |
| ER- PR+ | 3 (3) |
| ER- PR- | 61 (59) |
| unknown | 2 (2) |
| HER2 status | |
| 2+ | 5 |
| FISH+ | 5 |
| 3+ | 96 |
| FISH+ | 70 |
| FISH- | 22 |
| FISH unknown | 4 |
| Unknown | 2 |
| FISH+ | 2 |
| Treatment | |
| trastuzumab + chemotherapy | 91 (88) |
| trastuzumab only | 12 (12) |
| Line of chemotherapy | |
| First line | 76 (74) |
| Second line | 17 (17) |
| Third line | 8 (7) |
| Unknown | 2 (2) |

Table 1

FIG. 29

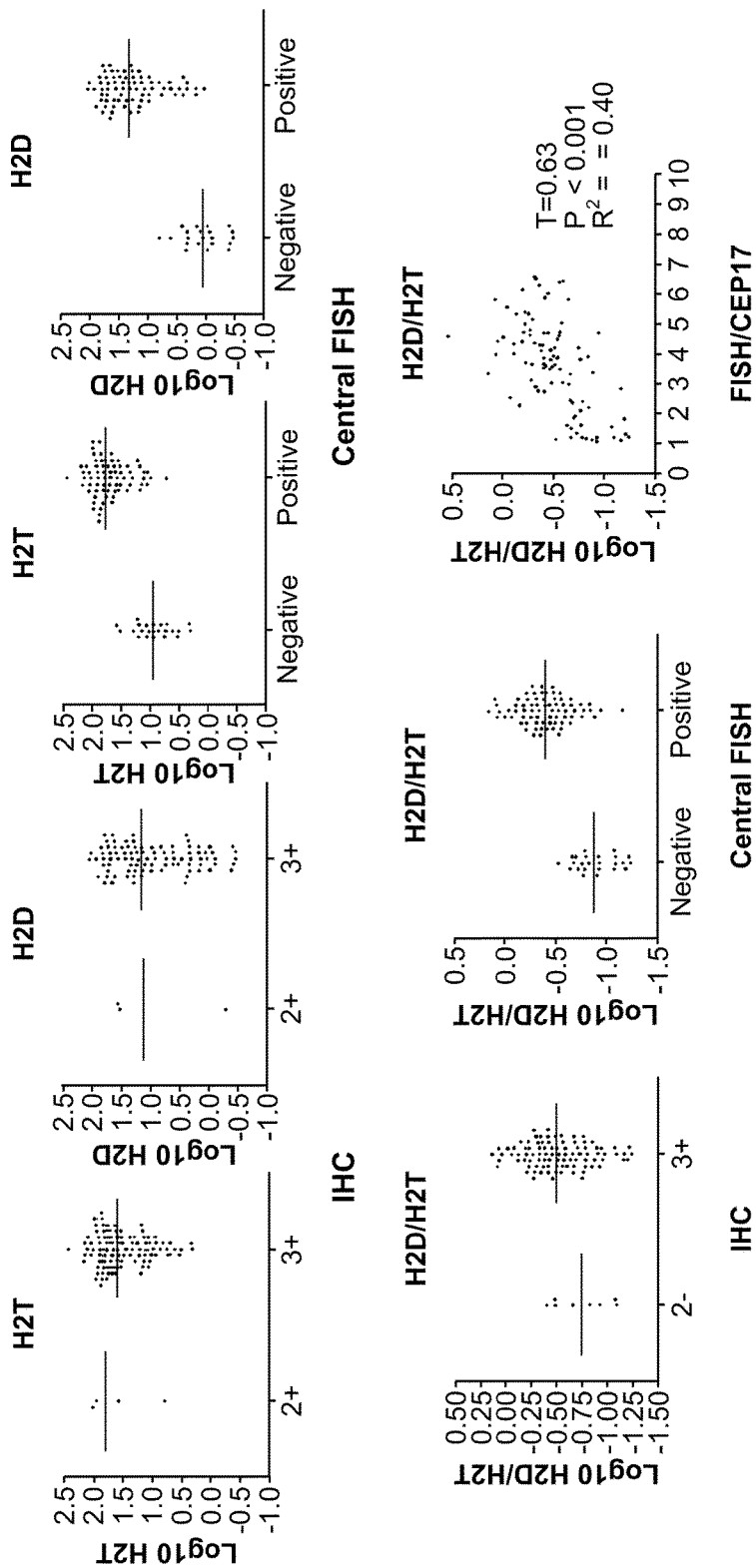

Figure A: H2T, H2D and H2D/H2T distributions by IHC and FISH

The HERmark measurements span a dynamic range of 2-2.5 logs in patient samples assessed as 3+ by IHC. There is a correlation between central FISH and H2T or H2D, but there is overlap between the distributions suggesting discordant calls for some patients. There is a significant correlation between H2T and FISH/CEP17 copy number, but for any given FISH/CEP17 value, there is approximately a 10-50 fold range of H2T values.

FIG. 29A

Figure B: Kaplan Meier analyses examining disease-free survival in adjuvant setting by tertiles of H2T, H2D, or H2D/H2T.

HER2 expression did not correlate with DFS, but variables incorporating a measurement of HER2 homodimers demonstrated an association between low H2D/H2T or H2D and longer DFS.

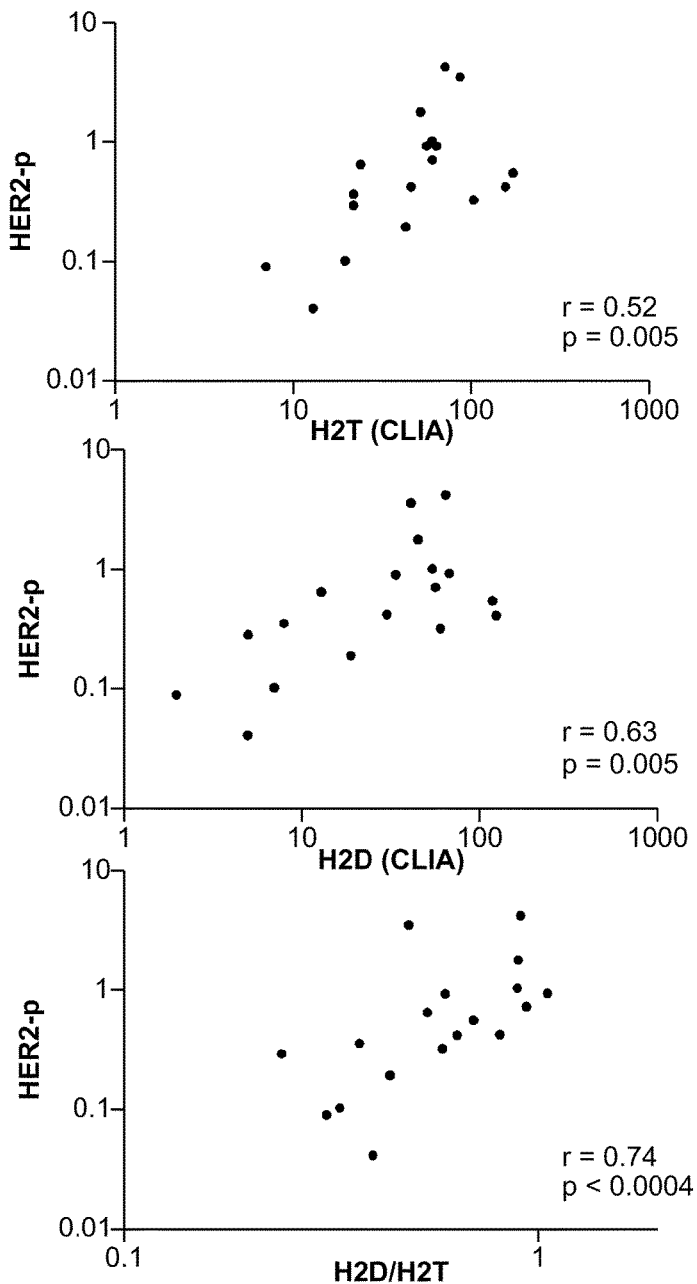

Figure C: Correlation of H2T, H2D, and H2D/H2T with HER2-phospho measurements by VeraTag in FFPE breast tumor control specimens.
18 breast tumors were obtained in the fresh frozen state and carefully prepared as formalin-fixed, paraffin-embedded specimens. Using the VeraTag assay, H2T, H2D, and the phosphorylated form of HER2 were measured and correlated.
All correlations were significant.

FIG. 29C

| Cox proportional hazards multivariate analysis, entire cohort (N=103) | | | | | | |
|---|---|---|---|---|---|---|
| TTP | without H2T or H2D | | with H2T | | with H2D | |
| variable | hazard ratio | p-value | hazard ratio | p-value | hazard ratio | p-value |
| number of metastatic sites (3 vs. <3) | 3.1 | <0.001 | 3.4 | <0.001 | 3.3 | <0.001 |
| skin metastasis (yes vs. no) | 2.1 | 0.013 | 2 | 0.015 | 2 | 0.014 |
| FISH (positive vs. negative) | 0.52 | 0.02 | 1.1 | 0.8 | 0.92 | 0.8 |
| H2T (vs. < cutoff) | - | - | 0.39 | 0.016 | - | - |
| H2D (vs. < cutoff) | - | - | - | - | 0.53 | 0.092 |
| OS | without H2T or H2D | | with H2T | | with H2D | |
| variable | hazard ratio | p-value | hazard ratio | p-value | hazard ratio | p-value |
| age | 0.97 | 0.048 | 0.97 | 0.021 | 0.97 | 0.024 |
| number of metastatic sites (3 vs. <3) | 1.6 | <0.001 | 1.6 | <0.001 | 1.6 | <0.001 |
| ER status (positive vs. negative) | 0.49 | 0.03 | 0.48 | 0.03 | 0.51 | 0.039 |
| FISH status (positive vs. negative) | 0.65 | 0.23 | 1.4 | 0.57 | 1.6 | 0.36 |
| H2T (vs. < cutoff) | - | - | 0.4 | 0.058 | - | - |
| H2D (vs. < cutoff) | - | - | - | - | 0.35 | 0.026 |

| Cox proportional hazards multivariate analysis: FISH-positive patients only (N=77) | | |
|---|---|---|
| TTP variable | hazard ratio | p-value |
| number of metastatic sites (3 vs. <3) | 33 | <0.001 |
| H2T (vs. < cutoff) | 0.29 | 0.0015 |
| Line of therapy (more vs. less) | 1.7 | 0.011 |
| time from sample to trastuzumab therapy (more vs. less) | 0.99 | 0.045 |
| model p-value 0.001 | | |
| OS variable | hazard ratio | p-value |
| number of metastatic sites (3 vs. <3) | 6.8 | <0.001 |
| H2T (vs. < cutoff) | 0.37 | 0.02 |
| Axiliary mets (absent vs. present) | 0.33 | 0.03 |
| time from sample to trastuzumab therapy (more vs. less) | 0.97 | 0.02 |

Table 1

Lipton: Cox multivariate Models of TTP and OS

FIG. 30

Multivariate Cox proportional hazards analyses

| | TDR | | TAR | | TD | |
|---|---|---|---|---|---|---|
| | HR | p-value | HR | p-value | HR | p-value |
| Herceptin vs. control | 0.61 | 0.09 | 0.81 | 0.42 | 0.56 | 0.12 |
| H2T continuous | 1 | 0.58 | 1 | 0.73 | 1 | 0.87 |
| Herceptin vs. control | 0.61 | 0.08 | 0.8 | 0.41 | 0.55 | 0.12 |
| H2D continuous | 1 | 0.8 | 1 | 0.57 | 1 | 0.93 |
| Herceptin vs. control | 0.57 | 0.05 | 0.76 | 0.3 | 0.53 | 0.09 |
| H2D/H2T continuous | 0.37 | 0.07 | 0.38 | 0.05 | 0.45 | 0.25 |

Table 3

FIG. 39

HER2 DIAGNOSTIC METHODS

This application claims the benefit of and priority under 35 USC § 119(e) to U.S. Provisional Application No. 61/015,608, filed Dec. 20, 2007, U.S. Provisional Application No. 61/121,480, filed Dec. 10, 2008, and U.S. Provisional Application No. 61/121,817, filed Dec. 11, 2008, which are incorporated by reference in their entirety.

FIELD OF THE INVENTION

The present invention provides methods for determining whether a Her-2 positive cancer is likely to respond to treatment with a Her2-acting agent, particularly trastuzumab. The present invention is also drawn to methods for determining whether a subject with a Her-2 positive cancer is unlikely to respond to treatment with at least one chemotherapeutic agent, particularly paclitaxel, in addition to the Her2-acting agent. The present method is also drawn to a method for predicting a time course of disease or the probability of a significant event in the time course of disease in a subject with a Her-2 positive cancer.

BACKGROUND OF THE INVENTION

A biomarker is generally a characteristic that is objectively measured and evaluated as an indicator of normal biological processes, pathogenic processes or pharmacological responses to a therapeutic intervention. See Atkinson et al., 2001, *Clin. Pharmacol. Ther.* 69:89-95. Biomarkers vary widely in nature, ease of measurement and correlation with physiological states of interest. See, e.g., Frank et al., 2003, *Nature Reviews Drug Discovery* 2:566-580. It is widely believed that the development of new validated biomarkers will lead both to significant reductions in healthcare and drug development costs and to significant improvements in treatment for a wide variety of diseases and conditions. Thus, a great deal of effort has been directed to using new technologies to find new classes of biomarkers. See, e.g., Petricoin et al., 2002, *Nature Reviews Drug Discovery*, 1:683-695; and Sidransky, 2002, *Nature Reviews Cancer* 2:210-219.

The interactions of cell surface membrane components play crucial roles in transmitting extracellular signals to a cell in normal physiology and in disease conditions. In particular, many types of cell surface receptors undergo dimerization, oligomerization or clustering in connection with the transduction of an extracellular event or signal into a cellular response, such as, e.g., proliferation, increased or decreased gene expression or the like. See, e.g., George et al., 2002, *Nature Reviews Drug Discovery* 1:808-820; Mellado et al, 2001, *Ann. Rev. Immunol.* 19:397-421; Schlessinger, 2000, *Cell* 103:211-225; and Yarden, 2001, *Eur. J. Cancer* 37:S3-S8. The role of such events in diseases, such as cancer, has been the object of intense research and has led to the development of several new drugs and drug candidates. See, e.g., Herbst and Shin, 2002, *Cancer* 94:1593-1611; Yarden and Sliwkowski, 2001, *Nature Reviews Molecular Cell Biology* 2:127-137; McCormick, 1999, *Trends in Cell Biology* 9:53-56 (1999); and Blume-Jensen and Hunter, 2001, *Nature* 411:355-365.

Expression levels of individual cell surface receptors, such as Her-2, have been used as biomarkers. Conventional immunohistochemical (IHC) or fluorescence in situ hybridization (FISH) analysis has been used to detect Her-2 overexpression to determine whether treatment with a Her2-acting agent, e.g., trastuzumab, is warranted. Also, U.S. Pat. No. 4,968,603 describes Her-2 expression as a cancer biomarker. However, in two different studies, only 20% or 35% of patients overexpressing Her-2 objectively responded to trastuzumab treatment. See Baselga et al., 1996, *J. Clin. Oncol.* 14:737-44; Cobleigh et al., 1999, *J. Clin. Oncol.* 17:2639-48; and Vogel et al., 2002, *J. Clin. Oncol.* 20:719-26. Further, in other studies of the combination of trastuzumab plus chemotherapy in the metastatic breast cancer setting, only approximately 50% of patients overexpressing Her-2 objectively responded to trastuzumab combination therapy. See Slamon et al. *N Engl J Med* 344: 783-92.

At the current time, there is no method that can reliably determine whether a subject with a cancer is likely or unlikely to respond to treatment with a Her-2-acting agent, such as trastuzumab. Such a method may be used to identify patients unlikely to respond to trastuzumab and avoid providing costly treatment to those patients. Such an assay may also be used to identify patients that are unlikely to respond to a chemotherapeutic agent in addition to the Her-2 acting agent thus allowing the subject to avoid the potentially toxic effects of the chemotherapeutic agent. Such a method may also be used to predict a time course of disease or a probability of a significant event in the disease for Her-2 positive patients.

SUMMARY OF THE INVENTION

The invention provides a method for determining whether a subject with a cancer is likely to respond to treatment with a Her2-acting agent and/or for predicting a time course of disease and/or a probability of a significant event in the time course of disease in a subject with a cancer. In certain embodiments, the methods comprise detecting a biomarker or combination of biomarkers associated with responsiveness to treatment with a Her2-acting agent as described hereinafter, and determining whether the subject is likely to respond to treatment with the Her2-acting agent. In certain embodiments, the methods comprise detecting a biomarker or combination of biomarkers and predicting a time course associated with progression of disease or a probability of a significant event in the time course of disease in a subject with cancer.

In one aspect, the invention is drawn to a method for determining whether a subject with a cancer is likely to respond to treatment with a Her2-acting agent. In another aspect, the invention is drawn to a method for predicting a time course of disease. In another aspect, the method is drawn to a method for predicting a probability of a significant event in the time course of the disease.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from metastatic disease to death. In a preferred embodiment, the significant event is the progression from metastatic disease to relapse. In a preferred embodiment, the significant event is the progression from relapse to death. In certain embodiments, the time course is measured with respect to overall survival rate, time to progression and/or using the RECIST or other response criteria.

In certain embodiments, the method comprises detecting in a biological sample from the subject's cancer the amount of Her-2 and/or Her-2 homodimers wherein if the amount of Her-2 and/or Her-2 homodimers is high, then the patient is likely to respond to the Her-2 acting agent and/or the patient has a long time course. In certain embodiments, the cancer is breast cancer. In preferred embodiments, the breast cancer is metastatic. In certain embodiments, the Her-2 acting agent is trastuzumab. In certain embodiments, the method is performed with an eTag™ assay. In certain embodiments, likeliness to respond is measured with respect to overall survival rate, time to progression and/or using the RECIST or other response criteria.

In certain embodiments, a predetermined measure is created by dividing patient samples into at least two patient subgroups. In certain embodiments, the number of subgroups is two so that the patient sample is divided into a subgroup of patients whose Her-2 and/or Her-2 homodimers is high and a subgroup whose Her-2 and/or Her-2 homodimers is low. In certain embodiments, the amount of Her-2 and/or Her-2 homodimers in the subject are compared to either the high subgroup or the low subgroup; if the amount of Her-2 and/or Her-2 homodimers in the patient are high, then the patient is likely to respond to a Her-2 acting agent and/or the patient is likely to have a long time course. In certain embodiments, the number of subgroups is greater than two, including, without limitation, three subgroups, four subgroups, five subgroups and six subgroups. In certain embodiments, likeliness to respond is measured with respect to overall survival rate, time to progression and/or using the RECIST or other response criteria. In certain preferred embodiments, the Her-2 acting agent is trastuzumab.

In certain embodiments, the predetermined measure is an optimal cutoff. Such optimal cutoffs are disclosed herein, and certain embodiments of the invention are meant to include amounts that are approximate to the amounts mentioned and disclosed herein. In certain embodiments, the amount of Her-2 and/or Her-2 homodimers in the subject are compared to the optimal cutoff; if the amount of Her-2 and/or Her-2 homodimers in the patient are high, then the patient is likely to respond to a Her-2 acting agent and/or the patient's time course is likely to be long. In another embodiment, if the amount of Her-2 is high, then the patient is likely to respond to a Her-2 acting agent and/or the time course is likely to be long. In another embodiment, if the amount of Her-2 is high, and the amount of Her-2 homodimers and/or the ratio of Her-2 homodimers to Her-2 are low, then the patient is likely to respond to a Her-2 acting agent and/or the time course is likely to be long. In another embodiment, if the amount of Her-2 is high and the amount of Her-2 dimers is high, then the patient is likely to respond to a Her-2 acting agent and/or the time course is likely to be long.

In another aspect, the invention is drawn to a method for determining whether a subject with a Her-2 positive cancer is likely to respond to treatment with a Her2-acting agent and/or the time course of the disease is long. In another aspect, the invention is drawn to a method for predicting a time course of disease in a subject with a Her-2 positive cancer. In another aspect, the invention is drawn to a method for predicting the probability of a significant event in a subject with a Her-2 positive cancer.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from metastatic disease to death. In a preferred embodiment, the significant event is the progression from metastatic disease to relapse. In a preferred embodiment, the significant event is the progression from relapse to death. In certain embodiments, the time course is measured with respect to overall survival rate, time to progression and/or using the RECIST or other response criteria.

In certain embodiments, the method comprises measuring in a biological sample from the subject's cancer an amount of Her-2 and/or Her-2 homodimers, wherein if the amount of Her-2 and/or Her-2 homodimers is high, then the patient is likely to respond to the Her-2 acting agent and/or the patient has a long time course. In certain embodiments, the biological sample comprises FFPEs. In certain embodiments, the subject's cancer is breast cancer. In certain embodiments, the breast cancer is metastatic. In certain embodiments, the Her-2 acting agent is trastuzumab. In certain embodiments, an amount of Her-2 is measured. In certain embodiments, an amount of Her-2 homodimers is measured. In certain embodiments, the amount of Her-2 homodimers is measured using an assay capable of measuring and/or quantifying an amount of protein-protein interactions in a sample. In certain embodiments, the assay is the eTag™ assay. In certain embodiments, likeliness to respond is measured with respect to overall survival rate, time to progression and/or using the RECIST or other response criteria.

In certain embodiments, a predetermined measure is created by dividing patient samples into at least two patient subgroups. In certain embodiments, the number of subgroups is two so that the patient sample is divided into a subgroup of patients whose Her-2 and/or Her-2 homodimers is high and a subgroup whose Her-2 and/or Her-2 homodimers is low; the amount of Her-2 and/or Her-2 homodimers in the subject are then compared to either the high subgroup or the low subgroup and if the amount of Her-2 and/or Her-2 homodimers in the subject are high, then the subject is likely to respond to a Her-2 acting agent and/or the patient is likely to have a long time course. In certain embodiments, the number of subgroups is greater than two, including, without limitation, three subgroups, four subgroups, five subgroups and six subgroups. In certain embodiments, likeliness to respond is measured with respect to overall survival rate, time to progression and/or using the RECIST or other response criteria. In certain preferred embodiments, the Her-2 acting agent is trastuzumab.

In certain embodiments, the predetermined measure is an optimal cutoff. Such optimal cutoffs are disclosed herein, and certain embodiments of the invention are meant to include amounts that are approximate to the amounts mentioned and disclosed herein. In certain embodiments, the amount of Her-2 and/or Her-2 homodimers in the subject are compared to the optimal cutoff; if the amount of Her-2 and/or Her-2 homodimers in the patient are high, then the patient is likely to respond to a Her-2 acting agent and/or the patient's time course is likely to be long. In another embodiment, if the amount of Her-2 is high, then the patient is likely to respond to a Her-2 acting agent and/or the time course is likely to be long. In another embodiment, if the amount of Her-2 is high, and the amount of Her-2 homodimers and/or the ratio of Her-2 homodimers to Her-2 is low, then the patient is likely to respond to a Her-2 acting agent and/or the time course is likely to be long. In another embodiment, if the amount of Her-2 is high and the amount of Her-2 homodimers and/or the ratio of Her-2 homodimers to Her-2 is high, then the patient is likely to respond to a Her-2 acting agent and/or the time course is likely to be long.

In another aspect, the invention provides a method for determining whether a subject with Her2-positive cancer is unlikely to respond to treatment with a Her2-acting agent and/or the patient is likely to have a short time course. In certain embodiments, the method comprises detecting in a biological sample from the subject's cancer the amount of Her-2, wherein if the amount of Her-2 is low, the subject is unlikely to respond to treatment with the Her2-acting agent and/or the patient is likely to have a short time course. In certain preferred embodiments, the Her2-acting agent is trastuzumab.

In another aspect, the invention is drawn to a method for determining whether a subject with a Her-2 positive cancer is unlikely to respond to treatment with at least one chemotherapeutic agent in addition to a Her2-acting agent and/or the patient is likely to have a short time course. In certain embodiments, the method comprises measuring in a biological sample from the subject's cancer an amount of Her-2 and/or Her-2 homodimers, wherein if the level of Her-2 and/or Her-2 homodimers is high, then the patient is unlikely to respond to at least one chemotherapeutic agent in addition to a Her-2 acting agent. In certain embodiments, the biological sample comprises FFPEs. In certain embodiments, the subject's cancer is breast cancer. In certain embodiments, the breast cancer is metastatic. In certain embodiments, the Her-2 acting agent is trastuzumab. In certain embodiments, the chemotherapeutic agent is paclitaxel. In certain embodiments, an amount of Her-2 is measured. In certain embodiments, an amount of Her-2 homodimers is measured. In certain embodiments, the amount of Her-2 homodimers is measured using an assay capable of measuring and/or quantifying an amount of protein-protein interactions in a sample. In certain embodiment, the assay is the eTag™ assay. In certain embodiments, likeliness to respond is measured with respect to overall survival rate, time to progression and/or using the RECIST or other response criteria.

In another aspect, the invention is drawn to a method for determining whether a subject with a Her-2 positive cancer is likely to respond to treatment with at least one chemotherapeutic agent in addition to a Her2-acting agent. In certain embodiments, the method comprises measuring in a biological sample from the subject's cancer an amount of Her-2 and/or Her-2 homodimers, wherein if the level of Her-2 and/or Her-2 homodimers is low as compared to a predetermined standard, then the patient is likely to respond to at least one chemotherapeutic agent in addition to the Her-2 acting agent. In certain embodiments, the biological sample comprises FFPEs. In certain embodiments, the subject's cancer is breast cancer. In certain embodiments, the breast cancer is metastatic. In certain embodiments, the Her-2 acting agent is trastuzumab. In certain embodiments, the chemotherapeutic agent is paclitaxel. In certain embodiments, likeliness to respond is measured with respect to overall survival rate, time to progression and/or using the RECIST criteria.

In another aspect, the invention is drawn to a method for determining whether a subject with a Her-2 positive cancer is likely to respond to a Her-2 acting agent and/or predicting whether the time course of the disease is long and/or predicting whether the subject will have a significant event, the method comprising detecting in a biological sample from the subject's cancer the amount of Her-2 and Her-2 homodimers and determining the ratio of Her-2 homodimers to total Her-2, wherein the subject's ratio is determined to be in one of at least 3 subgroups and if the subject's ratio is in the low or high subgroup, then the subject is likely to respond to the Her-2 acting agent, the subject is likely to have a long time course and/or the subject is not likely to have a significant event. In a preferred embodiment, the at least three subgroups are determined by comparing the Her-2 homodimer to total Her-2 ratio to the hazards ratio for populations treated with versus without a Her-2 acting agent, wherein if the hazard ratio is less than 1, then the subject is more likely to respond to the Her-2 acting agent, the patient is more likely to have a long time course and/or the patient is less likely to have a significant event. In certain embodiments, the subject's cancer is breast cancer. In certain embodiments, the subject's cancer is metastatic or primary adjuvant. In certain embodiments, the Her-2 acting agent is trastuzumab. In certain embodiments, Her-2 and Her-2 homodimers are detected using the VeraTag™ assay. In certain embodiments, the likeliness to respond, likeliness to have a long time course and/or likeliness to have a significant event is measured as an overall survival rate, as time to progression, as time to distant recurrence and disease-free survival and/or response or clinical benefit using the RECIST criteria. In certain embodiments, whether the cancer is Her-2 positive is determined by IHC or FISH or CISH. In other embodiments, the invention is drawn to a method comprising determining whether the Her-2 homodimer to total Her-2 ratio is low, intermediate or high by comparing the Her-2 homodimer to total Her-2 ratio of the subject's cancer to optimal cutoffs. In yet further embodiments, if the ratio of Her-2 homodimers to total Her-2 is intermediate and/or the hazard ratio is equal to or greater than 1, then the patient is less likely to respond to a Her-2 acting agent and/or the patient is less likely to have a long time course and/or the patient is more likely to have a significant event.

In a further aspect, the invention provides methods of treating a subject with cancer. In one aspect, the methods comprise determining that the subject is afflicted with a cancer that is likely to respond to treatment with a Her-2-acting agent and/or has a long time course according to a method of the invention, and administering an effective amount of a Her-2-acting agent to the subject as a result of said determination. In another aspect, the methods comprise determining that a subject is afflicted with a cancer that is likely to respond to treatment with a Her-2-acting agent according to a method of the invention, then advising a medical professional of the treatment option of administering to the subject an effective amount of a Her-2-acting agent. In another aspect, the methods comprise determining that a subject is afflicted with a cancer that has a short time course and/or that is unlikely to respond to a chemotherapeutic agent in addition to a Her-2 acting agent. In certain embodiments, the Her-2-acting agent is trastuzumab. In certain embodiments, the chemotherapeutic agent is paclitaxel. In certain embodiments, the cancer is breast cancer. In certain embodiments, the breast cancer is metastatic.

BRIEF DESCRIPTION OF THE DRAWINGS

FIG. 6 shows correlation of Her-2 expression by eTag™ assay and IHC in 170 breast tumors as set forth in Example 16. The top graph shows the correlation of the IHC integer score (x-axis) and the Her-2 expression by eTag™ assay (y-axis). The bottom shows the continuous H Score (y-axis) plotted against Her-2 expression as measured by eTag™ assay (x-axis).

FIG. 7 shows a correlation of Her-2 expression by eTag™ assay with total FISH copy number as set forth in Example 16. FIG. 7A shows FISH copy (x-axis) number plotted against Her-2 expression (y-axis), as measured by eTag™ assay.

respectively, where H2=Her-2 expression, H22D=Her-2 homodimers, $H2_{adj}$=the value of Her-2 expression adjusted for the other confounding variables as given by the Cox model, $H22D_{adj}$=the value of Her-2 homodimers adjusted for the other confounding variables as given by the Cox model, traz only=treatment with trastuzumab only, # mets=number of organs with metastases, and β=the coefficient derived from the Cox model for that variable. The distributions are divided by the median values. The left graph displays Her-2. The right graph displays Her-2 homodimers. The top lines show High Her-2 or homodimers, and the bottom lines show low Her-2 or Her-2 homodimers. The x-axis of each graph shows overall survival in months. The y-axis shows percent survival.

Figure 9:
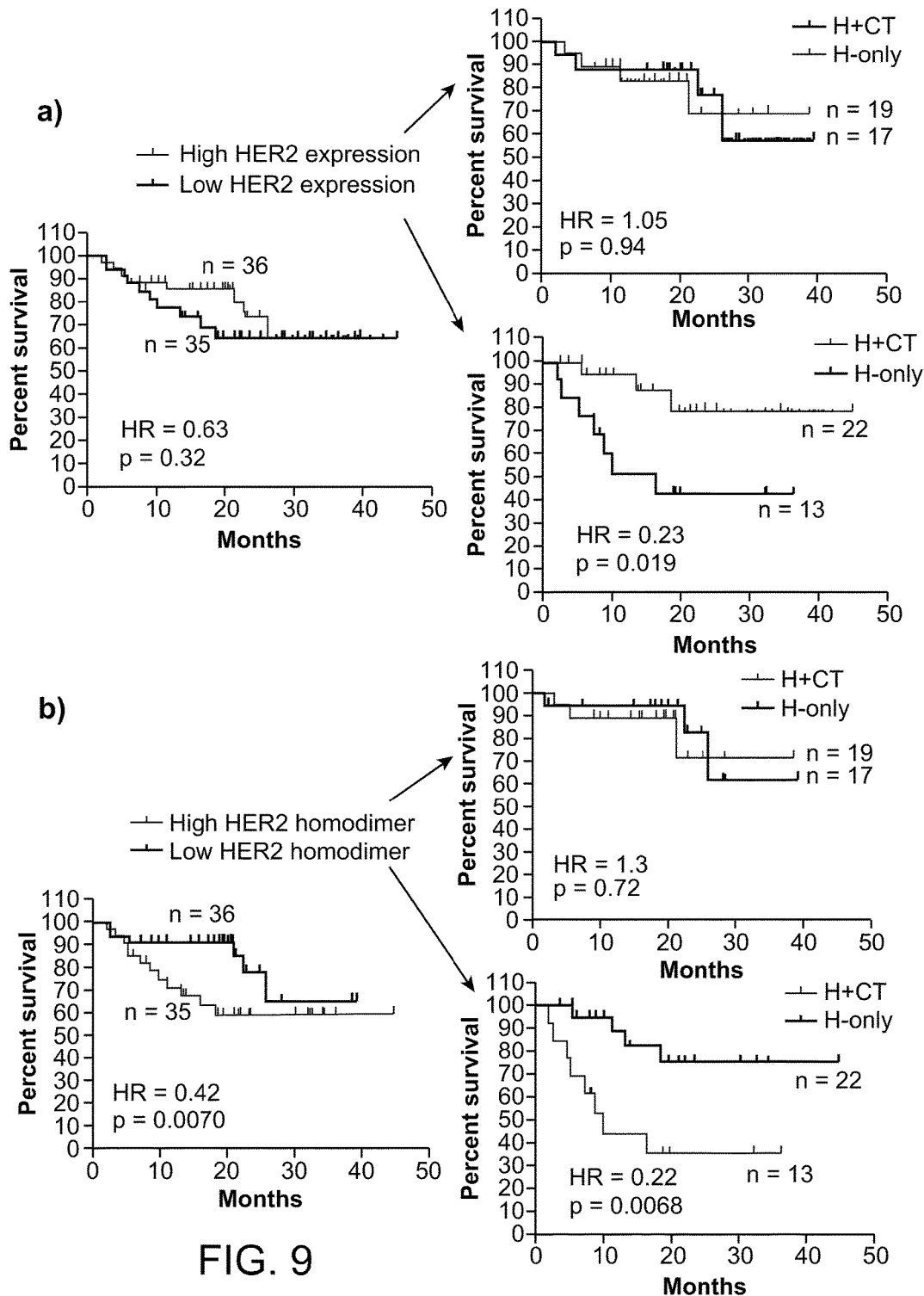

FIG. 9 shows a Kaplan-Meier analysis with unadjusted eTag™ variables showing the relationship of Her-2 expression and Her-2 homodimer levels with overall survival as set forth in Example 19. The left panel shows the unadjusted univariate relationships with overall survival. FIG. 9A shows the relationship between Her-2 expression and overall survival when the Her-2 distribution is divided at the median. FIG. 9B shows the relationship between Her-2 homodimers and overall survival when the distribution is divided at the median. The right panels show survival according to treatment regimen (trastuzumab alone vs. trastuzumab and paclitaxel) in the upper half vs. the lower half of distribution. For both Her-2 expression and Her-2 homodimers, only the lower half of the distribution appears to benefit from the concomitant administration of chemotherapy.

FIG. 10 shows Kaplan-Meier analyses for overall survival correlated to (a) H2T (HER2) expression and (b) H22D (HER2 homodimer) expression. In this figure, the levels of H2T and H22D are Cox-adjusted. In each panel, the upper line shows the high expressors, the lower line shows the low expressors.

FIG. 11 shows Kaplan-Meier analyses of overall survival correlated to (a) H2T (HER2) expression and (b) H22D (HER2 homodimer) expression in the subgroup of patients treated with trastuzumab only in the Bordet cohort. This relationship may be clearer than that shown in FIG. 10 due to the lack of confounding influence by chemotherapy. In each panel, the upper line shows the high expressors, the lower line shows the low expressors.

Figure 12:
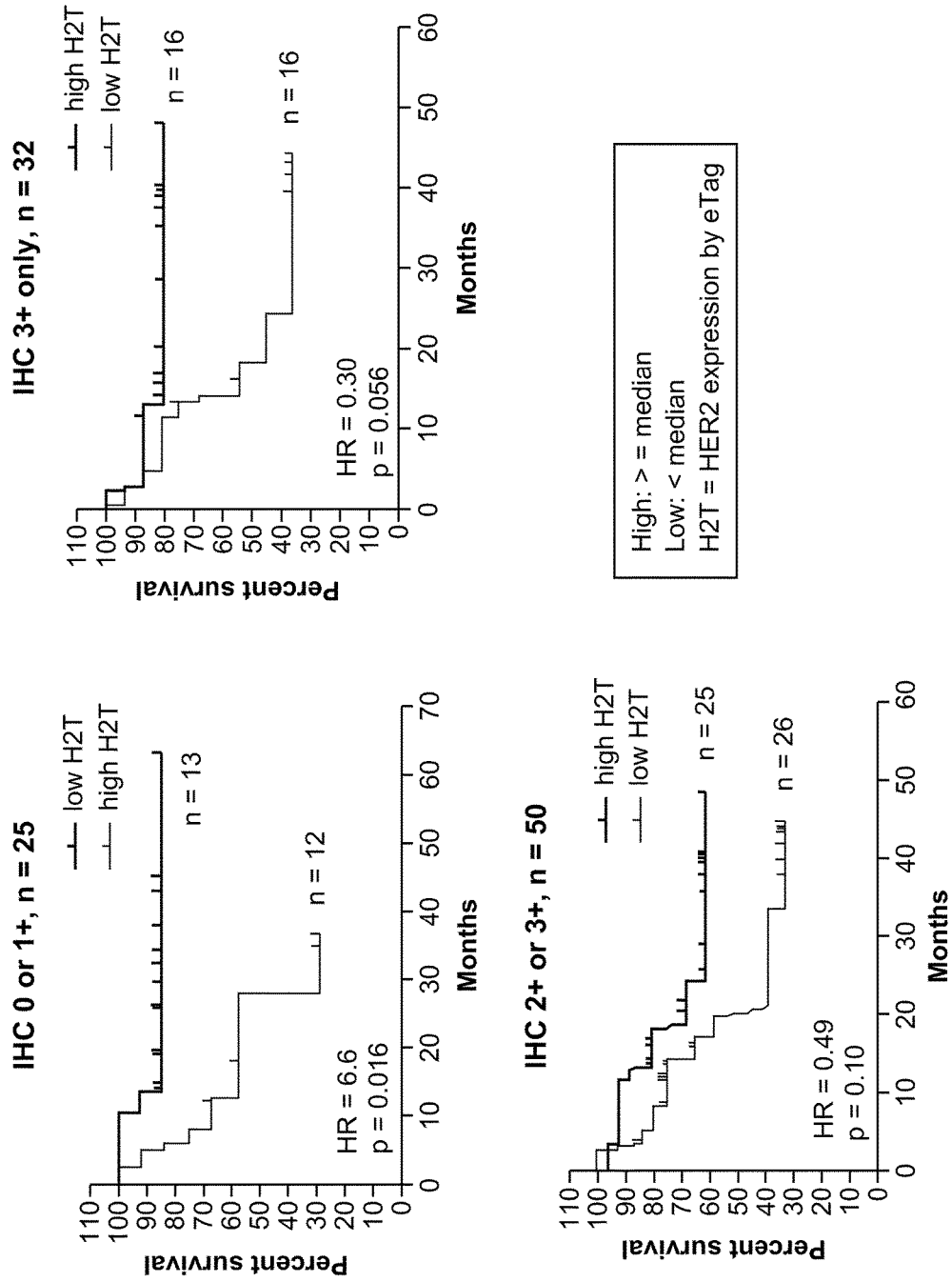

FIG. 12 shows a univariate Kaplan-Meier analysis of the IHC subgroups 0-1+, 2-3+ and 3+ alone, above as set forth in Example 21. High expression are those groups above the median, and low expression are those groups below the median. In each of the graphs, the x-axis shows percent survival and the y-axis shows overall survival. From the graph, one can see that high Her-2 expression correlates with better overall survival in the subgroup of patients that are truly over-expressing Her-2, as determined by repeat IHC scores of 2+ or 3+. In the 0, 1+ group, the top line is low H2T, the bottom line is high H2T. In the 2+, 3+ and 3+ only groups, the top line is high H2T, the bottom line is low H2T.

Figure 13:
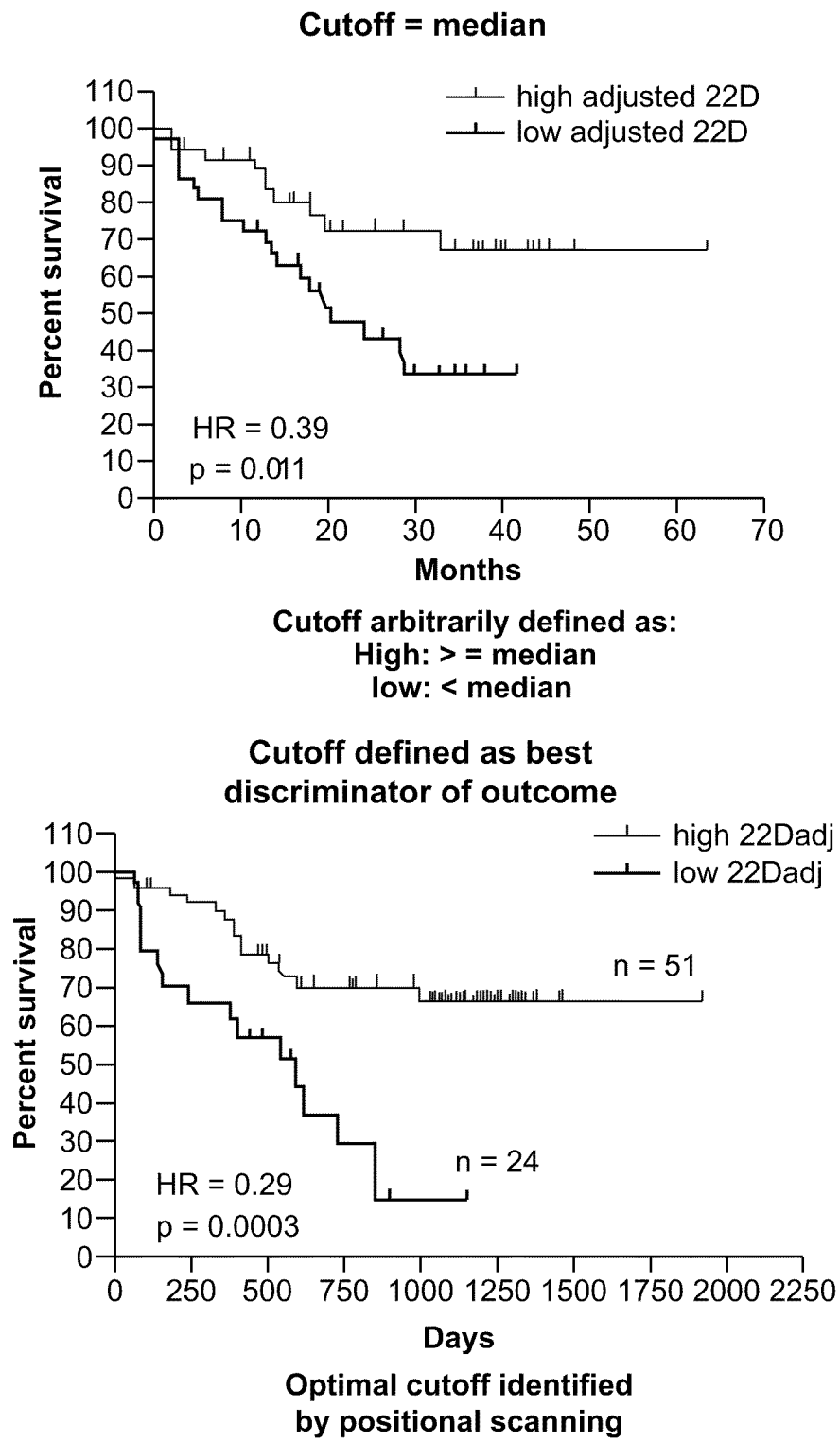

FIG. 13 shows the Kaplan-Meier analysis of Her-2 homodimer levels and overall survival using the sum of the weighted variables from Cox as set forth in Example 21 and using either the median cutoff (left panel) or optimal cutoff (right panel). Top lines show high H22D, the bottom lines show low H22D.

Figure 14:
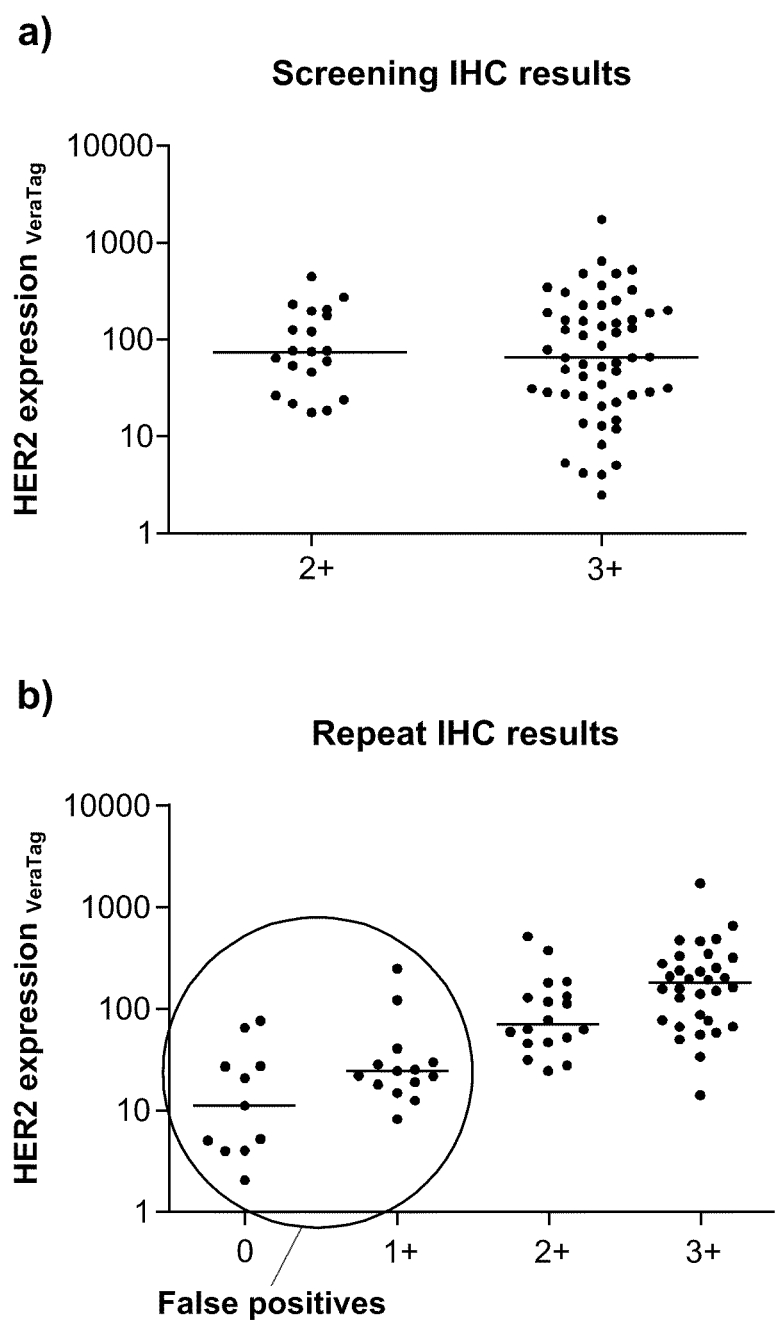

FIG. 14 shows the correlation between IHC data and H2T levels, as determined by VeraTag™ assay, in the Toi cohort. FIG. 14a shows the results of the initial screening IHC using non-standardized methods, performed by different pathologists at different institutions. FIG. 14b shows the results of repeated IHC assays that were performed using standardized methods by a single pathologist. These repeated IHC studies identified 25/75 patients as "false positives" (shown in circle).

Figure 15:
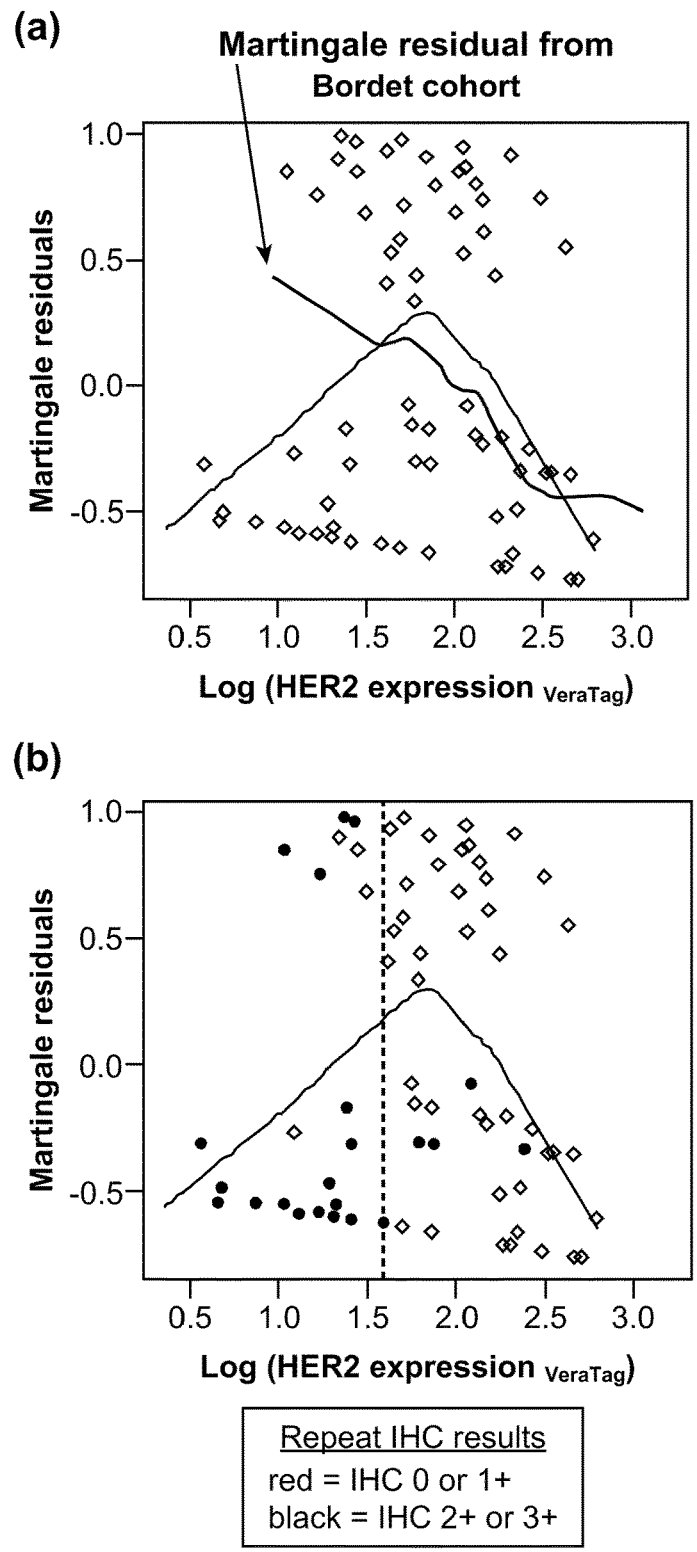

FIG. 15 shows the correlation between the Martingale residuals (a statistical method for examining the hazard associated with a continuous variable) and H2T levels, as determined by VeraTag™ for the Bordet and Toi cohorts. The IHC-negative (0, 1+) data are shown as solid circles; the IHC-positive (2+, 3+) are shown as open circles in FIG. 15b. FIG. 15a shows the comparison between the MRs of the Bordet and Toi cohorts: the line with a negative slope shows the MR for the Bordet cohort, the mountain-shaped line shows the MR for the Toi cohort. The negative slope seen for the Bordet cohort and part of the Toi cohort (on the right side) denotes a hazard that is dropping continuously as H2T increases. A positive slope (the left side of the Toi cohort) denotes a hazard that is rising as H2T increases. FIG. 15b shows that "false positives" identified by the repeated IHC are responsible for the increasing hazard on the left side of the vertical dotted line. Those patients on the right side of the dotted line, most of whom have high H2T levels, show decreasing hazard.

Figure 16:
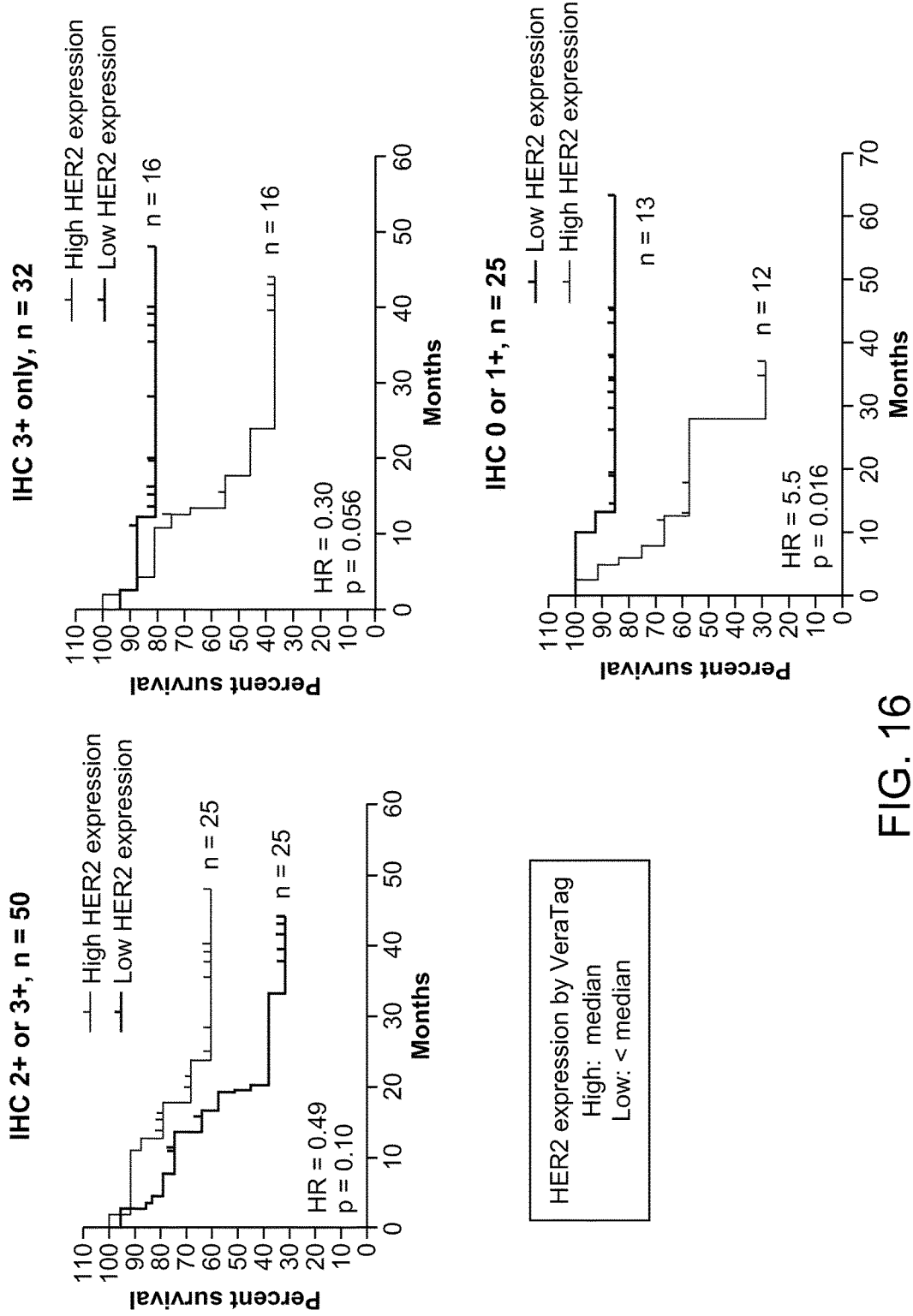

FIG. 16 shows Kaplan-Meier analyses of subgroups within the Toi cohort. The median value of H2T was used as a cutoff between high and low H2T expression. Using the median value cutoff, consideration of the subgroup within Toi that corresponded to the higher values in the distribution (1HC 2+ and 3+ on repeat testing) revealed relationships similar to those seen in Bordet (high H2T portends better OS than lower values of H2T). Those patients at the lower end of the H2T distribution (1HC 0 or 1+ on repeat testing) behave differently. In the top panels (IHC 2+, 3+ and IHC 3+), the upper lines represent the high expressors. In the bottom panel (IHC 0 or 1+), the lines are reversed: the top line shows the low expressors, the bottom line represents the high expressors.

Figure 17:
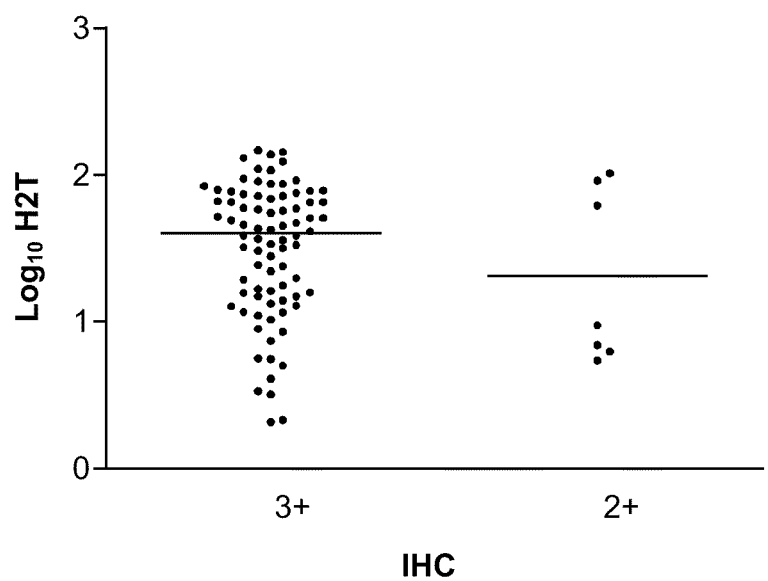

FIG. 17 shows the correlation of H2T, as assessed by VeraTag™ assay, with IHC in the Lipton cohort. Nearly all patients were assessed as IHC3+. The horizontal lines denote the medians for H2T levels in each IHC group.

Figure 18:
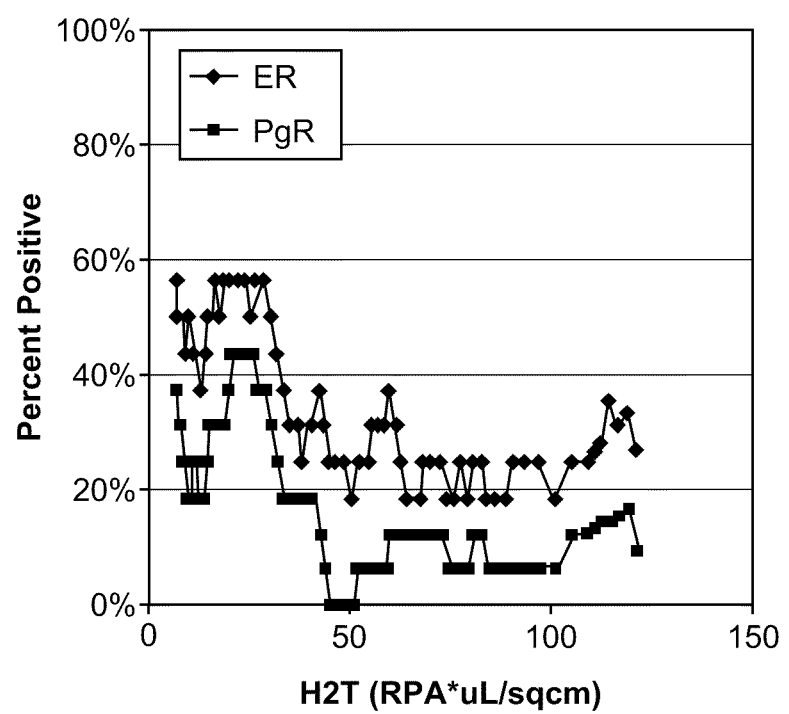

FIG. 18 shows the correlation of H2T, as assessed by VeraTag™ assay, with estrogen receptor (ER) and progesterone receptor (PR) percent positivity in the Lipton cohort. The inverse relationship suggested by these data is consistent with what has been reported in the literature. The top line is ER, the bottom line is PR.

Figure 19:
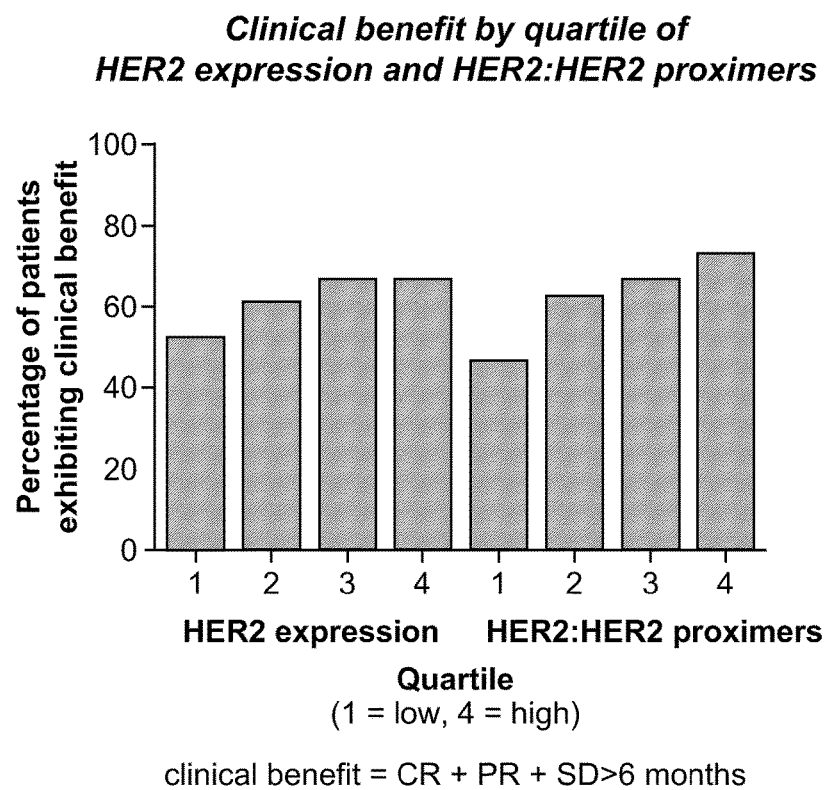

FIG. 19 shows the correlation of H2T and H22D with clinical benefit by RECIST responses in the Bordet cohort (clinical benefit=CR+PR+SD>6 months). The data for H2T levels were divided into quartiles (Quartile 1=lowest 25% of H2T expression/H22D distribution).

Figure 20:
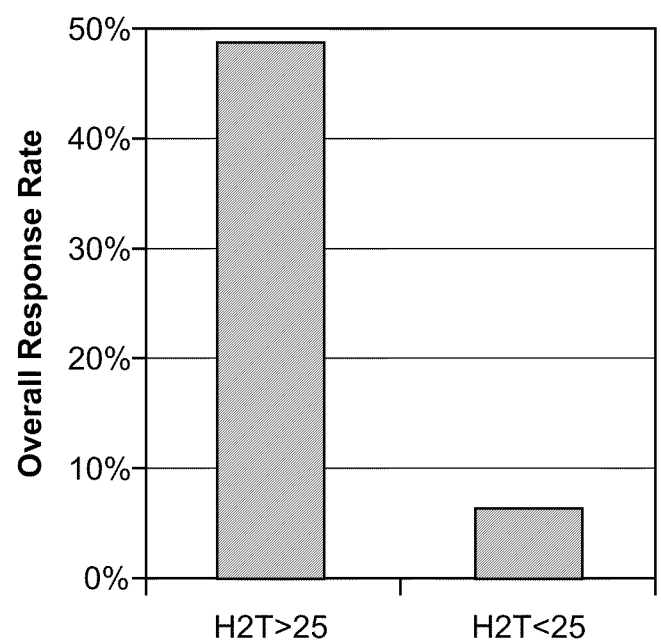

FIG. 20 shows response rates (CR+PR) in the upper versus the lower half of the H2T distribution in the Lipton cohort. The median H2T level was used as a cutoff. This difference is statistically significant (p<0.001).

Figure 21:
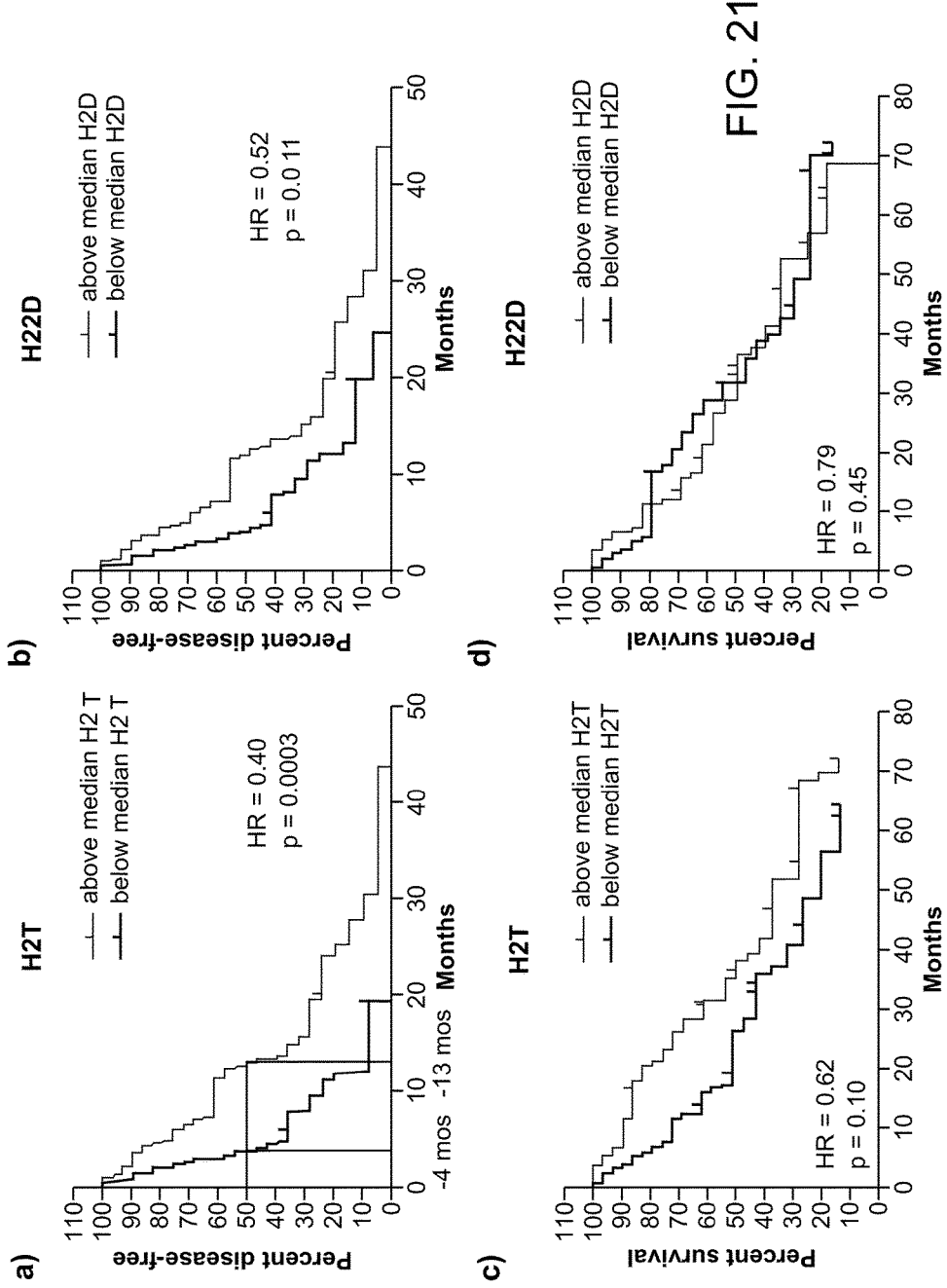

FIG. 21 shows Kaplan-Meier analyses of the Lipton cohort using OS and TTP endpoints. Panels (a) and (b) show the TTP endpoints for H2T and H22D, respectively. Panels (c) and (d) show the OS endpoints for H2T and H22D, respectively. As shown by the vertical lines in (a), those patients with H2T levels above the median of the distribution by VeraTag™ assay experienced a median 13-month TTP while those below the median of the H2T distribution experienced a median 4-month TTP (p=0.0003). The benefit for OS is less evident, but the trend (p=0.1) favors those above the median for H2T. For H22D, a statistically significant relationship is seen for TTP (p=0.011), while there is no observed difference between the high and low H22D for the OS endpoint.

Figure 22:
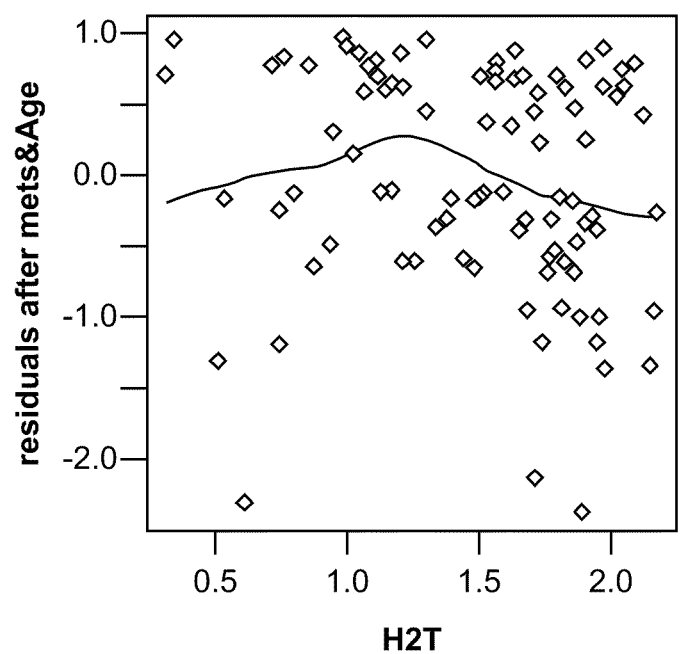

FIG. 22 shows Martingale residuals for the Lipton cohort. The same biphasic relationship observed in Toi is once again in evidence here, although less pronounced. Following normalization of these data to Toi using shared controls, the cutoff derived from Toi can be applied to Lipton to identify the "false positives" at the low end of the H2T distribution.

Figure 23:
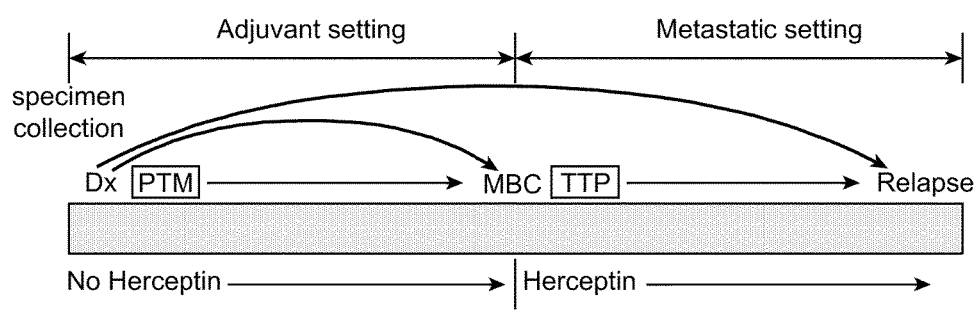

FIG. 23 shows the general course of disease progression for the patients in the ISHSG cohort. Tumor specimens were taken at the time of primary diagnosis (Dx). Most patients (all but 9 of the 106) were treated in the adjuvant setting until they failed with metastatic disease (MBC), at which point they received trastuzumab (almost all with chemotherapy). PTM (primary to metastases) is defined as the time from initial diagnosis to metastasis. TTP is shown as the time from MBC to relapse (the straight arrow on the right). The straight arrow on the left denotes PTM, when most of the patients were in an adjuvant setting (i.e., no trastuzumab).

Figure 24:
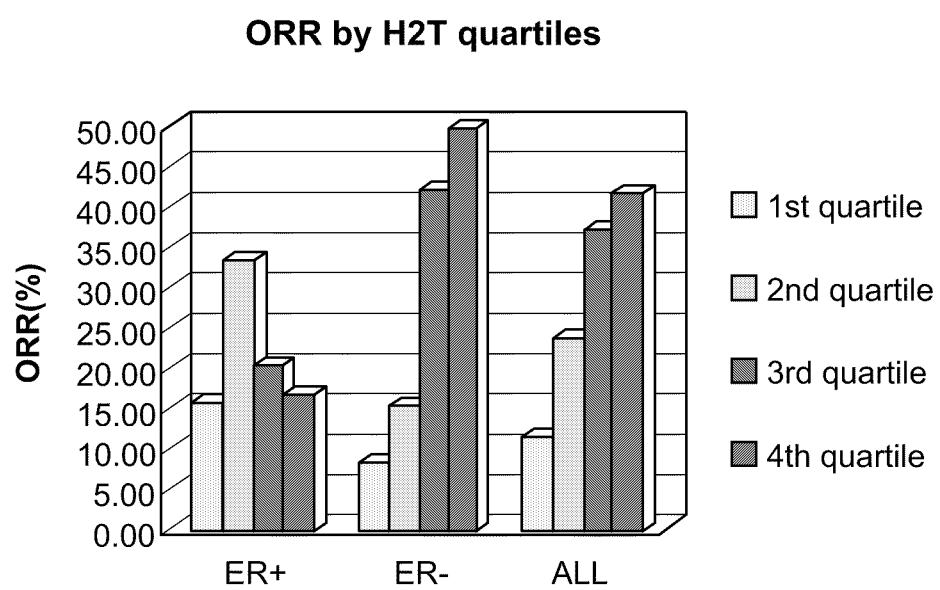

FIG. 24 shows the correlation between H2T levels, as assessed by VeraTag™ assay, and response rate (ORR) in the ISHSG cohort. Results are shown for all patients, as well as ER positive and ER negative patients. The three subgroups were each split into quartiles (1st quartile=lowest 25% of H2T distribution). ORR=objective response rate=CR+PR/CR+PR+SD+PD.

Figure 25:
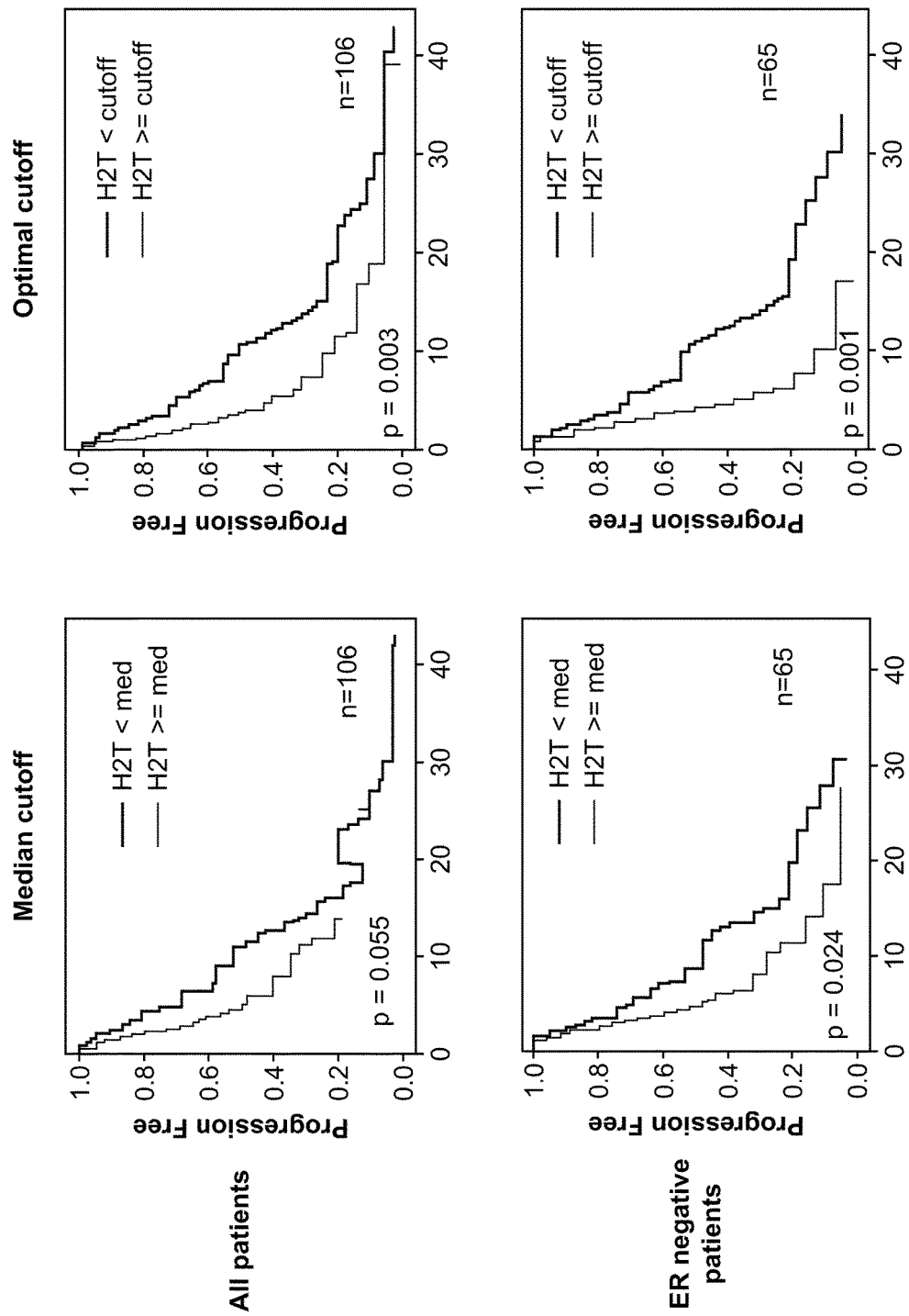

FIG. 25 shows univariate Kaplan-Meier analyses for TTP in patients with high or low levels of H2T (top panels) in the ISHSG cohort and represents an update of the data presented in FIG. 21, but includes all 106 patients from the cohort. (The name Lipton has been used herein to describe the early analysis of 92 patients; the name ISHSG is used to describe the full cohort of 106 patients.) The lower panels show results for TTP for patients who are ER negative. The left panels show results for data in which "high" or "low" levels were assigned using the median H2T level as a cutoff. The right panels show results in which the cutoff was optimized by choosing the lowest p-value among all possible cutoffs. An enhanced correlation was observed for the ER negative subgroup.

Figure 26:
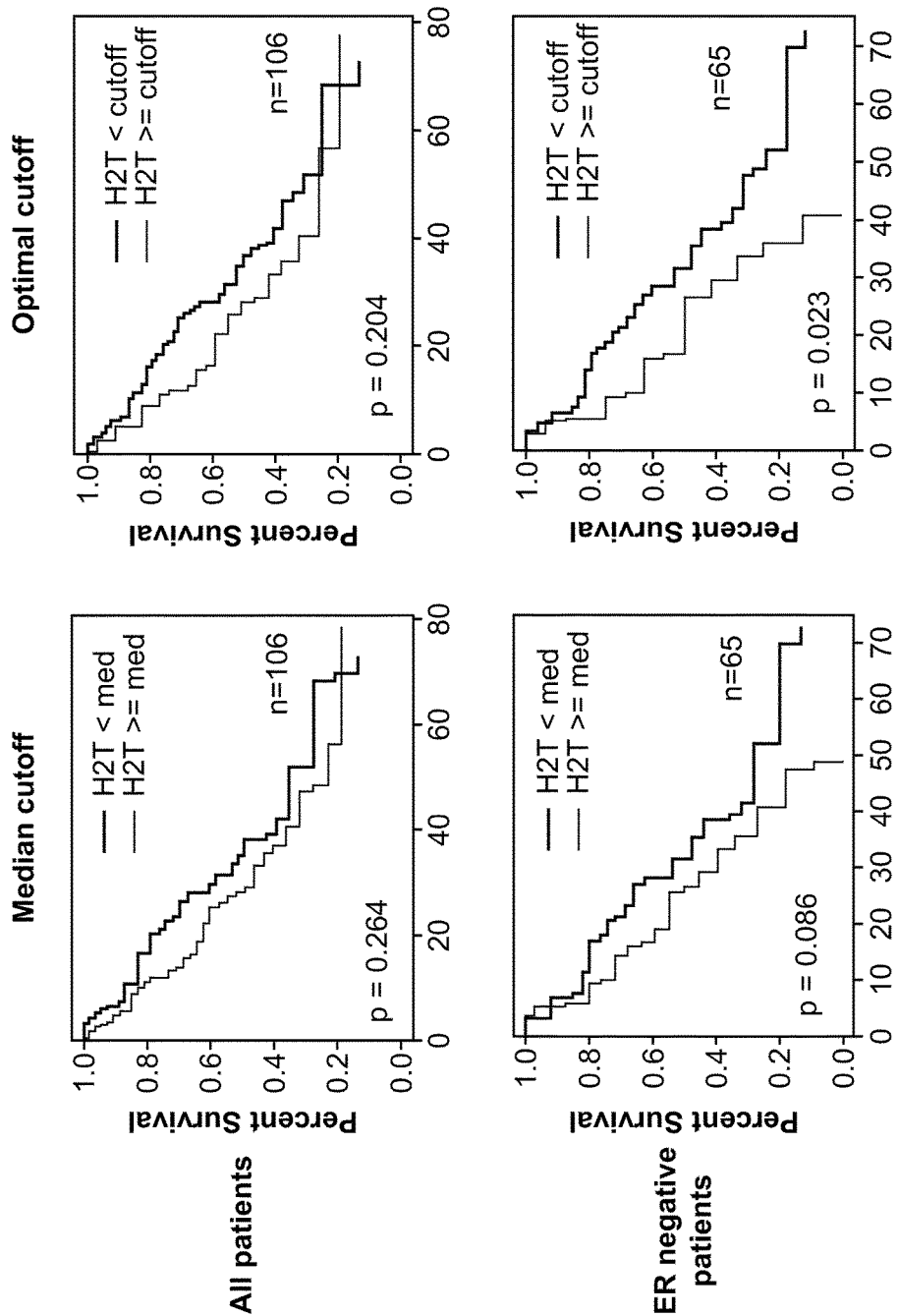

FIG. 26 shows univariate Kaplan-Meier analyses for OS in patients with high or low levels of H2T (top panels) in the ISHSG cohort. The lower panels show results for OS for patients who are ER negative. The left panels show results for data in which "high" or "low" levels were assigned using the median H2T level as a cutoff. The right panels show results in which the cutoff was optimized by choosing the lowest p-value among all possible cutoffs. An enhanced correlation was observed for the ER negative subgroup.

Figure 27:
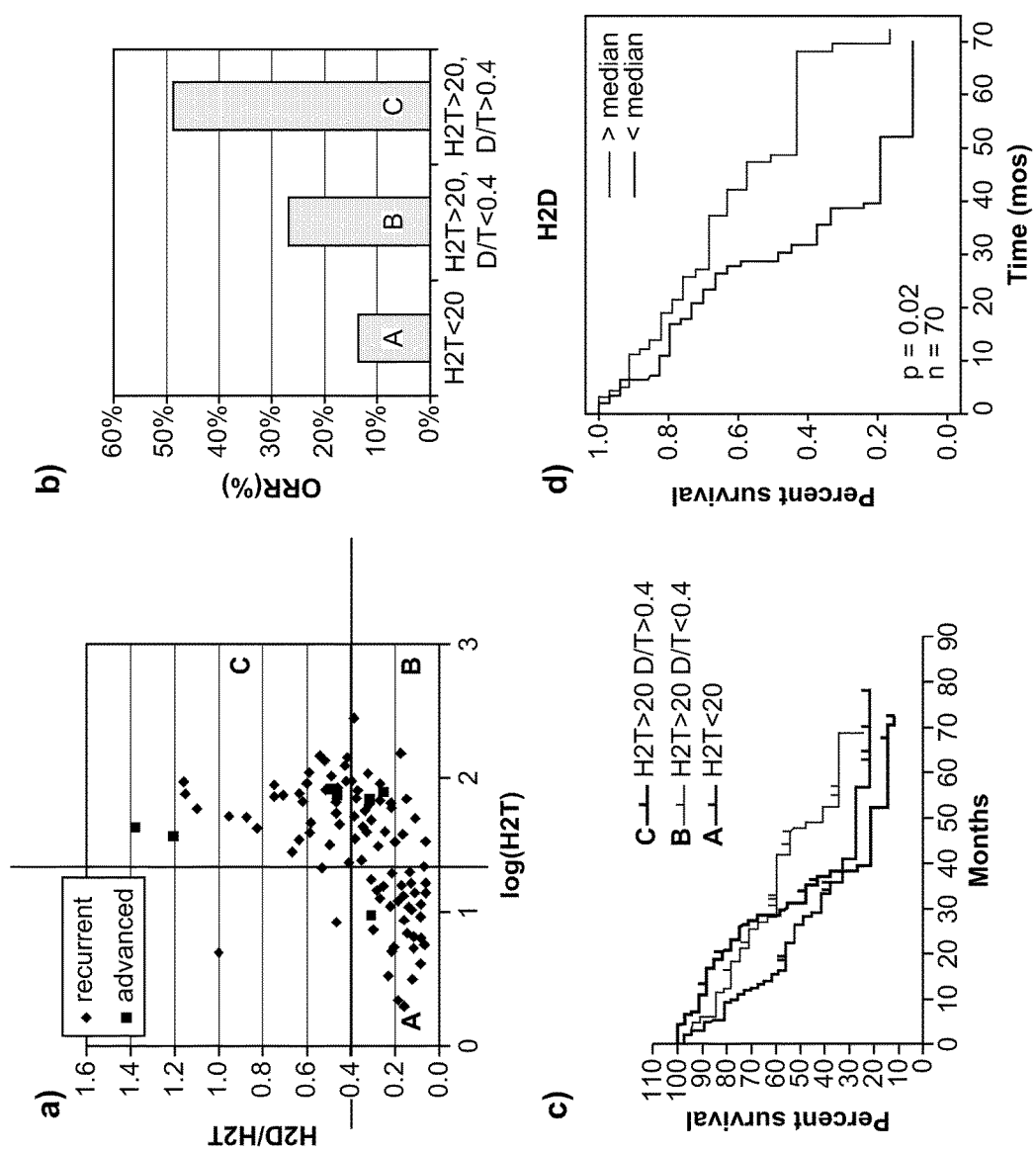

FIG. 27 shows analyses of sub-populations of the ISHSG cohort. Panel (a) shows how three subgroups (A, B, and C) were selected. Group A expresses levels of H2T<20. Groups B and C express H2T at levels ≥20 but show different levels of H22D/H2T. Group B shows H22D/H2T<0.4. Group C shows H22D/H2T≥0.4. Panel (b) shows the ORR for the three sub-populations. The high H2T, high H22D/H2T group C has the best response rate. Panel (c) shows Kaplan-Meier analyses for OS for groups A, B, and C. At 70 months, the top line is group A, the middle line is Group C, and the bottom line is group B. Interestingly, Group C patients (high H2T, high H22D/H2T) do progressively worse over time than Group B (high H2T, low H22D/H2T). Panel (d) shows the Kaplan-Meier analyses for patients with high H22D and low H22D (top line is low H22D, bottom line is high H22D), which show remarkably similar patterns to the those observed for the high H2T, high H22D/H2T (Group C) and high H2T, low H22D/H2T (Group B) comparison shown in panel (c).

FIG. 28 shows analyses of sub-populations of the ISHSG cohort. Panel (a) shows how three subgroups (A, B, and C) were selected. The analysis shows certain optimal cutoffs, as disclosed herein. Group A expresses levels of H2T<1.14 (this number is the log of the H2T score—e.g., 1.14 is the log of an HRT level of ~13.8). Groups B and C express H2T at levels ≥1.14 but show different levels of H22D. Group B shows H22D<1.15. Group C shows H22D≥1.15. Panel (b) shows the ORR for the three sub-populations. The high H2T, high H22D group C has the best response rate. Panel (c) shows a Kaplan-Meier analysis for OS for groups A, B, and C. At 60 months, the top line is group B, the middle line is group A and the bottom line is group C. Panel (d) shows that Group C patients (high H2T, high H22D) do progressively worse over time than Group B (high H2T, low H22D). At 60 months, the top line is high H2T, low H22D; the bottom line is high H2T, high H22D.

FIG. 29 describes the breast cancer patient population used for several studies shown herein. All patients were given trastuzumab based on HER-2 IHC 3+ status or HER-2 FISH-positive measurements made on FFPE sections from the primary tumor. At a later date, FISH measurements were made for all patients at a central laboratory (shown in table).

FIG. 29A shows total Her-2 (H2T) and Her-2 homodimer (H2D) as measured by the HerMark assay (performed using additional FFPE samples from the same tumor), as well as the H2D/H2T ratio, compared to the IHC (2+ or 3+) and FISH measurements (those performed by a central laboratory and scored as FISH-negative or FISH-positive). Some correlation was seen between H2T and H2D with both IHC and FISH. The H2D/H2T ratio showed significant correlation with both IHC and FISH data, as well as with FISH/CEP17, which reflects the number of Her-2 gene copies on chromosome 17.

Figure 29B:
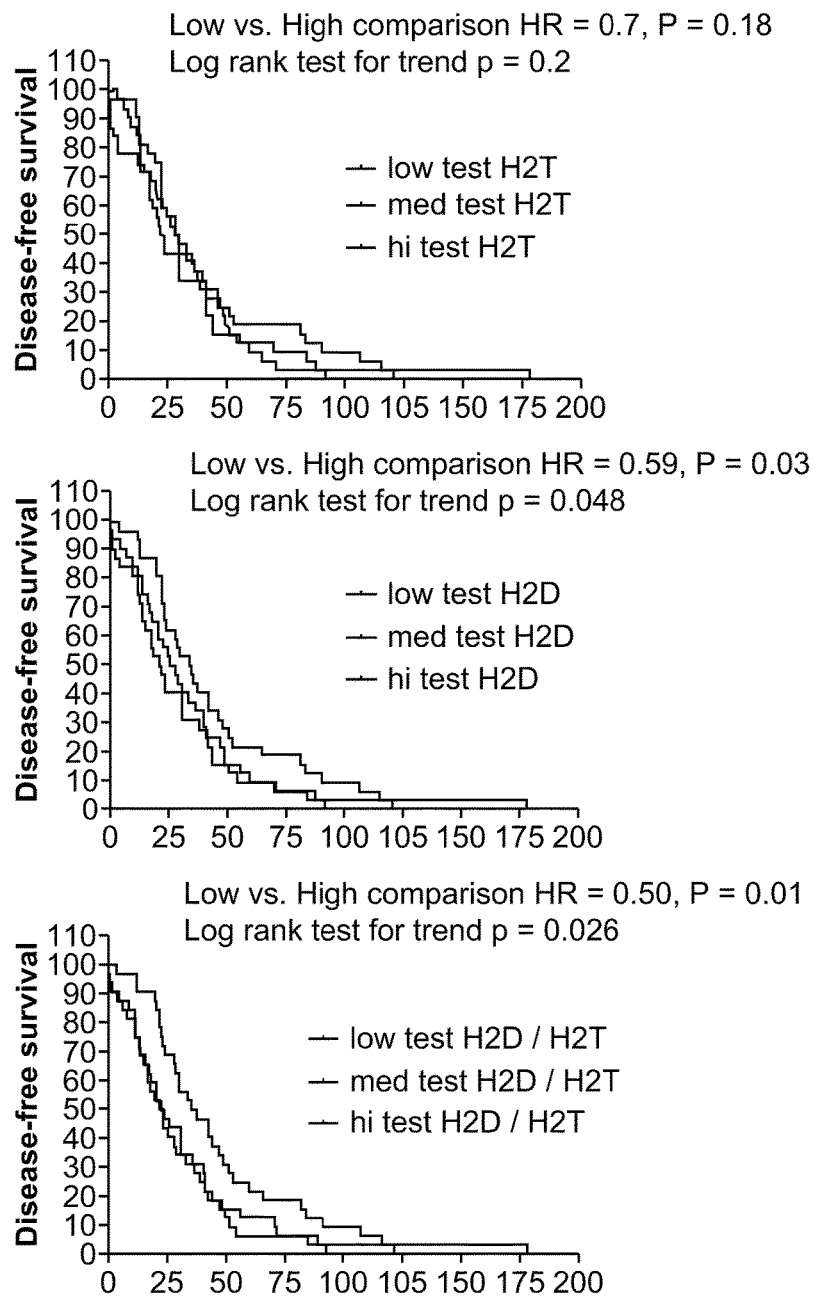

FIG. 29B shows Kaplan-Meier plots of disease-free survival (DFS) in an adjuvant setting by tertiles of H2T, H2D, or H2D/H2T in the left, middle, and right panels, respectively. While Her-2 expression itself did not correlate with DFS, both low H2D and low H2D/H2T showed a longer DFS.

FIG. 29C shows 3 graphs comparing the level of phospho-Her-2 (H2P) to H2T, H2D, and H2D/H2T in the left, middle and right panels, respectively. For these studies, FFPE samples were prepared from 18 tumor samples and H2T, H2T and H2P were measured using the VeraTag™ assay. Significant correlations of H2P with H2T, H2D, and H2D/H2T were found for this cohort. The strongest correlation with H2P was found for H2D/H2T ($R^2=0.40$).

Figure 34:
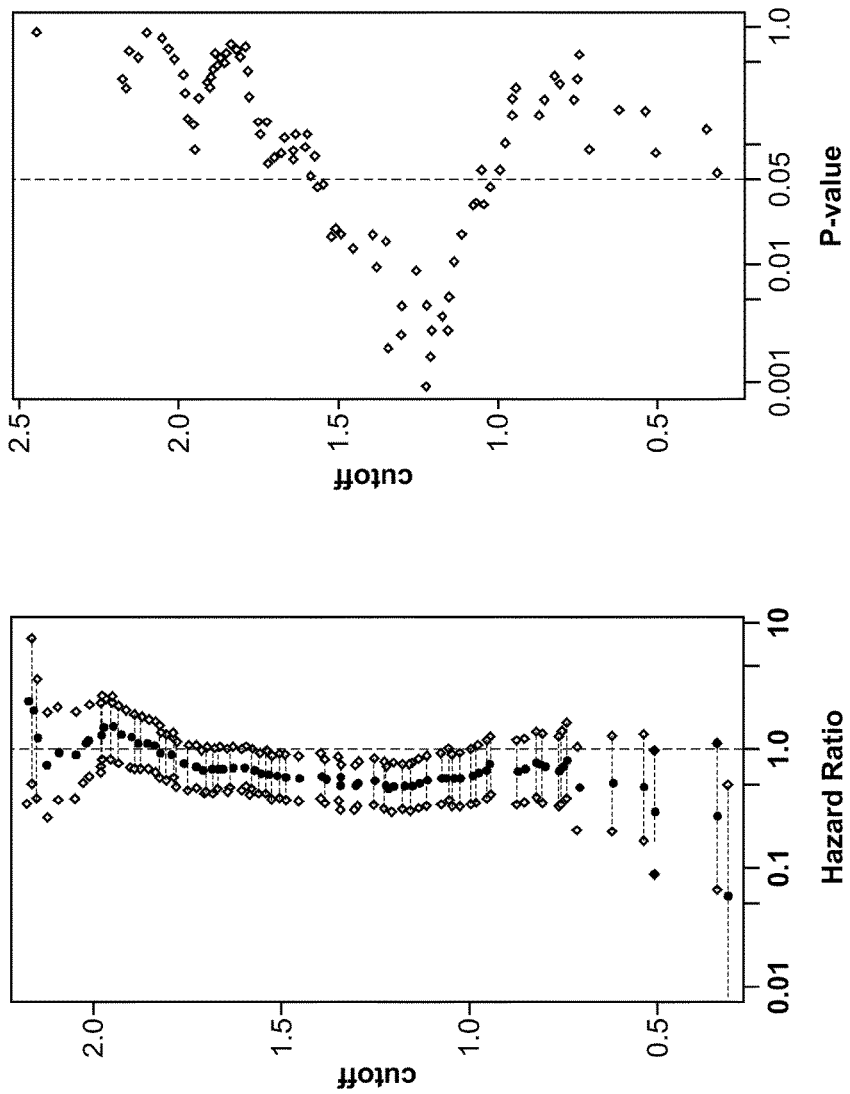

FIG. 30 shows Cox proportional hazards analyses for the cohort described in Example 35. HERMark measures and Her-2 FISH were considered for their ability to predict outcomes (TTP, time to progression; OS, overall survival), in the metastatic setting for patients on trastuzumab. The top panel shows Cox proportional hazards multivariate analysis for the entire cohort of 103 patients. The bottom panel shows the Cox proportional hazards multivariate analysis for the FISH-positive patients (N=77). Cutoffs for H2T and H2D were derived as shown in FIG. 34 by testing all possible cutoffs and selecting the optimal cutoff as the cutoff with the lowest p-value (which was log(H2t)~1.2). The results in the upper panel show that either H2T or H2D are stronger predictors of outcome in this cohort than FISH. For the FISH-positive portion of the cohort (shown in the bottom panel), H2T can be used to predict better and worse TTP and OS (p=0.0015 and 0.02, respectively).

Figure 31:
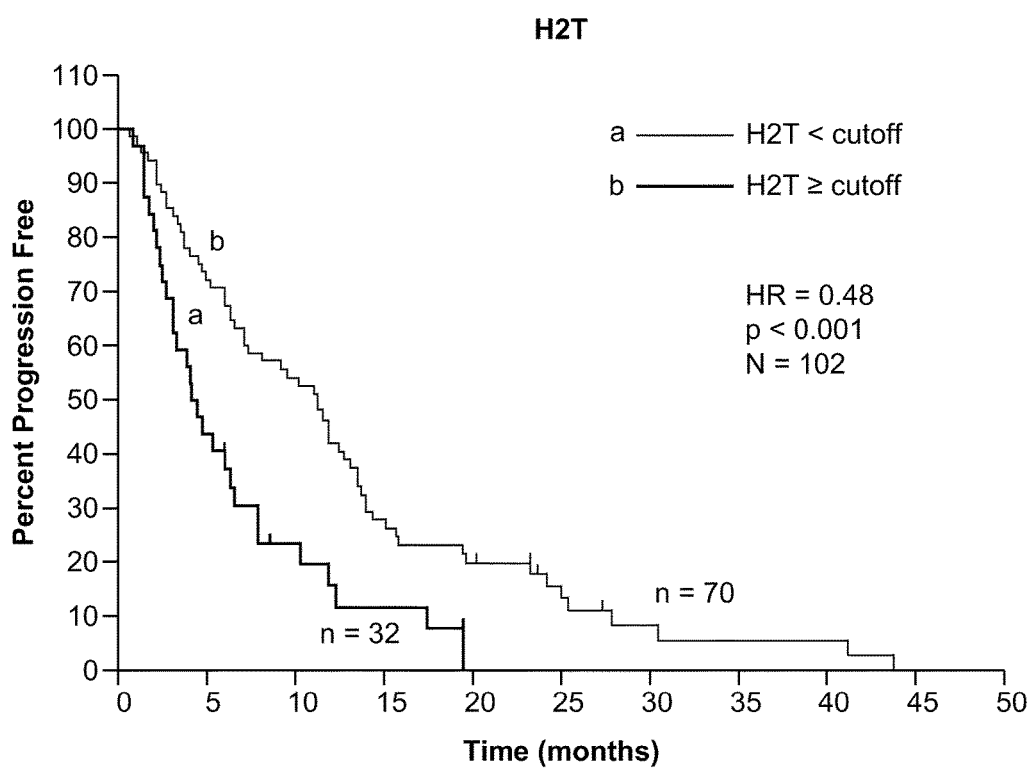

FIG. 31 shows a univariate time to progression analysis for patients with H2T values below (line a) and equal to or above (line b) an optimal H2T cutoff (HR=0.48, p<0.001). H2T is a stronger predictor of outcome than FISH. H2D shows similar results (data not shown here).

Figure 32:
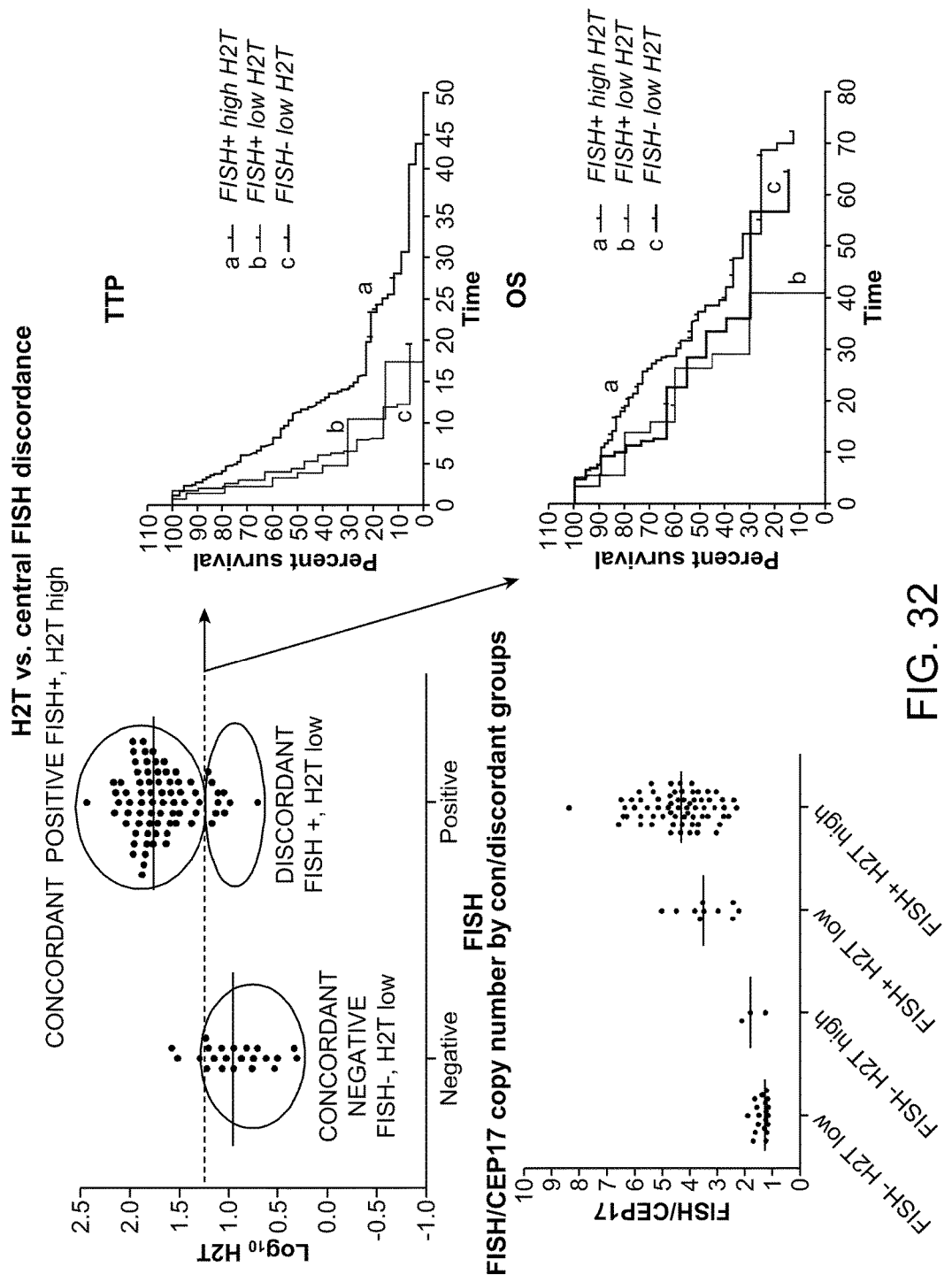

FIG. 32 shows a direct comparison of H2T and FISH cutoffs and their ability to predict outcome for patients on trastuzumab. The top left panel highlights three groups defined by the FISH and H2T cutoffs. Two of these groups are concordant in that both assay methods agree in predicting worse (H2T-low/FISH-negative) and better (H2T-high/FISH-positive) outcomes. There is a discordant group, H2T-low/FISH-positive, for whom the HERMark assay would predict an outcome similar to the H2T-low/FISH-negative group, while FISH would predict an outcome similar to the H2T-high/FISH-positive group. As shown in the 2 panels on the right, the H2T correctly predicts outcome for this discordant group. The Kaplan-Meier plots for time to progression (TTP) and overall survival (OS) are shown in the top right and bottom right panels, respectively. In each plot, lines a, b and c represent H2T-high/FISH-positive, H2T-low/FISH-positive and H2T-low/FISH-negative, respectively.

The lower left panel of FIG. 32 shows that these results cannot be explained by a number of patients in the discordant group falling very close to the FISH cutoff. The H2T-low/FISH-positive subgroup showed a similar range and median of FISH scores to the H2T-high/FISH-positive subgroup. These results are consistent with the idea that in tumors largely driven by HER2 receptor activity, the highly quantitative measure of HER2 receptor content (H2T) is more predictive than a measure of gene copy number (FISH) which strongly influences but does not have a one-to-one relationship with HER2 protein levels.

Figure 33:
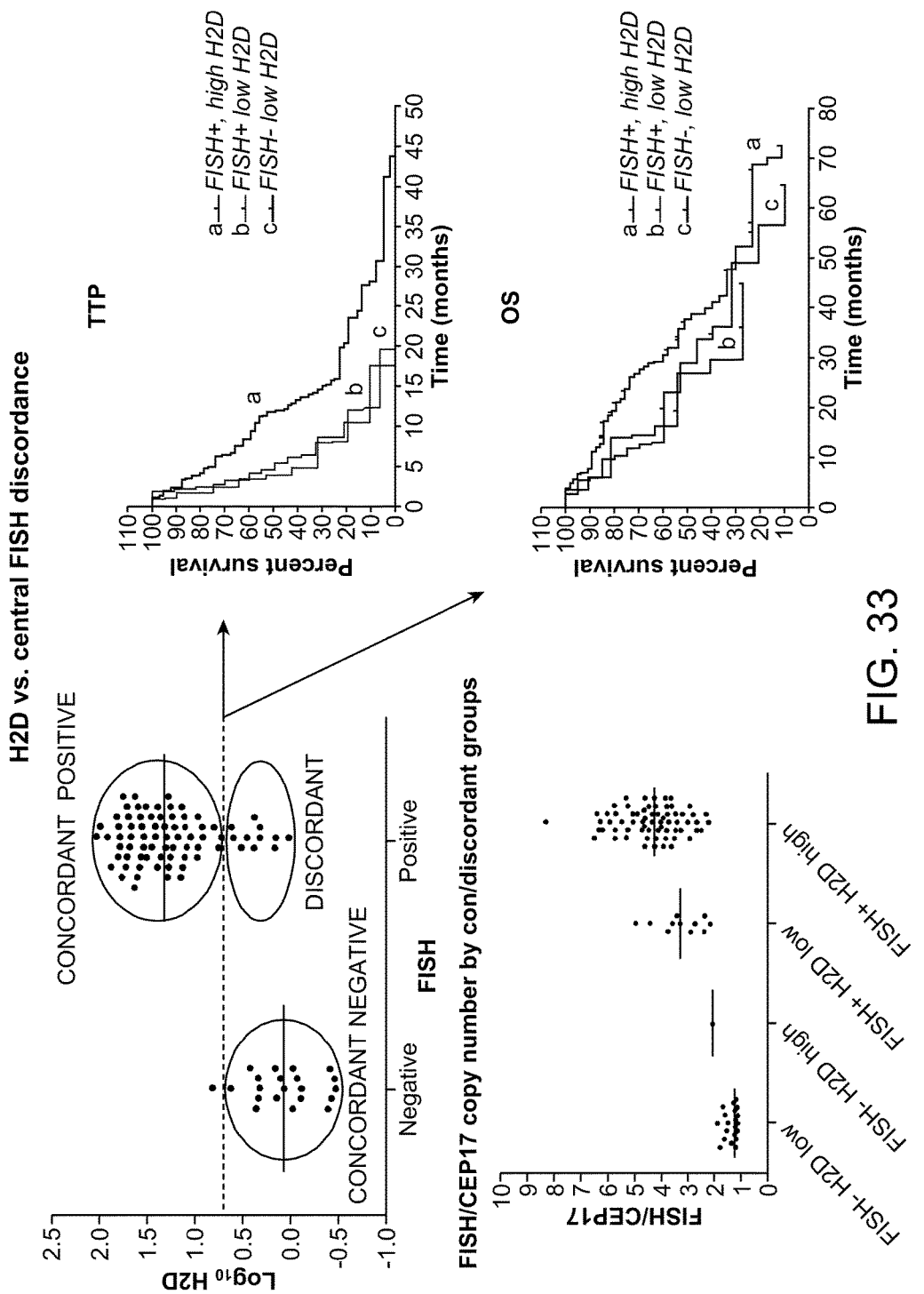

FIG. 33 shows a direct comparison of H2D and FISH cutoffs and their ability to predict outcome for patients on trastuzumab. The top left panel highlights three groups defined by the FISH and H2D cutoffs. Two of these groups are concordant in that both assay methods agree in predicting worse (H2D-low/FISH-negative) and better (H2D-high/FISH-positive) outcomes. There is a discordant group, H2D-low/FISH-positive, for whom the HERMark assay would predict an outcome similar to the H2D-low/FISH-negative group, while FISH would predict an outcome similar to the H2D-high/FISH-positive group. As shown in the 2 panels on the right, the H2D correctly predicts outcome for this discordant group. The Kaplan-Meier plots for time to progression (TTP) and overall survival (OS) are shown in the top right and bottom right panels, respectively. In each plot, lines a, b and c represent H2D-high/FISH-positive, H2D-low/FISH-positive and H2D-low/FISH-negative, respectively.

The lower left panel of FIG. 33 shows that these results cannot be explained by a number of patients in the discordant group falling very close to the FISH cutoff. The H2D-low/FISH-positive subgroup showed a similar range and median of FISH scores to the H2D-high/FISH-positive subgroup. These results are consistent with the idea that in tumors largely driven by HER2 receptor activity, the highly quantitative measure of HER2 homodimer content (H2D) is more predictive than a measure of gene copy number (FISH), which strongly influences but does not have a one-to-one relationship with HER2 protein levels.

FIG. 34 shows how optimal cutoffs were established for H2T measures that were most predictive of TTP. Cutoff values are shown in units of $\log_{10}(H2T)$. The optimal cutoff based on these data was chosen as the one with the lowest p-value, $\log_{10}(H2T)$ 1.2.

Figure 35:
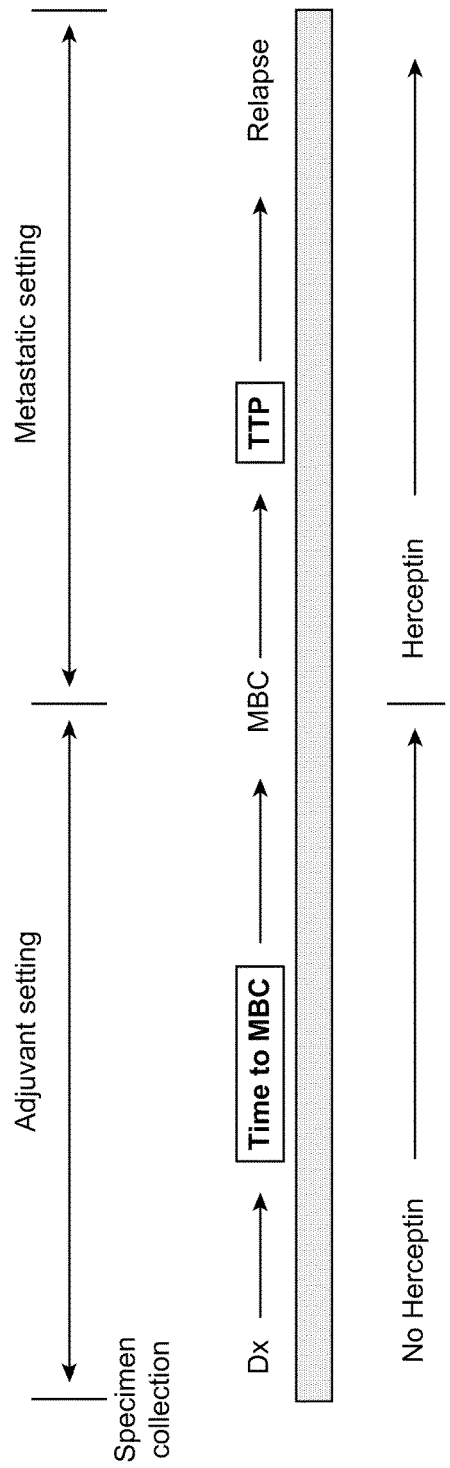

FIG. 35 shows the progression of breast cancer from the initial surgery (and specimen collection) through the adjuvant setting in which no trastuzumab is given, to metastatic breast cancer, through treatment with trastuzumab and the time to progression to relapse. The bottom panel of FIG. 35 shows the Cox proportional hazards analysis for disease-free survival of the patients described in FIG. 29 with the variables H2T, H2D, and H2D/H2T. In the absence of trastuzumab, DFS was not significantly different between the tertiles of H2T (FIG. 29B; trend p=0.2). However, tertiles of H2D or H2D/H2T showed a significant difference in DFS (trend p=0.048, 0.026, respectively) with the lowest H2D or lowest H2D/H2T tertiles showing longest DFS. When considered as continuous variables (FIG. 35), log (H2T) trends towards a prediction of worse outcome with higher H2T (HR=1.4/log(H2T); p=0.09), but log(H2D) and H2D/H2T are significant predictors of outcome with higher values correlating with worse outcome (p=0.02 and 0.03, respectively). This would be consistent with the idea that a measure of dimer levels or a proportion of HER2 involved in dimers, measures more indicative of actively signaling receptor, could be more accurate at predicting disease recurrence than the measurement of total HER2.

Figure 36:
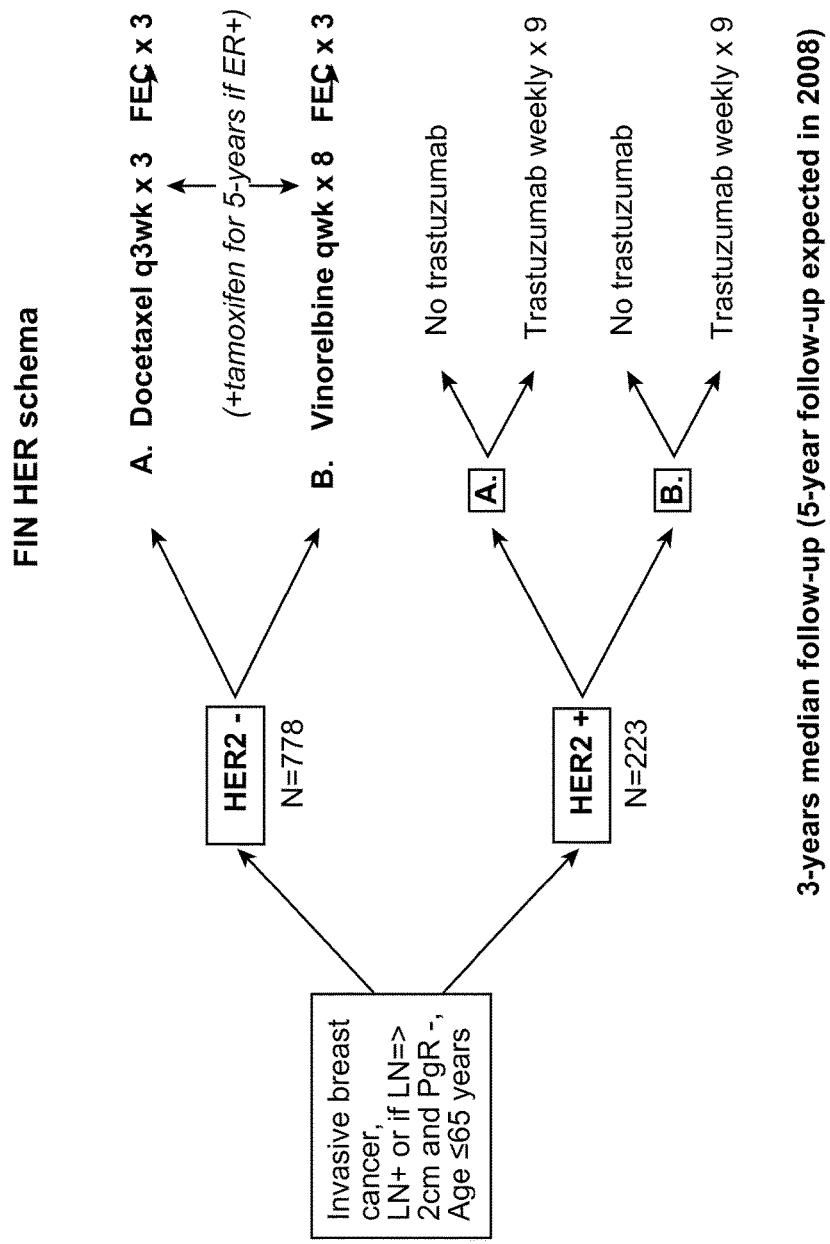

FIG. 36 outlines the study design for a clinical trial called FIN HER, which was designed to test the use of 9 weeks of trastuzumab with chemotherapy versus chemotherapy alone in the adjuvant setting for Her-2-positive breast cancer.

Figure 37:
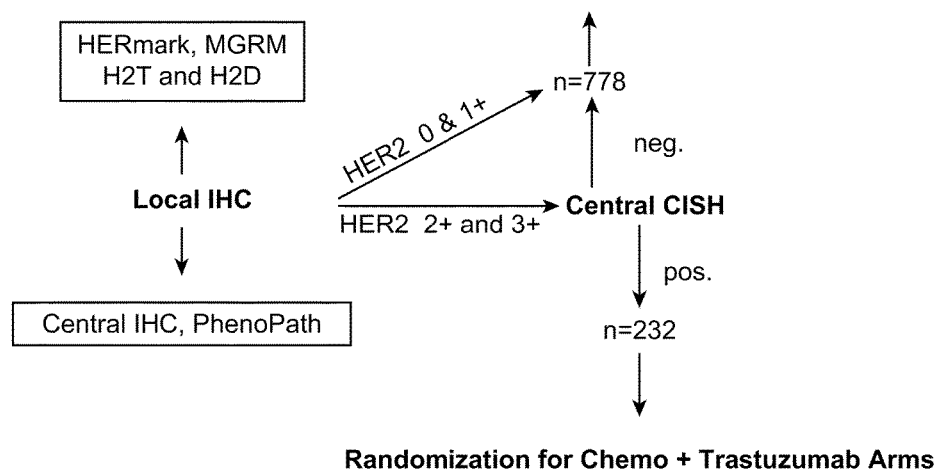

FIG. 37 shows how inclusion into the trastuzumab randomization arms was determined using a combination of standardized IHC and chromogenic in situ hybridization (CISH).

Figure 38:
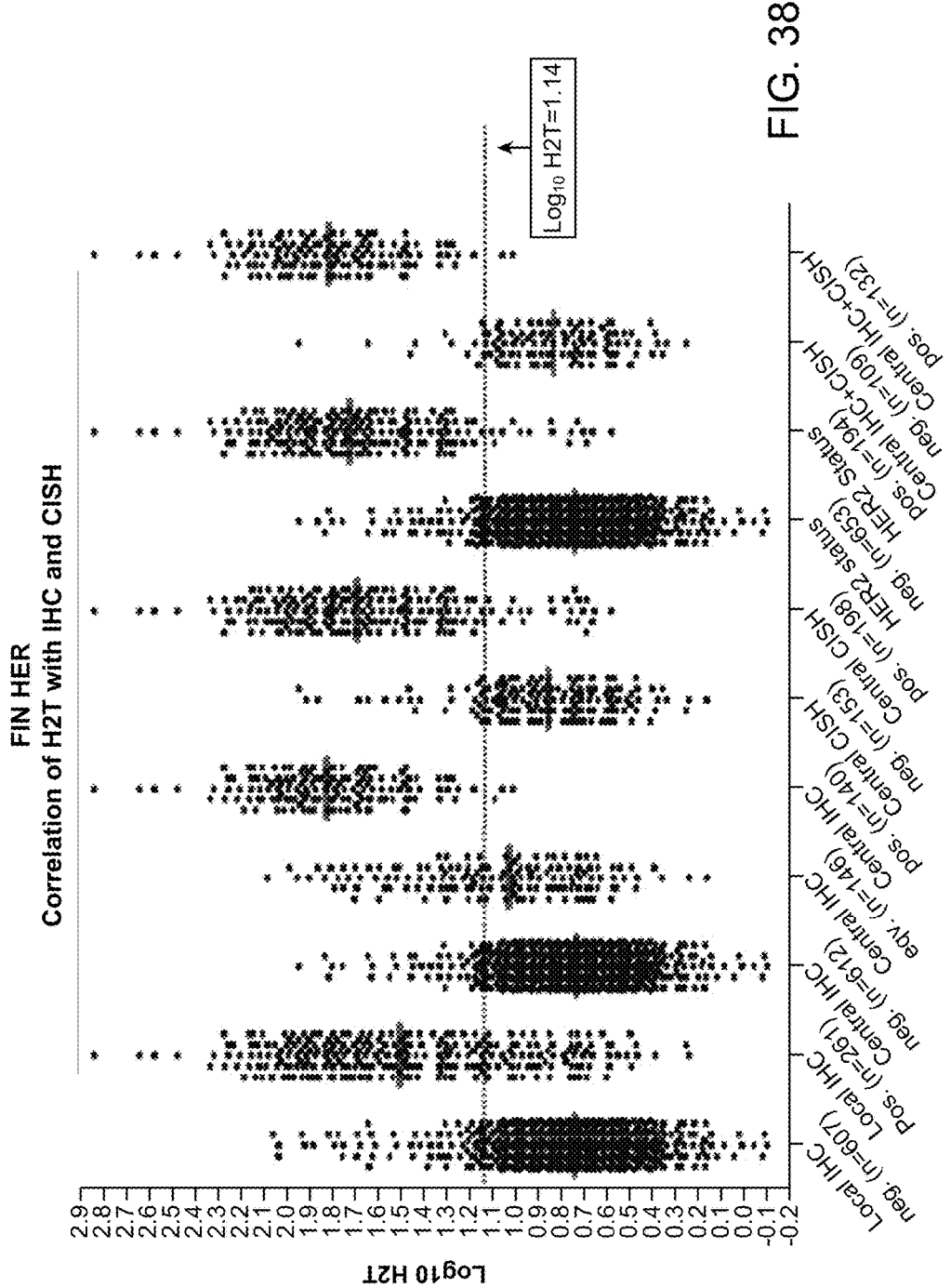

FIG. 38 shows a comparison of HERMark measures with IHC and CISH. FFPE tumor slides from the FIN HER study were obtained and assayed for H2T and H2D using the HERMark assay. The optimal cutoff for H2T ($\log_{10}$H2T=1.14) is shown by the horizontal line. (This cutoff value was derived as shown in FIG. 34 but differs slightly in numerical value due only to a change in scale from the research and development scaling system to the commercial scaling system.) "Local IHC" results were scored by different laboratories when the samples were first obtained; "Central IHC" results were scored by a single central laboratory for all samples in this cohort. As patients were subdivided more stringently, organized from left to right in FIG. 38, the cutoff log(H2T)=1.14 appears to be increasingly concordant in the order of local IHC<central IHC<Central CISH<both Central IHC and Central CISH. This last comparison shows the best concordance with the H2T cutoff and the most stringent subgrouping using currently available technology: those that are both central IHC and CISH negative versus those that are both central IHC and CISH positive.

FIG. 39 shows multivariate Cox proportional hazard analysis for H2T, H2D and the ratio of Her-2 homodimers to total Her-2 (H2D/H2T) from approximately 200 of the 232 CISH-positive patients randomized into chemotherapy with versus without trastuzumab that were available for HER-Mark assays. H2T, H2D and H2D/H2T were first tested as independent correlates of responsiveness to trastuzumab as measured by time to distant recurrence (TDR), time to any recurrence (TAR) and time to death (TD). Neither H2T nor H2D were found to be independent correlates of outcomes. However increasing H2D/H2T was found to be an independent correlate of TAR with marginal significance (p=0.05) and trending towards significance in TDR (p=0.07).

Figure 40:
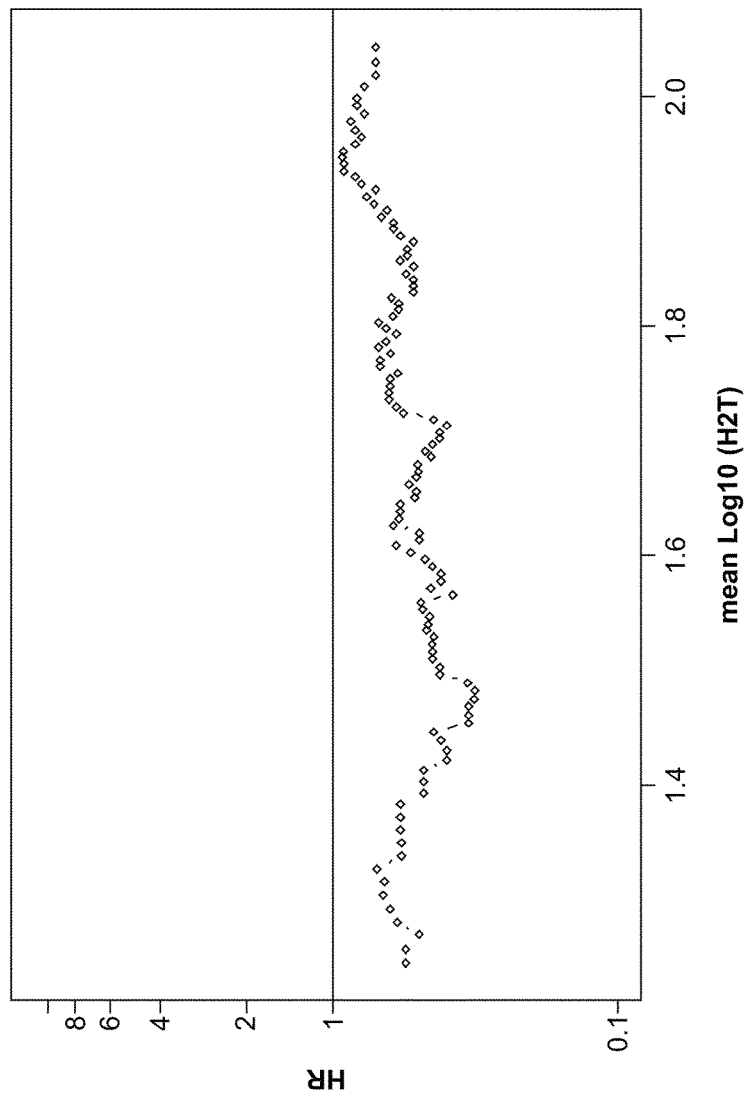
Figure 41:
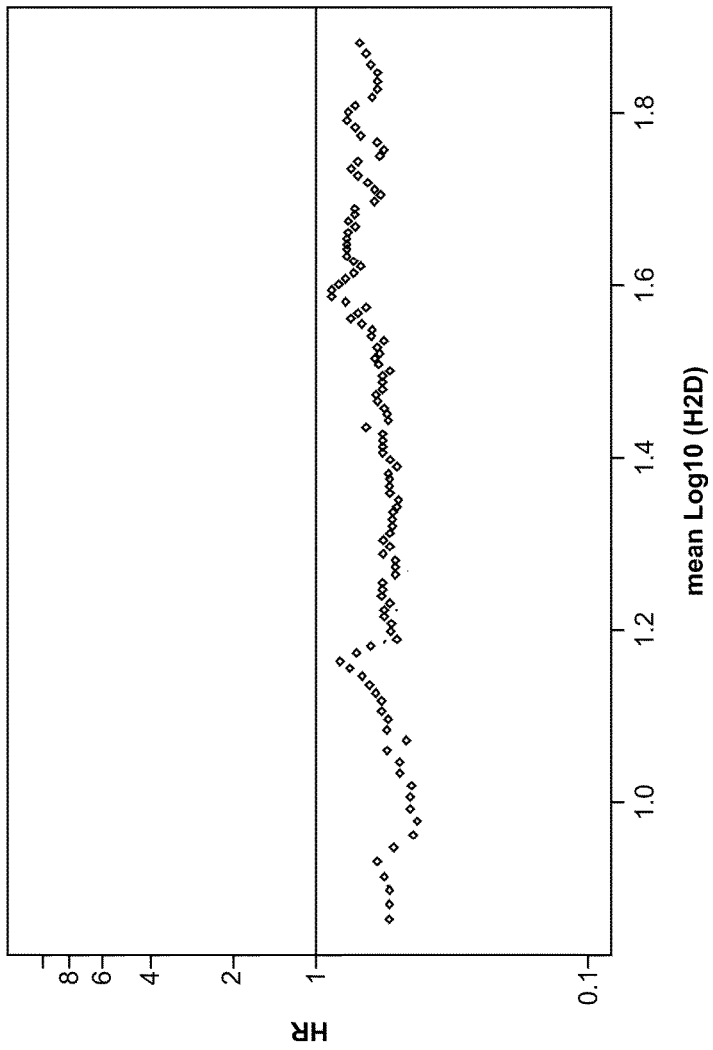
Figure 42:
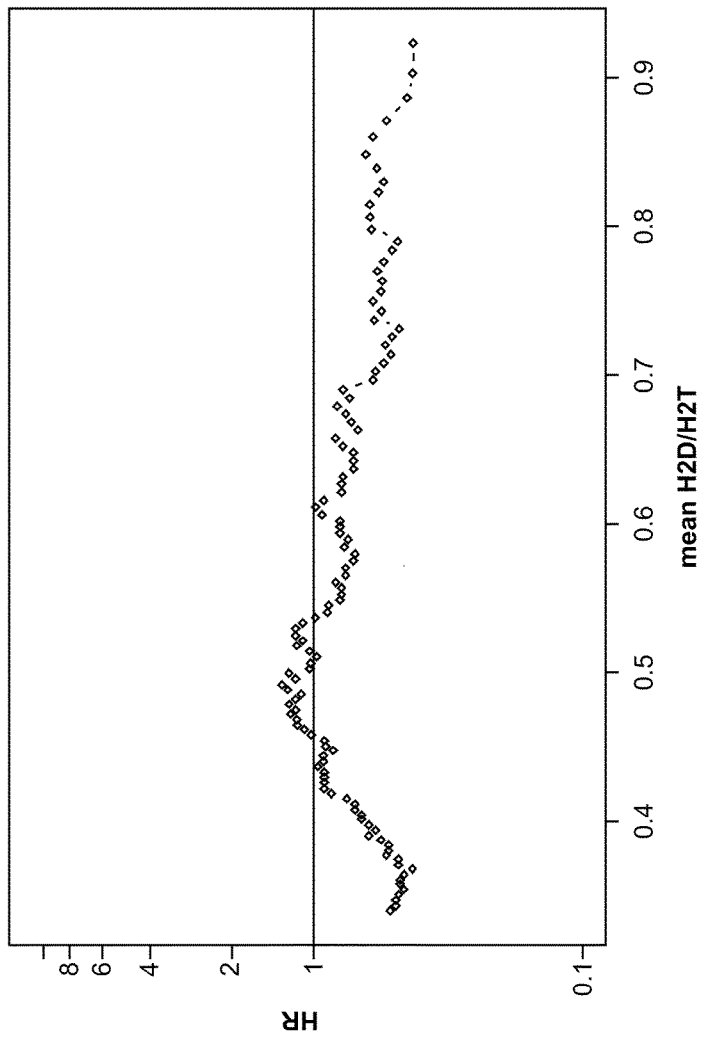

FIG. 40 shows a subpopulation treatment effect pattern plot (STEPP) analysis that examines the hazard ratios for treated versus control subjects across the distribution of H2T with respect to time to distant recurrence (TDR). The purpose of this analysis is to identify a subgroup with enhanced or reduced benefit from the addition of trastuzumab to chemotherapy versus chemotherapy alone. Hazard ratios between trastuzumab plus chemotherapy versus chemotherapy alone were assessed for bin sizes of 80 patients, scanning from the lowest to highest 80 for each variable of interest. FIGS. 40-42 show the results of these calculations with the hazard ratio for each bin plotted versus the mean value for each variable within the bin. Within this CISH+ cohort, there may be a subset with very high H2T that show a reduced benefit from trastuzumab.

FIG. 41 shows the same analysis as described for FIG. 40 except for H2D rather than H2T. All patient bins appear to benefit from trastuzumab.

FIG. 42 shows the same analysis as described in FIG. 40, analyzing H2D/H2T. There may be a subset with H2D/H2T 0.5 that show a reduced benefit from trastuzumab.

Figure 43:
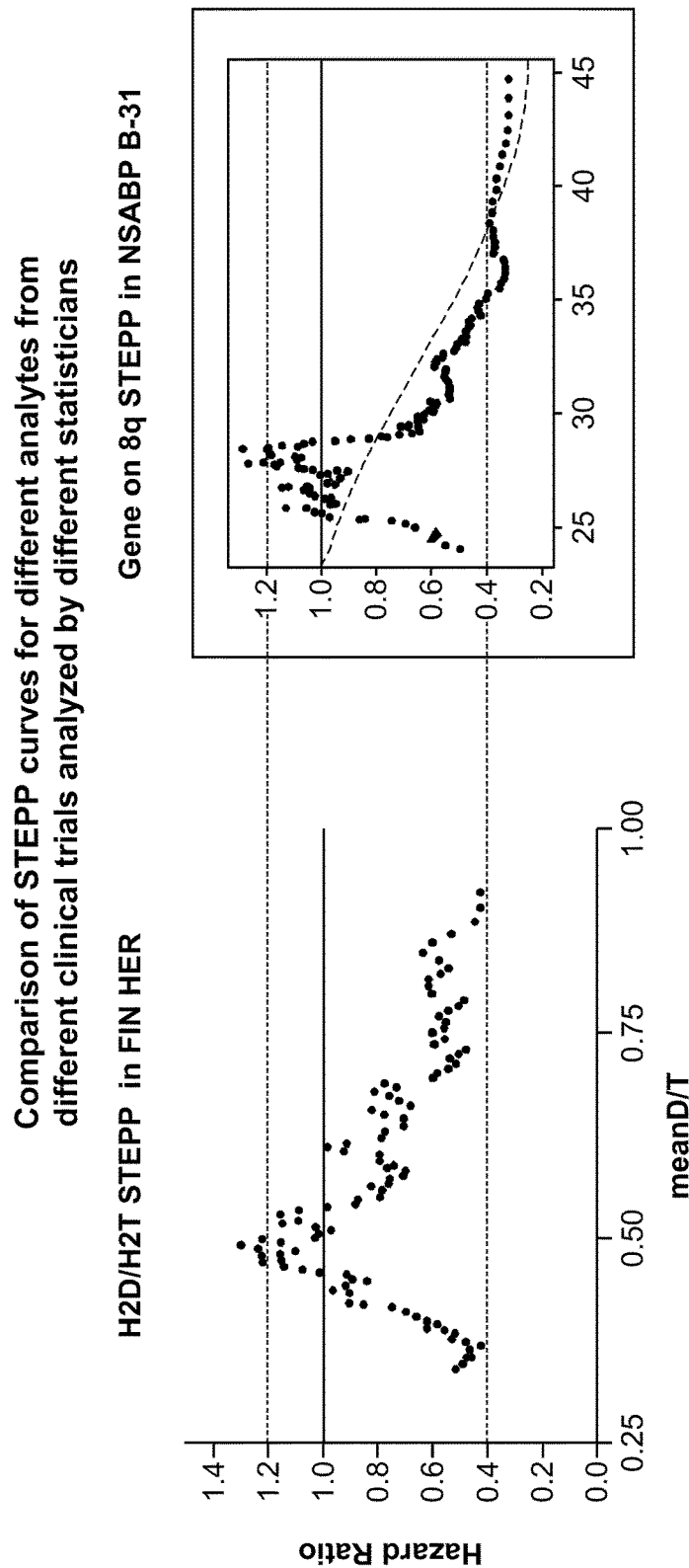

FIG. 43 shows the STEPP plot from FIG. 42 on the left, except with the y-axis on a linear scale. The right panel shows a similar analysis of a gene found on the long arm of chromosome 8, which has been shown to have a significant interaction with trastuzumab treatment in the NSABP B-31 trial. As shown from the right panel of FIG. 43, the dotted line curve fit moves from a hazard ratio of 1 (no benefit) for low expression to a hazard ratio of 0.4 (trastuzumab benefit) with high expression. The comparison suggests that the H2D/H2T may be useful in identifying patients with lesser and greater benefit from the addition of trastuzumab to chemotherapy. Further, those with reduced benefit may be candidates for additional therapies.

DETAILED DESCRIPTION OF THE INVENTION

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

"Antibody" means an immunoglobulin that specifically binds to, and is thereby defined as complementary with, a particular spatial and polar organization of another molecule. The antibody can be monoclonal, polyclonal, or recombinant and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. Antibodies may also be single-chain antibodies or an antigen-binding fragment thereof, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Guidance in the production and selection of antibodies and antibody derivatives for use in immunoassays, including such assays employing releasable molecular tag (as described below) can be found in readily available texts and manuals, e.g., Harlow and Lane, 1988, *Antibodies: A Laboratory Manual*, Cold Spring Harbor Laboratory Press, New York; Howard and Bethell, 2001, *Basic Methods in Antibody Production and Characterization*, CRC Press; Wild, ed., 1994, *The Immunoassay Handbook*, Stockton Press, New York.

"Antibody binding composition" means a molecule or a complex of molecules that comprises one or more antibodies, or antigen-binding fragments that bind to a molecule, and derives its binding specificity from such antibody or antibody-binding fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds. Generally, a protein has several or many different antigenic determinants and reacts with antibodies of different specificities. A preferred antigenic determinant is a phosphorylation site of a protein.

"Binding compound" shall refer to an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins. In one aspect, a binding compound, which can be represented by the formula below, comprises one or more molecular tags attached to a binding moiety.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids and organic molecules having a molecular weight of up to about 1000 daltons and containing atoms selected from the group consisting of hydrogen, carbon, oxygen, nitrogen, sulfur and phosphorus. Preferably, binding moieties are antibodies or antibody binding compositions.

"Cancer" and "cancerous" refer to or describe the physiological condition organism, including mammals, that is typically characterized by unregulated cell growth. Examples of cancer include, but are not limited to, carcinoma, lymphoma, blastoma, sarcoma and leukemia. More particular examples of such cancers include squamous cell cancer, lung cancer, e.g., small-cell lung cancer or non-small cell lung cancer; gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer.

"Chemotherapeutic agent" means a chemical substance, primarily a cytotoxic or cytostatic agent, that is used to treat a condition, particularly cancer. Chemotherapeutic agents shall include such compounds as paclitaxel, as set forth herein.

A "cleavable linkage," as used herein, refers to a chemical linking group that may be cleaved under conditions that do not degrade the structure or affect detection characteristics of a molecular tag connected to a binding moiety with the cleavable linkage.

A "cleavage-inducing moiety," or "cleaving agent," as used herein, is a group that produces an active species that is capable of cleaving a cleavable linkage, preferably by oxidation. Preferably, the active species is a chemical species that exhibits short-lived activity so that its cleavage-inducing effects are only in the proximity of the site of its generation.

A "cleaving probe," as used herein, refers to a reagent that comprises a cleavage-inducing moiety as defined herein and an antibody binding composition, an antibody, a peptide, a peptide or non-peptide ligand for a cell surface receptor, a protein, such as biotin or streptavidin, an oligonucleotide, an oligonucleotide analog, such as a peptide nucleic acid, a lectin or any other molecular entity that is capable of specifically binding to a target protein or molecule or stable complex formation with an analyte of interest, such as a complex of proteins.

"eTag™", "VeraTag™" and "eTag™ assay" are used interchangeably and refer to single and multiplexed and multi-label assays, materials, methods and techniques for performing and utilizing such assays, including but not limited to reagents, analytical procedures and software related to those assays. Such assays are disclosed in this application as well as in U.S. Pat. No. 7,105,308, which is incorporated by reference herein including any drawings.

"FFPE" shall refer to a group of cells or quantity of tissue that are fixed, particularly conventional formalin-fixed paraffin-embedded samples. Such samples are typically, without limitation, used in an assay for receptor complexes in the form of thin sections, e.g. 3-10 µm thick, of fixed tissue mounted on a microscope slide or equivalent surface. Such samples also typically undergo a conventional re-hydration procedure, and optionally, an antigen retrieval procedure as a part of, or preliminary to, assay measurements.

"Hazard ratio", as used herein, refers to a statistical method used to generate an estimate for relative risk. "Hazard ratio" is the ratio between the predicted hazard of one group versus another group. For example, patient populations treated with versus without a Her-2 acting agent can be assessed for whether or not the Her-2 acting agent is effective in increasing the time to distant recurrence of disease. The hazards ratio can then be compared to an independent measure, such as the ratio of Her-2 homodimer to total Her-2. At Her-2 homodimer to total Her-2 ratios at which the hazards ratio is less than one, treating with a Her-2 acting agent has a greater chance of efficacy. At Her-2 homodimer to total Her-2 ratios at which the hazards ratio is indistinguishable from one, treating with a Her-2 acting agent has a lower chance of efficacy.

"Her-2", "ErbB2", "c-Erb-B2", "HEL", "Her2" and "neu" are used interchangeably herein and refer to native Her-2, and allelic variants thereof, as described, for example, in Semba et al., 1985, P.N.A.S. USA 82:6497-650 and Yamamoto et al., 1986, Nature 319:230-234 and GenBank accession number X03363. Unless indicated otherwise, the terms "Her-2", "ErbB2", "c-Erb-B2", "HER2" and "Her2" when used herein refer to the human protein. The gene encoding Her2 is referred to herein as "erbB2." As used herein, H2T shall refer to total Her-2 expression as shown, for example without limitation, by VeraTag™ assay.

"Her-2-acting agent," as used herein, refers to a compound that can inhibit a biological activity of Her-2 or a Her-2 expressing cell or a Her-2 positive cancer cell. Such biological activities include, but are not limited to, dimerization, autophosphorylation, phosphorylation of another receptor, signal transduction and the like. Biological activities can include, without limitation, cell survival and cell proliferation, and inhibition of such activities by a Her-2 acting agent could be direct or indirect cell killing (eg, ADCC), disruption of protein complexes or complex formation, modulation of protein trafficking or enzyme inhibition. Biological activities can also include patient response as set forth in this application. Exemplary Her-2-acting agents include, but are not limited to, the large molecules 4D5 and trastuzumab and small molecules such as AEE-788 and lapatinib.

"Her-2 homodimer" in reference to cell surface Her-2 membrane receptors means a complex of two or more membrane-bound Her-2 proteins. Dimers usually consist of two receptors in contact with one another. Dimers may be created in a cell surface membrane by passive processes, such as Van der Waal interactions, and the like, or dimers may be created by active processes, such as by ligand-induced dimerization, covalent linkages, interaction with intracellular components or the like. See, e.g., Schlessinger, 2000, Cell 103:211-225. As used herein, the term "dimer" is understood to refer to "cell surface membrane receptor dimer," unless understood otherwise from the context. As used herein, H22D shall refer to quantified dimer as shown, for example without limitation, by VeraTag™ assay.

"Her-2 homodimer to total Her-2 ratio" refers to a measure that describes the amount of Her-2 homodimers divided by the total amount of Her-2 in a sample from a subject's tissue according to any single quantitative method available to one skilled in the art.

A "Her-2 positive" cancer, cancer cell, subject or patient, as used herein, refers to a cancer, cell subject or patient exhibiting a score of at least 2 when using a HercepTest® (DakoCytomation California Inc., Carpenteria, Calif.) or a cancer, cancer cell, subject or patient that has been identified as such by FISH. In certain embodiments, the Her-2 positive cell exhibits a score of at least 2+ or 3+ using HercepTest®.

"High" refers to a measure that is greater than normal, greater than a standard such as a predetermined measure or a subgroup measure or that is relatively greater than another subgroup measure. For example, high Her-2 refers to a measure of Her-2 that is greater than a normal Her-2 measure. A normal Her-2 measure may be determined according to any method available to one skilled in the art. High Her-2 may also refer to a measure that is equal to or greater than a predetermined measure, such as a predetermined cutoff High Her-2 may also refer to a measure of Her-2 wherein a high Her-2 subgroup has relatively greater levels of Her-2 than another subgroup. For example, without limitation, according to the present specification, two distinct patient subgroups can be created by dividing samples around a mathematically determined point, such as, without limitation, a median, thus creating a subgroup whose measure is high (i.e., higher than the median) and another subgroup whose measure is low. Her-2 can be measured by any method known to one skilled in the art such as, for example, without limitation, using eTag™ or using any standard immunohistochemical (IHC) method such as HercepTest®. As another example, high Her-2 homodimers refers to a measure of Her-2 homodimers that is greater than a normal measure of Her-2 homodimers in a particular set of samples or patients that are Her-2 positive. A normal Her-2 homodimer measure may be determined according to any method available to one skilled in the art. High Her-2 homodimers may also refer to a measure that is greater than a predetermined measure, such as a predetermined cutoff High Her-2 homodimers may also refer to a measure of Her-2 homodimers wherein a high Her-2 homodimer subgroup has a relatively higher level of Her-2 homodimers than another subgroup. Her-2 homodimers can be measured by any method known in the art such as Fluorescence resonance energy transfer (FRET), Bioluminescent resonance energy transfer (BRET), proximity ligation assay (PLA), dimer-specific antibodies or eTag™ or any other method that is well known to one skilled in the art. As another example, high Her-2 homodimer to total Her-2 ratio may refer to the one or more subgroups of Her-2 homodimer to total Her-2 ratios that have measures greater than either intermediate or low ratio subgroups. High Her-2 homodimer to total Her-2 ratios may be determined according to any individual quantitative method available to one skilled in the art.

"Intermediate", as used herein, refers to a measure that is greater than "low" and less than "high". For example, "intermediate" may be used to describe one or more of the at least 3 subgroups that fall in the middle range of measures of Her-2 homodimer to total Her-2 ratios.

"Likely to," as used herein, refers to an increased probability that an item, object, thing or person will occur. Thus, in one example, a subject that is likely to respond to treatment with trastuzumab has an increased probability of responding to treatment with trastuzumab relative to a reference subject or group of subjects.

"Long," as used herein, refers to a time measure that is greater than normal, greater than a standard such as a predetermined measure or a subgroup measure that is relatively longer than another subgroup measure. For example, with respect to a patient's longevity, a long time progression refers to time progression that is longer than a normal time progression. Whether a time progression is long or not may be determined according to any method available to one skilled in the art. Long could include, for example, no progression.

"Low" is a term that refers to a measure that is less than normal, less than a standard such as a predetermined measure or a subgroup measure that is relatively less than another subgroup measure. For example, low Her-2 means a measure of Her-2 that is less than a normal Her-2 measure in a particular set of samples of patients that is Her-2 positive. A normal Her-2 measure may be determined according to any method available to one skilled in the art. Low Her-2 may also mean a method that is less than a predetermined measure, such as a predetermined cutoff Low Her-2 may also mean a measure wherein a low Her-2 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high. Her-2 can be measured by any method known to one skilled in the art such as, for example, without limitation, using the eTag™ method or using any standard immunohistochemical (IHC) method such as HercepTest®. As another example, low Her-2 homodimers means a measure of Her-2 homodimers that is less than a normal measure of Her-2 homodimers in a particular set of samples or patients that is Her-2 positive. Low Her-2 homodimers may also mean a measure that is less than a predetermined measure, such as a predetermined cutoff Low Her-2 homodimers may also mean a measure wherein a low Her-2 homodimer subgroup is relatively less than another subgroup. Her-2 homodimers can be measured by any method known in the art such as Fluorescence resonance energy transfer (FRET), Bioluminescent resonance energy transfer (BRET), proximity ligation assay (PLA), dimer-specific antibodies or eTag™ or any other method that is well known to one skilled in the art. As another example, low Her-2 homodimer to total Her-2 ratio may refer to the one or more subgroups of Her-2 homodimer to total Her-2 ratios that have measures less than either intermediate or high ratio subgroups. Low Her-2 homodimer to total Her-2 ratios may be determined according to any individual quantitative method available to one skilled in the art.

A "molecular tag," as used herein, refers to a molecule that can be distinguished from other molecules based on one or more physical, chemical or optical differences among the molecules being separated, including but not limited to, electrophoretic mobility, molecular weight, shape, solubility, pKa, hydrophobicity, charge, charge/mass ratio, polarity or the like. In one aspect, molecular tags in a plurality or set differ in electrophoretic mobility and optical detection characteristics and can be separated by electrophoresis. In another aspect, molecular tags in a plurality or set may differ in molecular weight, shape, solubility, pKa, hydrophobicity, charge, polarity and can be separated by normal phase or reverse phase HPLC, ion exchange HPLC, capillary electrochromatography, mass spectroscopy, gas phase chromatography or like technique.

"Optimal cutoff" as used herein, refers to the value of a predetermined measure on subjects exhibiting certain attributes that allow the best discrimination between two categories of an attribute. For example, finding a value for an optimal cutoff that allows one to best discriminate between two categories, high H2T expression and low H2T expression, for determining OS (see, eg, FIG. 28). Optimal cutoffs are used to separate the subjects with values lower than or higher than the optimal cutoff to optimize the prediction model, for example, without limitation, to maximize the specificity of the model, maximize the sensitivity of the model, maximize the difference in outcome, or minimize the p-value from hazard ratio or a difference in response.

"Overall survival" or "OS" refers to a time as measured from the start of treatment to death or censor. Censoring may come from a study end or change in treatment. Overall survival can refer to a probability as, for example, a probability when represented in a Kaplan-Meier plot of being alive at a particular time, that time being the time between the start of the treatment to death or censor.

"Photosensitizer" shall mean a light-adsorbing molecule that when activated by light converts molecular oxygen into singlet oxygen.

"RECIST" shall mean an acronym that stands for "Response Evaluation Criteria in Solid Tumours" and is a set of published rules that define when cancer patients improve ("respond"), stay the same ("stable") or worsen ("progression") during treatments. Response as defined by RECIST criteria have been published, for example, at *Journal of the National Cancer Institute*, Vol. 92, No. 3, Feb. 2, 2000 and RECIST criteria may include other similar published definitions and rule sets. One skilled in the art would understand definitions that go with RECIST criteria, as used herein, such as "PR," "CR," "SD" and "PD."

"Relative fluorescence units" or "RFUs" are used interchangeably and shall refer to the time integral of a particular capillary electrophoresis peak using arbitrary fluorescence units in comparison to a standard. With respect to eTag™, the RFU is proportional to the concentration of eTag™ injected into capillary electrophoresis with some expected variability introduced by, for example, injection and capillary differences.

"Relative peak area" or "RPA" are used interchangeably and shall refer to the ratio between an RFU of a particular eTag™ and an RFU of a known internal fluorescence standard of known and constant concentration.

"Responsiveness," to "respond" to treatment, and other forms of this verb, as used herein, refer to the reaction of a subject to treatment with a Her-2-acting agent. As an example, a subject responds to treatment with a Her2-acting agent if growth of a tumor in the subject is retarded about 10%, 20%, 30%, 40%, 50%, 60%, 70%, 80%, 90% or more. In another example, a subject responds to treatment with a Her-2-acting agent if a tumor in the subject shrinks by about 5%, 10%, 20%, 30%, 40%, 50% or more as determined by any appropriate measure, e.g., by mass or volume. In another example, a subject responds to treatment with a Her2-acting agent if the subject experiences a life expectancy extended by about 5%, 10%, 20%, 30%, 40%, 50% or more beyond the life expectancy predicted if no treatment is administered. In another example, a subject responds to treatment with a Her-2-acting agent if the subject has an increased disease-free survival, overall survival or increased time to progression. Several methods may be used to determine if a patient responds to a treatment including the RECIST criteria, as set forth above.

"Sample" or "tissue sample" or "patient sample" or "patient cell or tissue sample" or "specimen" each refer to a collection of similar cells obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

"Short," as used herein, refers to a time measure that is shorter than normal, shorter than a standard such as a predetermined measure or a subgroup measure that is relatively shorter than another subgroup measure. For example, with respect to a patient's longevity, a short time progression refers to time progression that is shorter than a normal time progression. Whether a time progression is short or not may be determined according to any method available to one skilled in the art.

As used herein, "significant event" shall refer to an event in a patient's disease that is important as determined by one skilled in the art. Examples of significant events include, for example, without limitation, primary diagnosis, death, recurrence, the determination that a patient's disease is metastatic, relapse of a patient's disease or the progression of a patient's disease from any one of the above noted stages to another. A significant event may be any important event used to assess OS, TTP and/or using the RECIST or other response criteria, as determined by one skilled in the art.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

As used herein, "time course" shall refer to the amount of time between an initial event and a subsequent event. For example, with respect to a patient's cancer, time course may relate to a patient's disease and may be measured by gauging significant events in the course of the disease, wherein the first event may be diagnosis and the subsequent event may be metastasis, for example.

"Time to progression" or "TTP" refers to a time as measured from the start of the treatment to progression or a cancer or censor. Censoring may come from a study end or from a change in treatment. Time to progression can also be represented as a probability as, for example, in a Kaplein-Meier plot where time to progression may represent the probability of being progression free over a particular time, that time being the time between the start of the treatment to progression or censor.

"Treat," "treatment," and other forms of this word refer to the administration of a Her-2-acting agent to impede growth of a cancer, to cause a cancer to shrink by weight or volume, to extend the expected survival time of the subject and or time to progression of the tumor or the like.

"Unlikely to" refers to a decreased probability that an event, item, object, thing or person will occur with respect to a reference. Thus, a subject that is unlikely to respond to treatment with paclitaxel in addition to trastuzumab has a decreased probability of responding to treatment with paclitaxel and trastuzumab relative to a reference subject or group of subjects.

The invention provides a method for determining whether a subject with a cancer is likely to respond to treatment with a Her-2-acting agent and/or for predicting a time course of disease and/or a probability of a significant event in the time course of disease in a subject with a cancer. In certain embodiments, the method comprises detecting a biomarker or combination of biomarkers associated with responsiveness to treatment with a Her-2-acting agent as described hereinafter, and determining whether the subject is likely to respond to treatment with the Her2-acting agent. In certain embodiments, the methods comprise detecting a biomarker or combination of biomarkers and predicting a time course associated with progression of disease or a probability of a significant event in the time course of disease in a subject with cancer.

In one aspect, the invention is drawn to a method for determining whether a subject with a cancer is likely to respond to treatment with a Her-2-acting agent. In another aspect, the invention is drawn to a method for predicting a time course of disease. In another aspect, the method is drawn to a method for predicting a probability of a significant event in the time course of the disease.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from metastatic disease to death. In a preferred embodiment, the significant event is the progression from metastatic disease to relapse. In a preferred embodiment, the significant event is the progression from relapse to death. In certain embodiments, the time course is measured with respect to overall survival rate, time to progression and/or using the RECIST or other response criteria.

In certain embodiments, the method comprises detecting in a biological sample from the subject's cancer the amount of Her-2 and/or Her-2 homodimers wherein if the amount of Her-2 and/or Her-2 homodimers is high, then the patient is likely to respond to the Her-2 acting agent and/or the patient has a long time course. In other embodiments, the cancer is breast cancer. In other embodiments, the breast cancer is metastatic. In certain embodiments, the Her-2 acting agent is trastuzumab. In certain embodiments, the assay is performed with an eTag™ assay. In certain embodiments, likeliness to respond is measured with respect to overall survival rate, time to progression and/or using the RECIST or other response criteria.

In certain embodiments, a predetermined measure is created by dividing patient samples into at least two patient subgroups. In certain embodiments, the number of subgroups is two so that the patient sample is divided into a subgroup of patients whose Her-2 and/or Her-2 homodimers is high and a subgroup whose Her-2 and/or Her-2 homodimers is low. In certain embodiments, the amount of Her-2 and/or Her-2 homodimers in the subject are compared to either the high subgroup or the low subgroup; if the amount of Her-2 and/or Her-2 homodimers in the patient are high, then the patient is likely to respond to a Her-2 acting agent and/or the patient is likely to have a long time course. In certain embodiments, the number of subgroups is greater than two, including, without limitation, three subgroups, four subgroups, five subgroups and six subgroups. In certain embodiments, likeliness to respond is measured with respect to overall survival rate, time to progression and/or using the RECIST criteria. In certain preferred embodiments, the Her-2 acting agent is trastuzumab.

In certain embodiments, the predetermined measure is an optimal cutoff. Such optimal cutoffs are disclosed herein, and certain embodiments of the invention are meant to include amounts that are approximate to the amounts mentioned and disclosed herein. In certain embodiments, the amount of Her-2 and/or Her-2 homodimers in the subject are compared to the optimal cutoff; if the amount of Her-2 and/or Her-2 homodimers in the patient are high, then the patient is likely to respond to a Her-2 acting agent and/or the patient's time course is likely to be long. In another embodiment, if the amount of Her-2 is high, then the patient is likely to respond to a Her-2 acting agent and/or the time course is likely to be long. In another embodiment, if the amount of Her-2 is high, and the amount of Her-2 homodimers and/or the ratio of Her-2 homodimers to Her-2 are low, then the patient is likely to respond to a Her-2 acting agent and/or the time course is likely to be long. In another embodiment, if the amount of Her-2 is high and the amount of Her-2 dimers is high, then the patient is likely to respond to a Her-2 acting agent and/or the time course is likely to be long.

In another aspect, the invention is drawn to a method for determining whether a subject with a Her-2 positive cancer is likely to respond to treatment with a Her-2-acting agent and/or the time course of disease is long. In another aspect, the invention is drawn to a method for predicting a time course of disease in a subject with a Her-2 positive cancer. In another aspect, the invention is drawn to a method for predicting the probability of a significant event in a subject with a Her-2 positive cancer.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from metastatic disease to death. In a preferred embodiment, the significant event is the progression from metastatic disease to relapse. In a preferred embodiment, the significant event is the progression from relapse to death. In certain embodiments, the time course is measured with respect to overall survival rate, time to progression and/or using the RECIST or other response criteria.

In certain embodiments, the method comprises measuring in a biological sample from the subject's cancer an amount of Her-2 and/or Her-2 homodimers, wherein if the amount of Her-2 and/or Her-2 homodimers is high, then the patient is likely to respond to the Her-2 acting agent and/or the patient has a long time course. In certain embodiments, the biological sample comprises FFPEs. In certain embodiments, the subject's cancer is breast cancer. In certain embodiments, the breast cancer is metastatic. In certain embodiments, the Her-2-acting agent is trastuzumab. In certain embodiments, an amount of Her-2 is measured. In certain embodiments, an amount of Her-2 homodimers is measured. In certain embodiments, the amount of Her-2 homodimers is measured using an assay capable of measuring and/or quantifying an amount of protein-protein interactions in a sample. In certain embodiment, the assay is the eTag™ assay. In certain embodiments, likeliness to respond is measured with respect to overall survival rate, time to progression and/or using the RECIST criteria.

In certain embodiments, a predetermined measure is created by dividing patient samples into at least two patient subgroups. In certain embodiments, the number of subgroups is two so that the patient sample is divided into a subgroup of patients whose Her-2 and/or Her-2 homodimers is high and a subgroup whose Her-2 and/or Her-2 homodimers is low; the amount of Her-2 and/or Her-2 homodimers in the subject are compared to either the high subgroup or the low subgroup; if the amount of Her-2 and/or Her-2 homodimers in the patient are high, then the patient is likely to respond to a Her-2 acting agent and/or the patient is likely to have a long time course. In certain embodiments, the number of subgroups is greater than two, including, without limitation, three subgroups, four subgroups, five subgroups and six subgroups. In certain embodiments, likeliness to respond or time course is measured with respect to overall survival rate, time to progression and/or using the RECIST criteria. In certain preferred embodiments, the Her-2 acting agent is trastuzumab.

In certain embodiments, the predetermined measure is an optimal cutoff. Such optimal cutoffs are disclosed herein, and certain embodiments of the invention are meant to include amounts that are approximate to the amounts mentioned and disclosed herein. In certain embodiments, the amount of Her-2 and/or Her-2 homodimers in the subject are compared to the optimal cutoff; if the amount of Her-2 and/or Her-2 homodimers in the patient are high, then the patient is likely to respond to a Her-2 acting agent and/or the patient's time course is likely to be long. In another embodiment, if the amount of Her-2 is high, then the patient is likely to respond to a Her-2 acting agent and/or the time course is likely to be long. In another embodiment, if the amount of Her-2 is high, and the amount of Her-2 homodimers and/or the ratio of Her-2 homodimers to Her-2 is low, then the patient is likely to respond to a Her-2 acting agent and/or the time course is likely to be long. In another embodiment, if the amount of Her-2 is high and the amount of Her-2 homodimers and/or the ratios of Her-2 homodimers to Her-2 is high, then the patient is likely to respond to a Her-2 acting agent and/or the time course is likely to be long.

In another aspect, the invention provides a method for determining whether a subject with Her2-positive cancer is unlikely to respond to treatment with a Her2-acting agent and/or the patient is likely to have a short time course. In certain embodiments, the method comprises detecting in a biological sample from the subject's cancer the amount of Her-2, wherein if the amount of Her-2 is low, the subject is unlikely to respond to treatment with the Her2-acting agent and/or the patient is likely to have a short time course. In certain preferred embodiments, the Her2-acting agent is trastuzumab.

Any method known to one of skill in the art to be useful for determining an amount of Her-2 expression and/or Her-2 homodimers can be used in accordance with the present invention. For example, any quantitative assay that determines the amount of such expression or dimers can be used to determine how much signal is generated by a cell or cancer, then the signal compared to the signal generated in the eTag™ assay to determine a correspondence between the two assays. Such methods may include, but not necessarily be limited to, FRET, BRET, Biomolecular Fluorescence Complementation and Proximity Ligation Assay.

In certain embodiments, the amounts are determined by contacting a biological sample from a subject with cancer with a binding compound having a molecular tag attached thereto by a cleavable linkage and a cleaving probe having a cleavage inducing-moiety and detecting whether and what molecular tag is released. In certain embodiments, the binding compound and the cleaving probe each specifically binds Her-2. In certain embodiments, the cleaving probe and the binding probe do not both bind the same epitope. In certain embodiments, if the binding compound is within an effective proximity of the cleavage-inducing moiety of the cleaving probe, the cleavage-inducing moiety cleaves the cleavable linker so that the molecular tag is released. In certain embodiments, the molecular tag released if Her-2 homodimers are present is distinguishable from the molecular tag released if Her-2 monomers are present.

In certain embodiments, activating the cleavage-inducing moiety cleaves the cleavable linker. In certain embodiments, the binding compound specifically binds a Her-2 epitope. In certain embodiments, the binding compound comprises an antibody or antigen-binding fragment. In certain embodiments, the binding compound specifically binds a Her-2 ligand binding site. In certain embodiments, the binding compound comprises a Her-2 ligand. In certain embodiments, the binding compound and the cleaving probe bind the same Her-2 epitope.

In certain embodiments, the step of measuring the amounts of one or more Her-2 homodimers comprises the following steps: (i) providing for each of the one or more Her-2 homodimers a cleaving probe specific for a first Her-2 protein in each of the one Her-2 homodimers, each cleaving probe having a cleavage-inducing moiety with an effective proximity; (ii) providing one or more binding compounds specific for a second protein of each of the one or more Her-2 homodimers, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probes, the binding compounds, and the one or more complexes such that cleaving probes specifically bind to first proteins of the Her-2 homodimers and binding compounds specifically bind to the second proteins of the Her-2 homodimers and such that cleavable linkages of the binding compounds are within the effective proximity of cleavage-inducing moieties of the cleaving probes so that molecular tags are released; and (iv) separating and identifying the released molecular tags to determine the presence or absence or the amount of the Her-2 homodimers.

The invention relates to Her-2-acting agents. A Her-2-acting agent can be any such agent known to one of skill in the art. In certain embodiments the Her2-acting agent is selected from the group consisting of 4D5, trastuzumab, AEE-788 and lapatinib. In a preferred embodiment, the Her-2-acting agent is trastuzumab (Herceptin®). See, e.g., Goldenberg, 1999, *Clin Ther.* 21:309-18; and Shak, 1999, *Semin Oncol.* 26:71-7.

Samples containing Her-2 and/or Her-2 homodimers suitable for use as biomarkers may come from a wide variety of sources, including cell cultures, animal or plant tissues, patient biopsies or the like. Preferably, samples are human patient samples. Samples are prepared for assays of the invention using conventional techniques, which may depend on the source from which a sample is taken. For biopsies and medical specimens, guidance is provided in the following references: Bancroft JD & Stevens A, eds. 1977, *Theory and Practice of Histological Techniques*, Churchill Livingstone, Edinburgh; Pearse, 1980, *Histochemistry. Theory and applied.* $4^{th}$ ed., Churchill Livingstone, Edinburgh.

In the area of cancerous disease status, examples of patient tissue samples that may be used include, but are not limited to, breast, prostate, ovary, colon, lung, endometrium, stomach, salivary gland or pancreas. The tissue sample can be obtained by a variety of procedures including surgical excision, aspiration or biopsy. The tissue may be fresh or frozen. In one embodiment, assays of the invention are carried out on tissue samples that have been fixed and embedded in paraffin and a step of deparaffination is be carried out. A tissue sample may be fixed (i.e., preserved) by conventional methodology. See, e.g., Lee G. Luna, HT (ASCP) Ed., 1960, *Manual of Histological Staining Method of the Armed Forces Institute of Pathology* $3^{rd}$ edition, The Blakston Division McGraw-Hill Book Company, New York; Ulreka V. Mikel, Ed., 1994, *The Armed Forces Institute of pathology Advanced Laboratory Methods in Histology and Pathology*, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology according to conventional techniques described by the references provided above. Examples of paraffin that may be used include, but are not limited to, Paraplast, Broloid, and Tissuemay. Once the tissue sample is embedded, the sample may be sectioned by a microtome according to conventional techniques. Sections may have a thickness in a range from about three microns to about twelve microns, and preferably, a thickness in a range of from about 5 microns to about 10 microns. In one aspect, a section may have an area of from about 10 $mm^2$ to about 1 $cm^2$. Once cut, the sections may be attached to slides by several standard methods. Examples of slide adhesives include, but are not limited to, silane, gelatin and poly-L-lysine. Paraffin embedded sections may be attached to positively charged slides and/or slides coated with poly-L-lysine.

If paraffin has been used as the embedding material, the tissue sections are generally deparaffinized and rehydrated to water prior to detection of biomarkers. Tissue sections may be deparaffinized by several conventional standard methodologies. For example, xylenes and a gradually descending series of alcohols may be used according to conventional techniques described by the references provided above. Alternatively, commercially available deparaffinizing non-organic agents such as Hemo-De® (CMS, Houston, Tex.) may be used.

Mammalian tissue culture cells, or fresh or frozen tissues may be prepared by conventional cell lysis techniques (e.g., 0.14 M NaCl, 1.5 mM $MgCl_2$, 10 mM Tris-Cl (pH 8.6), 0.5% Nonidet P-40, and protease and/or phosphatase inhibitors as required). For fresh mammalian tissues, sample preparation may also include a tissue disaggregation step, such as crushing, mincing, grinding or sonication.

Many advantages are provided by measuring dimer populations using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: U.S. Pat. Nos. 7,105,308 and 6,627,400; published U.S. Patent Application Nos. 2002/0013126, 2003/0170915, and 2002/0146726; and International Patent Publication No. WO 2004/011900, each of which are incorporated herein by reference in its entirety. For example, a wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio or polarity. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity and are separated by normal phase or reverse phase HPLC, ion exchange HPLC, capillary electrochromatography, mass spectroscopy or gas phase chromatography.

Sets of molecular tags are provided that can be separated into distinct bands or peaks by a separation technique after they are released from binding compounds. Identification and quantification of such peaks provides a measure or profile of the presence and/or amounts of receptor dimers. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

Measurements made directly on tissue samples may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells.

As mentioned above, mixtures containing pluralities of different binding compounds may be provided, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin or any other molecular entity that is capable of specifically binding to a target protein or molecule or stable complex formation with an analyte of interest, such as a Her-2 homodimer. In one aspect, a binding compound can be represented by the following formula:

wherein B is binding moiety; L is a cleavable linkage and E is a molecular tag. In homogeneous assays, cleavable linkage, L, may be an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500 or k is greater than several hundred to as many as several thousand, e.g. 500 to 5000. Usually each of the plurality of different types of binding compounds has a different molecular tag, E. Cleavable linkages, e.g. oxidation-labile linkages, and molecular tags, E, are attached to B by way of conventional chemistries.

Preferably, B is an antibody binding composition that specifically binds to a target, such as an antigenic determinant on Her-2. Antibodies specific for Her-2 epitopes are provided in the examples set forth herein. Antibody compositions are readily formed from a wide variety of commercially available antibodies, either monoclonal or polyclonal. In particular, antibodies specific for epidermal growth factor receptors are disclosed in U.S. Pat. Nos. 5,677,171; 5,772,997; 5,968,511; 5,480,968; 5,811,098, each of which are incorporated by reference in its entirety. U.S. Pat. No. 5,599,681, hereby incorporated by reference in its entirety, discloses antibodies specific for phosphorylation sites of proteins. Commercial vendors, such as Cell Signaling Technology (Beverly, Mass.), Biosource International (Camarillo, Calif.) and Upstate (Charlottesville, Va.) also provide monoclonal and polyclonal antibodies.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety."

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen or the like, but also linkages that are labile to agents that operate throughout a reaction mixture, such as base-labile linkages, photocleavable linkages, linkages cleavable by reduction, linkages cleaved by oxidation, acid-labile linkages and peptide linkages cleavable by specific proteases. References describing many such linkages include Greene and Wuts, 1991, *Protective Groups in Organic Synthesis, Second Edition*, John Wiley & Sons, New York; Hermanson, 1996, *Bioconjugate Techniques*, Academic Press, New York; and U.S. Pat. No. 5,565,324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio) propionate (SPDP), succinimidyloxycarbonyl-α-methyl-α-(2-pyridyldithio)toluene (SMPT) or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol or sodium borohydride. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST) (available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g., 0.1 N hydroxylamine, pH 8.5, for 3-6 hours at 37° C. Such spacers can be introduced by a homobifunctional cross-linking agent such as ethylene glycol bis(succinimidylsuccinate) (EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages also include those disclosed in U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in U.S. Pat. Nos. 6,627,400 and 5,622,929 and in published U.S. Patent Application Nos. 2002/0013126 and 2003/0170915; each of which is hereby incorporated herein by reference in its entirety.

Molecular tag, E, in the present invention may comprise an electrophoric tag as described in the following references when separation of pluralities of molecular tags are carried out by gas chromatography or mass spectrometry: See, e.g., Zhang et al., 2002, *Bioconjugate Chem.* 13:1002-1012; Giese, 1983, *Anal. Chem.* 2:165-168; and U.S. Pat. Nos. 4,650,750; 5,360,819; 5,516,931; and 5,602,273, each of which is hereby incorporated by reference in its entirety.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. E may comprise a detection group for generating an electrochemical, fluorescent or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under a set of standard separation conditions conventional in the art, e.g., voltage, column pressure, column type, mobile phase or electrophoretic separation medium. In another aspect, the optical property is a fluorescence property, such as emission spectrum, fluorescence lifetime or fluorescence intensity at a given wavelength or band of wavelengths. Preferably, the fluorescence property is fluorescence intensity. For example, each molecular tag of a plurality may have the same fluorescent emission properties, but each will differ from one another by virtue of a unique retention time. On the other hand, one or two or more of the molecular tags of a plurality may have identical migration or retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. During or after electrophoretic separation, the molecular tags are detected or identified by recording fluorescence signals and migration times (or migration distances) of the separated compounds or by constructing a chart of relative fluorescent and order of migration of the molecular tags (e.g., as an electropherogram). Preferably, the presence, absence and/or amounts of molecular tags are measured by using one or more standards as disclosed by published U.S. Patent Application No. 2003/0170734A1, which is hereby incorporated by reference in its entirety.

Pluralities of molecular tags may also be designed for separation by chromatography based on one or more physical characteristics that include molecular weight, shape, solubility, pKa, hydrophobicity, charge, polarity or the like, e.g. as disclosed in published U.S. Patent Application No. 2003/0235832, which hereby is incorporated by reference in its entirety. A chromatographic separation technique is selected based on parameters such as column type, solid phase, mobile phase and the like, followed by selection of a plurality of molecular tags that may be separated to form distinct peaks or bands in a single operation. Several factors determine which HPLC technique is selected for use in the invention, including the number of molecular tags to be detected (i.e., the size of the plurality), the estimated quantities of each molecular tag that will be generated in the assays, the availability and ease of synthesizing molecular tags that are candidates for a set to be used in multiplexed assays, the detection modality employed and the availability, robustness, cost and ease of operation of HPLC instrumentation, columns and solvents. Generally, columns and techniques are favored that are suitable for analyzing limited amounts of sample and that provide the highest resolution separations. Guidance for making such selections can be found in the literature, such as, for example, Snyder et al., 1988, *Practical HPLC Method Development*, John Wiley & Sons, New York; Millner, 1999, *High Resolution Chromatography: A Practical Approach*, Oxford University Press, New York; Chi-San Wu, 1999, *Column Handbook for Size Exclusion Chromatography*, Academic Press, San Diego; and Oliver, 1989, *HPLC of Macromolecules: A Practical Approach*, Oxford University Press, Oxford, England.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye or an electrochemical label. Preferably, D is a fluorescent dye. Exemplary fluorescent dyes for use with the invention include water-soluble rhodamine dyes, fluoresceins, 4,7-dichlorofluoresceins, benzoxanthene dyes and energy transfer dyes, as disclosed in the following references: Anonymous, 2002, *Handbook of Molecular Probes and Research Reagents*, 8$^{th}$ ed., Molecular Probes, Eugene, Oreg.; U.S. Pat. Nos. 6,191,278, 6,372,907, 6,096,723, 5,945,526, 4,997,928, and 4,318,846; and Lee et al., 1997, *Nucleic Acids Research* 25:2816-2822. Preferably, D is a fluorescein or a fluorescein derivative.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag and the like.

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide and the like. Illustrative quenchers for active species that cause oxidation include polyenes, carotenoids, vitamin E, vitamin C, amino acid-pyrrole N-conjugates of tyrosine, histidine and glutathione. See, e.g. Beutner et al., 2000, *Meth. Enzymol.* 319:226-241.

One consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one aspect, cleavable linkages preferably are within about 1000 nm and preferably within about 20-200 nm, of a bound cleavage-inducing moiety. More preferably, for photosensitizer cleavage-inducing moieties generating singlet oxygen, cleavable linkages are within about 20-100 nm of a photosensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art will recognize that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed by Di Mascio et al., 1994, *FEBS Lett.* 355:287; and Kanofsky, 1983, *J. Biol. Chem.* 258:5991-5993; Pierlot et al., 2000, *Meth. Enzymol.* 319:3-20.

Photosensitizers may be attached directly or indirectly, via covalent or non-covalent linkages, to the binding agent of a class-specific reagent. Guidance for constructing such compositions, particularly for antibodies as binding agents are available in the literature, e.g. in the fields of photodynamic therapy, immunodiagnostics, and the like. Exemplary guidance may be found in Ullman et al., 1994, *Proc. Natl. Acad. Sci. USA* 91, 5426-5430; Strong et al., 1994, *Ann. New York Acad. Sci.* 745: 297-320; Yarmush et al., 1993, *Crit. Rev. Therapeutic Drug Carrier Syst.* 10: 197-252; and U.S. Pat. Nos. 5,709,994, 5,340,716, 6,251,581, and 5,516,636.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation depends on the nature of the photosensitizer, the nature of the cleavable linkage, the power of the source of irradiation and its distance from the sample. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include lasers such as, e.g., helium-neon lasers, argon lasers, YAG lasers, He/Cd lasers and ruby lasers; photodiodes; mercury, sodium and xenon vapor lamps; incandescent lamps such as, e.g., tungsten and tungsten/halogen and flashlamps. An exemplary photoactivation device suitable for use in the methods of the invention is disclosed International Patent Publication No. WO 03/051669. In such embodiments, the photoactivation device is an array of light emitting diodes (LEDs) mounted in housing that permits the simultaneous illumination of all the wells in a 96-well plate.

Examples of photosensitizers that may be utilized in the present invention are those that have the above properties and those disclosed by U.S. Pat. Nos. 5,536,834, 5,763,602, 5,565,552, 5,709,994, 5,340,716, 5,516,636, 6,251,581, and 6,001,673; published European Patent Application No. 0484027; Martin et al., 1990, *Methods Enzymol.* 186:635-645; and Yarmush et al., 1993, *Crit. Rev. Therapeutic Drug Carrier Syst.* 10:197-252. As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically according to routine methods.

In one embodiment, a photosensitizer is incorporated into a latex particle to form photosensitizer beads, e.g. as disclosed by U.S. Pat. Nos. 5,709,994 and 6,346,384; and International Patent Publication No. WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in *J. Amer. Chem. Soc.*, 97:3741 (1975). This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different than the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis.

As an example, a cleaving probe may comprise a primary haptenated antibody and a secondary anti-hapten binding protein derivatized with multiple photosensitizer molecules. A preferred primary haptenated antibody is a biotinylated antibody and preferred secondary anti-hapten binding proteins may be either an anti-biotin antibody or streptavidin. Other combinations of such primary and secondary reagents are well known in the art. Exemplary combinations of such reagents are taught by Haugland, 2002, *Handbook of Fluorescent Probes and Research Reagents, Ninth Edition*, Molecular Probes, Eugene, Oreg. An exemplary combination of such reagents is described below. There binding compounds having releasable tags ("$mT_1$" and "$mT_2$"), and primary antibody derivatized with biotin are specifically bound to different epitopes of receptor dimer in membrane. Biotin-specific binding protein, e.g. streptavidin, is attached to biotin bringing multiple photosensitizers into effective proximity of binding compounds. Biotin-specific binding protein may also be an anti-biotin antibody and photosensitizers may be attached via free amine group on the protein by conventional coupling chemistries, e.g., Hermanson (supra). An exemplary photosensitizer for such use is an NHS ester of methylene blue prepared as disclosed in published European Patent Application 0510688.

The following general discussion of methods and specific conditions and materials are by way of illustration and not limitation. One of skill in the art will understand how the methods described herein can be adapted to other applications, particularly with using different samples, cell types and target complexes.

In conducting the methods of the invention, a combination of the assay components is made, including the sample being tested, the binding compounds and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages.

The amounts of each reagent can generally be determined empirically. The amount of sample used in an assay will be determined by the predicted number of target complexes present and the means of separation and detection used to monitor the signal of the assay. In general, the amounts of the binding compounds and the cleaving probe can be provided in molar excess relative to the expected amount of the target molecules in the sample, generally at a molar excess of at least about 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with or after addition of the probes, depending on the effect being monitored.

The assay mixture can be combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually about 25° to 37° C.

After assembly of the assay mixture and incubation to allow the probes to bind to cell surface molecules, the mixture can be treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage can comprise irradiation of the mixture at the wavelength of light appropriate to the particular sensitizer used.

Following cleavage, the sample can then be analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g., prior to cleavage of molecular tags, and replaced with another buffer suitable for electrophoretic separation through filtration, aspiration, dilution or other means.

In certain embodiments, the subject may be administered a combination therapy that includes trastuzumab. The combination therapy can include trastuzumab in combination with one or more of any chemotherapeutic agent known to one of skill in the art without limitation. Preferably, the chemotherapeutic agent has a different mechanism of action from trastuzumab. For example, the chemotherapeutic agent can be an anti-metabolite (e.g., 5-fluorouricil (5-FU), methotrexate (MTX), fludarabine, etc.), an anti-microtubule agent (e.g., vincristine; vinblastine; taxanes such as paclitaxel and docetaxel; etc.), an alkylating agent (e.g., cyclophosphamide, melphalan, bischloroethylnitrosurea, etc.), platinum agents (e.g., cisplatin, carboplatin, oxaliplatin, JM-216, CI-973, etc.), anthracyclines (e.g., doxorubicin, daunorubicin, etc.), antibiotic agents (e.g., mitomycin-C, actinomycin D, etc.), topoisomerase inhibitors (e.g., etoposide, camptothecins, etc.) or other any other chemotherapeutic agents known to one skilled in the art.

Particular examples of chemotherapeutic agents that can be used in the various embodiments of the invention, including pharmaceutical compositions, dosage forms, and kits of the invention, include, without limitation, cytarabine, melphalan, topotecan, fludarabine, etoposide, idarubicin, daunorubicin, mitoxantrone, cisplatin paclitaxel, and cyclophosphamide.

Other chemotherapeutic agents that may be used include abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In another aspect, the invention is drawn to a method for determining whether a subject with a Her-2 positive cancer is unlikely to respond to treatment with at least one chemotherapeutic agent in addition to a Her2-acting agent and/or the patient is likely to have a short time course. In certain embodiments, the method comprises measuring in a biological sample from the subject's cancer an amount of Her-2 and/or Her-2 homodimers, wherein if the level of Her-2 and/or Her-2 homodimers is high, then the patient is unlikely to respond to at least one chemotherapeutic agent in addition to a Her-2 acting agent. In certain embodiments, the biological sample comprises FFPEs. In certain embodiments, the subject's cancer is breast cancer. In certain embodiments, the breast cancer is metastatic. In certain embodiments, the Her-2 acting agent is trastuzumab. In certain embodiments, the chemotherapeutic agent is paclitaxel. In certain embodiments, an amount of Her-2 is measured. In certain embodiments, an amount of Her-2 homodimers is measured. In certain embodiments, the amount of Her-2 homodimers is measured using an assay capable of measuring and/or quantifying an amount of protein-protein interactions in a sample. In a certain embodiment, the assay is the eTag™ assay. In certain embodiments, likeliness to respond is measured with respect to overall survival rate, time to progression and/or using the RECIST criteria or other response criteria.

In another aspect, the invention is drawn to a method for determining whether a subject with a Her-2 positive cancer is likely to respond to treatment with at least one chemotherapeutic agent in addition to a Her2-acting agent. In certain embodiments, the method comprises measuring in a biological sample from the subject's cancer an amount of Her-2 and/or Her-2 homodimers, wherein if the level of Her-2 and/or Her-2 homodimers is low, then the patient is likely to respond to at least one chemotherapeutic agent in addition to the Her-2 acting agent. In certain embodiments, the biological sample comprises FFPEs. In certain embodiments, the subject's cancer is breast cancer. In certain embodiments, the breast cancer is metastatic. In certain embodiments, the Her-2 acting agent is trastuzumab. In certain embodiments, the chemotherapeutic agent is paclitaxel. In certain embodiments, likeliness to respond or time course is measured with respect to overall survival rate, time to progression and/or using the RECIST criteria.

In another aspect, the invention is drawn to a method for determining whether a subject with a Her-2 positive cancer is likely to respond to a Her-2 acting agent and/or predicting whether the time course of the disease is long and/or predicting whether the subject will have a significant event, the method comprising detecting in a biological sample from the subject's cancer the amount of Her-2 and Her-2 homodimers and determining the ratio of Her-2 homodimers to total Her-2, wherein the subject's ratio is determined to be in one of at least 3 subgroups and if the subject's ratio is in the low or high subgroup, then the subject is likely to respond to the Her-2 acting agent, the subject is likely to have a long time course and/or the subject is not likely to have a significant event. In a preferred embodiment, the at least three subgroups are determined by comparing the Her-2 homodimer to total Her-2 ratio to the hazards ratio for populations treated with versus without a Her-2 acting agent, wherein if the hazard ratio is less than 1, then the subject is more likely to respond to the Her-2 acting agent, the patient is more likely to have a long time course and/or the patient is less likely to have a significant event.

In the cohort described in FIG. 29, both total Her-2 (H2T) and Her-2 homodimer (H2D) are significant predictors of TTP and OS following treatment with trastuzumab and stronger predictors than either IHC or FISH (see FIGS. 31, 32 and 33) when using the cutoff as shown in FIG. 34. In this cohort, the ratio of Her-2 homodimer to total Her-2 (H2D/H2T) was not significantly associated with TTP or OS when considered as a continuous variable. However, when the prognostic value of H2T, H2D and H2D/H2t for disease-free survival (DFS, time to development of metastatic breast cancer) was examined for 96 of the 103 Her-2-positive patients in the cohort who had been treated in the adjuvant setting with chemotherapy but not trastuzumab, the strongest association with DFS was seen with H2D/H2T (see FIG. 35). While the applicants do not wish to be confined to any particular mechanistic theory, one possible interpretation is that Her-2 activation rather than Her-2 expression might be the critical variable to measure in assessing risk to Her-2-positive patients and that H2D/H2T is a good measure of activation.

The H2D/H2T ratio, Her-2 expression (H2T) and Her-2 homodimer levels (H2D) were also examined with respect to trastuzumab responsiveness in the FIN HER clinical trial, which was designed to test the effectiveness of trastuzumab in the adjuvant setting. H2T, H2D and H2D/H2T were compared with IHC, CISH and clinical outcomes in the study (see FIG. 38). Since Her-2 positivity by IHC or FISH has been shown to correlate with adverse prognosis and improved clinical outcomes with trastuzumab, an ability to discriminate between likely responders and nonresponders with a quantitative assay, such as the HERMark assay, was anticipated. However, as shown by multivariate Cox proportional hazards analysis (FIG. 39), neither H2T nor H2D correlated significantly with outcome. H2D/H2T, on the other hand, was independently associated with time to any recurrence (TAR) and nearly significantly associated with time to distant recurrence (TDR). Because of these findings, STEPP (subpopulation treatment effect pattern plot) analysis was performed to examine hazard ratios for treated versus control patients across the distributions of H2T, H2D and H2D/H2T (FIGS. 40, 41 and 42, respectively). Subpopulations of 80 patients were used for these analyses. While neither H2D nor H2T identified any group of patients who did not benefit from trastuzumab, H2D/H2T was shown to discriminate between groups of patients that respond to trastuzumab and groups of patients that do not respond to trastuzumab. This latter group has intermediate H2D/H2T ratios that fall in-between a low H2D/H2T ratio group and a high H2D/H2T ratio group. While the applicants do not wish to be confined to a mechanistic theory, one possible explanation for this observation is that H2D/H2T is a measure of Her-2 activation in breast tumors and is therefore a prognostic biomarker for Her-2-positive patients in the adjuvant setting who do not receive trastuzumab and a predictive biomarker for the degree of clinical benefit that patients experience when treated with trastuzumab in the adjuvant setting.

In certain embodiments, the subject's cancer is breast cancer. In certain embodiments, the subject's cancer is metastatic or primary adjuvant. In certain embodiments, the Her-2 acting agent is trastuzumab. In certain embodiments, Her-2 and Her-2 homodimers are detected using the VeraTag™ assay. In certain embodiments, the likeliness to respond, likeliness to have a long time course and/or likeliness to have a significant event is measured as an overall survival rate, as time to progression, as time to distant recurrence and disease-free survival and/or response or clinical benefit using the RECIST criteria. In certain embodiments, whether the cancer is Her-2 positive is determined by IHC or FISH or CISH. In other embodiments, the invention is drawn to a method comprising determining whether the Her-2 homodimer to total Her-2 ratio is low, intermediate or high by comparing the Her-2 homodimer to total Her-2 ratio of the subject's cancer to optimal cutoffs. In yet further embodiments, if the ratio of Her-2 homodimers to total Her-2 is intermediate and/or the hazard ratio is equal to or greater than 1, then the patient is less likely to respond to a Her-2 acting agent and/or the patient is less likely to have a long time course and/or the patient is more likely to have a significant event.

In a further aspect, the invention provides methods of treating a subject with cancer. In one aspect, the methods comprise determining that the subject is afflicted with a cancer that is likely to respond to treatment with a Her2-acting agent and/or has a long time course according to a method of the invention and administering an effective amount of a Her2-acting agent to the subject as a result of said determination. In another aspect, the methods comprise determining that a subject is afflicted with a cancer that is likely to respond to treatment with a Her2-acting agent and/or has a long time course according to a method of the invention, then advising a medical professional of the treatment option of administering to the subject an effective amount of a Her2-acting agent. In another aspect, the methods comprise determining that a subject is afflicted with a cancer that has a short time course and/or that is unlikely to respond to a chemotherapeutic agent in addition to a Her-2 acting agent. In certain embodiments, the Her2-acting agent is trastuzumab. In certain embodiments, the chemotherapeutic agent is paclitaxel. In certain embodiments, the cancer is breast cancer. In certain embodiments, the breast cancer is metastatic.

EXAMPLES

Example 1: Antibodies, eTag™-Antibody, Biotin and Molecular Scissors

Monoclonal antibodies, Ab8 against cytoplasmic domain of HER2 and Ab15 against C-terminus of HER2, were purchased from Lab Vision. eTag™ reporters (Pro11 and Pro14) and streptavidin-conjugated methylene blue ("molecular scissors") were synthesized and purified according to protocol described previously (See, for example, above and U.S. Pat. No. 7,105,308, which is incorporated by reference herein, including any drawings). Antibody eTag™ and antibody-biotin conjugates, i.e., Ab8-Pro11 and Ab15-biotin, were made using sulfo-NHS-LC-LC-biotin (Pierce) as linker according to manufacturer's protocol and conjugation products purified by HPLC (Agilent).

Example 2: Cell Culture, Fixation, Processing and Paraffin Embedding

Four breast cancer cell lines, MDA-MB-468, MCF-7, MDA-MB-453 and SKBR-3, were purchased from American Type Cell Culture Collection. All cell-lines were maintained at 37° C. and 5% $CO_2$ in Dulbecco's modified Eagle medium (DMEM): F12 (50:50), 10% FBS, 1% PSQ (10% fetal bovine serum, 1% penicillin-streptomycin) and 2 mM L-glutamine. Cells were grown to near confluence on at least ten 150-mm culture plates for each cell line. After removal of medium, the cells were washed once with cold 1×PBS and 15 mL of 10% NBF (neutral buffered formalin) was added to each plate. Cells were fixed over night (>16 hrs) at 4° C. After removal of the fixative solution, the cells were harvested by scraping with residual fixative solution and centrifuged at 3200×g for 15 min. The cell pellet was transferred to a rubber O-ring, wrapped with filter paper and placed in a processing cassette. Automatic Tissue-Tek processor was used for processing. Briefly, cell pellet was exposed to increasing concentrations of alcohol, Clear-rite (xylene substitute) and paraffin. After processing, pellet was embedded in a block using a paraffin embedding station. All solvents used for cell pellet processing were obtained from Richard-Allen Scientific.

Example 3: Breast Tissues, Fixation, Processing and Paraffin Embedding

Frozen breast tissues with different Her-2 expression levels were purchased from Biooptions. The tissue chunks (0.9-1.9 grams) were fixed in 10% NBF for 24 hrs at 4° C., and processed and paraffin-embedded as described for cell line pellets.

Example 4: Microtomy

Sections of 7 um in thickness were sliced with a microtome (LEICA) and placed on positively charged glass slides (VWR) with serial number labeled. Slides were air-dried for 30 min and then baked in a heated oven set at 60° C. for 1 hr. All sample slides were stored at 4° C. for future assay.

Example 5: Immunohistochemistry and H&E Staining

Immunohistochemistry for Her-2 was performed on Ventana Discovery XT system according to manufacturer's instructions. Primary antibody against Her-2 (CB 11) and other reagents were purchased from Ventana. H&E staining of FFPE breast tissues was conducted according to standard protocol.

Example 6: Her-2 eTag™ Assay in Formalin Fixed, Paraffin Embedded Cell Lines and Breast Tissue FFPE samples were deparaffinized/rehydrated using a series of solvents. Briefly, slides were sequentially soaked in xylene (2×, 5 min), 100% ethanol (2×, 5 min), 70% ethanol (2×, 5 min) and deionized water (2×, 5 min). Heat-induced epitope retrieval of the rehydrated samples was performed in a dish containing 250 mL of 1× citrate buffer (pH 6.0) (Lab Vision) using microwave oven (Spacemaker II, GE): 3 min at power 10 followed by 10 min at power 3. After being cooled down for 20 min at room temperature, the slides were rinsed once with deionized water. A hydrophobic circle was drawn on slide using a hydrophobic pen (Zymed) to retain reagents on slides. The samples were then blocked for 1 hr with blocking buffer that contains 1% mouse serum, 1.5% BSA and a cocktail of protease and phosphatase inhibitors (Roche) in 1×PBS. After removal of the blocking buffer with aspiration, a mixture of eTag™- and biotin-conjugated antibodies (both at concentration of 4 ug/mL) prepared in blocking buffer was added and binding reactions were incubated overnight in a humidified chamber at 4° C. with shaking. The antibody mix was aspirated and samples were washed with wash buffer containing 0.25% TritonX-100 in 1×PBS and streptavidin-conjugated methylene blue at concentration of 2.5 ug/mL in 1×PBS was added. The concentrations of the antibody and streptavidin-photosensitizer conjugates were all optimized based on signal specificity and assay readout dynamic range using both cell line and breast tissue samples. After 1 hr incubation at room temperature, the streptavidin-methylene blue reagent was aspirated and the samples were washed in wash buffer once followed by 3 changes of deionized water. Illumination buffer containing 3 pM fluorescein and two CE internal markers (MF and ML) in 0.01×PBS was added on sample sections. The bound eTag™ was released at 4° C. by photo-activated cleavage using an in-house LED array illuminator equipped with an electronic ice cube (Torrey Pine Scientific). The CE sample containing the released eTag™ reporters was collected from above the tissue section on the slides and the released eTag™ reporters in the CE samples were separated and detected on ABI3100 CE instrument (22-cm capillary array) (Applied Biosystems) under CE injection condition of 6 kV and 50 sec at 30° C.

Example 7: Data Analysis

The identification and quantification of eTag™ was carried out using eTag™ Informer software (see, for example, United States publication number 0203408-A1, which is incorporated by reference herein, including any drawings). To analyze the eTag™ signals in a raw CE electropherogram, two CE internal markers, MF (first marker) and ML (last marker), were used to identify the eTag™ peaks according to their electrophoretic mobility or migration time, t, relative to the two markers, i.e., [t(eTag™)-t(MF)]/[t(ML)-t(MF)]. The identified eTag™ peaks were then quantified by peak area calculation for each eTag™. To correct for variability in eTag™ recovery from the tissue section, and the run variability in CE injection efficiency and/or detection sensitivity across capillary array, fluorescein (3 pM) was included in the illumination and eTag™ recovery buffer, and co-electrophoresed as an internal reference control in each sample run. The area of each eTag™ peak is then reported as RFU or RPA by area normalization of the eTag™ peak (eTag™ peak area) to the internal fluorescein peak (fluorescein peak area/1 pM) and having units of concentration (pM). The final quantification terms for the target protein detected by the eTag™ assay can be either RPA (pM) for similar samples or the RPA*IB vol/TA for variable tumor samples (=Relative peak area multiplied by the illumination buffer volume (IB) loaded onto sample section; divided by the tumor area in $mm^2$ (RPA*IB vol/TA=pmole/L*L/$mm^2$=pmole/$mm^2$).

Example 8: Titration of Sample Section Size and Estimation of Tumor Area

To evaluate the ability of the eTag™ assay to quantify the target proteins in the same sample specimen, section size of the cell line samples cut at 7 m on slides was titrated serially using a razor blade and different numbers of microtome-cut sections of breast tissues were captured on one slide for each titration of the tissue material. After the eTag™ assay, the cell line slides were air-dried and photo-scanned. Section area of the samples in $mm^2$ was measured and calculated on the scanned images using ImageJ software. For breast tissue sample, post-eTag™ assay slides were H&E stained and mounted with a mounting medium (Richard-Allan Scientific). The tumor content of the tissue samples was defined by a certified pathologist using a pen marker and area of the tumor content in $mm^2$ was measured and calculated with the ImageJ software in the same manner as for the cell line samples.

Example 9: Development of eTag™ Assay for FFPE Cells

Figure 1:
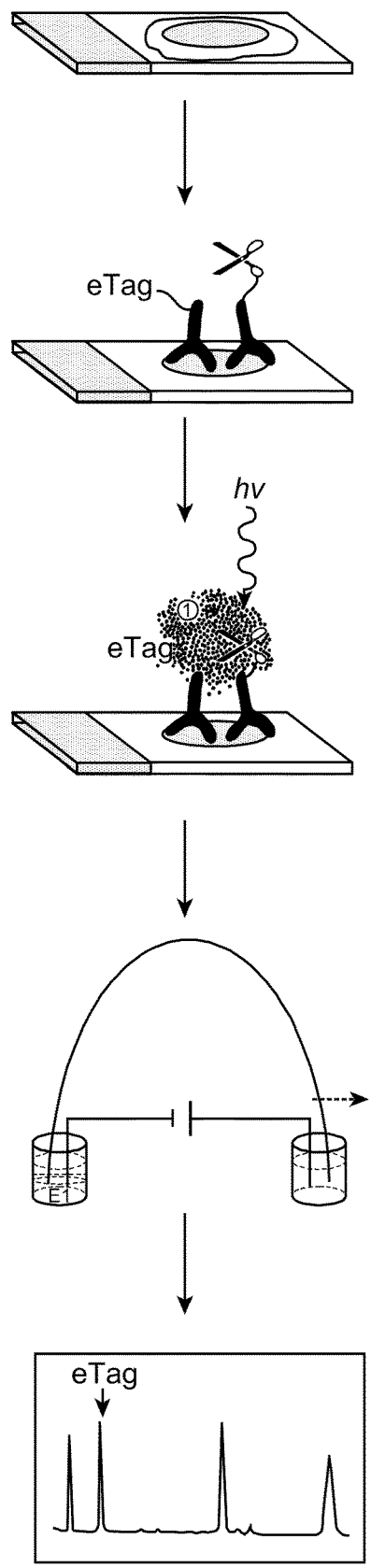
FIG. 1 shows an outline of an FFPE eTag™ assay.

An outline of the FFPE eTag™ assay is shown in FIG. 1. Before the start of the assay, FFPE microtome sections were generated from human breast cancer cell lines or tumor tissues and baked onto glass slides as described above. The FFPE cell line or tumor tissue sections were deparaffinized and rehydrated by standard xylene/ethanol/water protocols, then subjected to heat-induced antigen retrieval followed by the eTag™ assay. The eTag™ assay was initiated by the addition of the eTag®-conjugated and biotin-conjugated antibody pair followed by washing and incubation with a streptavidin-conjugated photo-sensitizer (i.e., SA-methylene blue, or SA-MB). The cell line and tumor sections were exposed to light illumination at 670 nm during which the photo-sensitizer bound to the biotin antibody converted dissolved oxygen to a more reactive, singlet state oxygen ($O_2$) in buffer solution. This occurs via absorption, intersystem crossing and $O_2$ production.

Figure 2A:
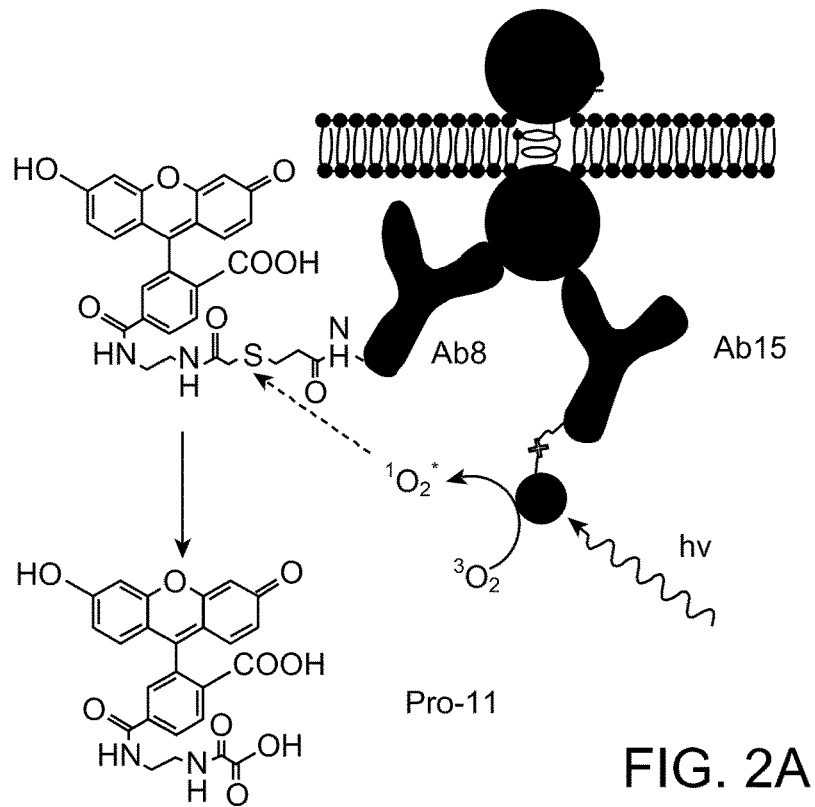
FIG. 2A and FIG. 2B show an eTag™ reaction where diffusing reactive singlet oxygen cleaves the covalent linker between an eTag™ reporter molecule and an antibody.
Figure 2B:
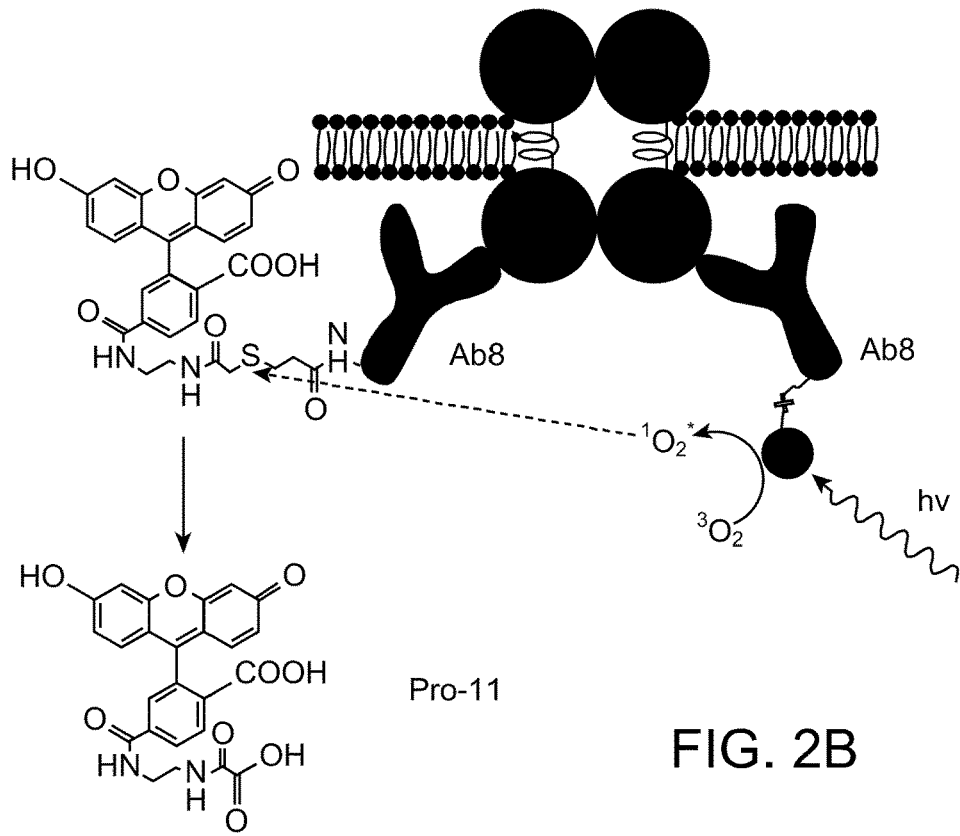

The $O_2$ molecules are short-lived ~4 ps in water) and thus have a limited average diffusion distance, e.g., 50% of the $O_2$ produced will diffuse ~80 nm and <0.1% will diffuse 250 nm before being quenched (Latch, Science, 2006). Consequently, the diffusing $O_2$ reacts with the covalent linker between the eTag™ reporter molecule and the antibody, leading to proximity-based cleavage of the thio-ether bonds and release of eTag™ reporter molecules bound on the tissue cells (See e.g., FIGS. 2A and 2B). Applied to conventional capillary electrophoresis (CE) instruments, the released eTag™ reporter is separated according to its migration properties and detected as a fluorescence peak in an electropherogram, which can be identified and quantified as the peak area using eTag™ Informer software. The eTag™ fluorescent reporter molecule peak area is, therefore, directly proportional to the amount of the target antigen present in the cells. The eTag™ peak area is initially calculated in RFU. To correct the eTag™ signal for variable recovery from tissue sections and injection into CE, the peak area (RPA) is calculated relative to that of a known concentration of the internal standard fluorescein.

Figure 3:
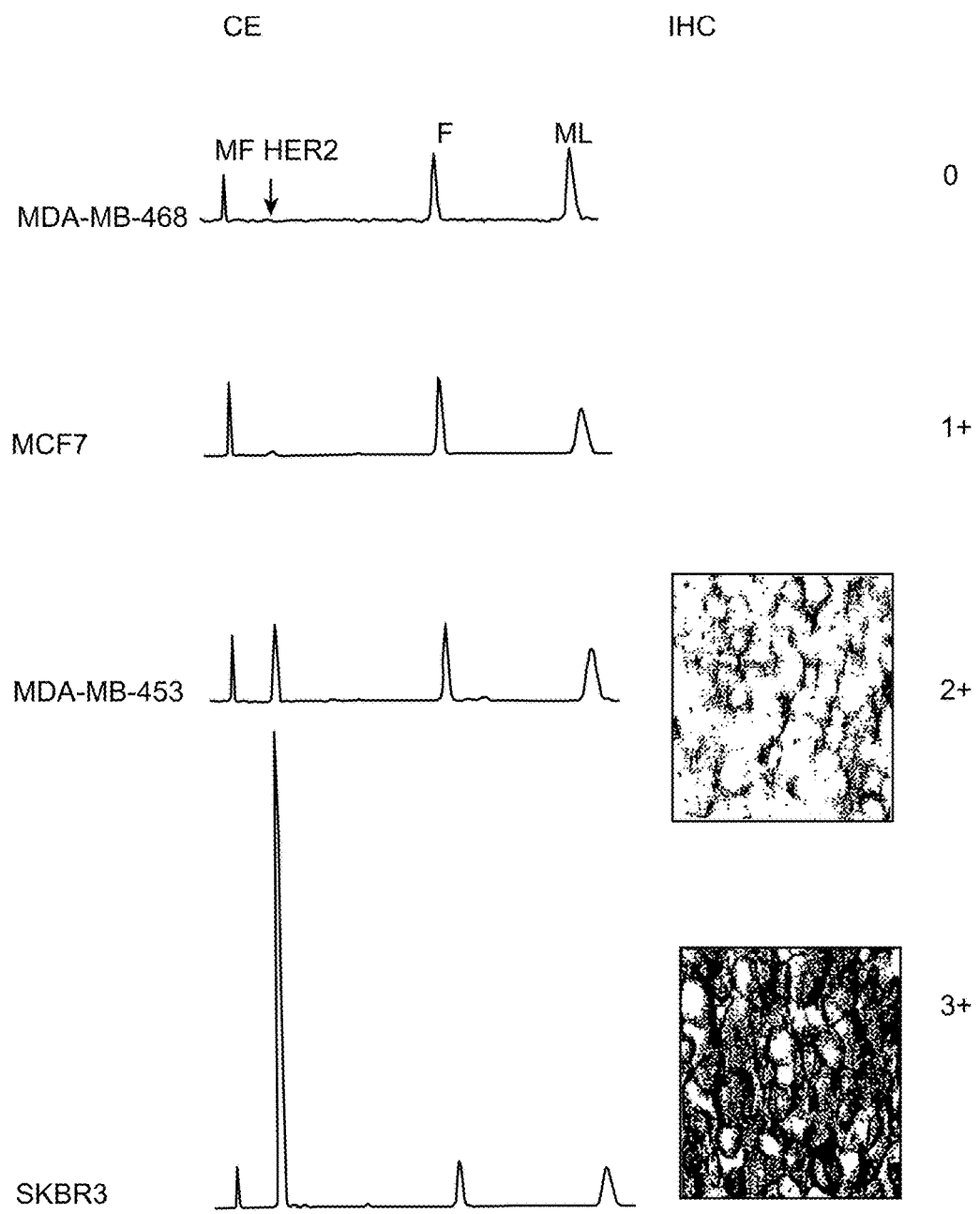
FIG. 3 shows representative electropherograms of the eTag™ signal generated for four well characterized breast cancer cell lines along with a parallel Her-2 IHC micrograph. The left side of the graph indicates the cell line, the middle shows the corresponding electropherogram and the right side shows the corresponding IHC.

To identify a proximity pair of Her-2 antibodies suitable for eTag™ assay development, five antibodies were conjugated with either eTag™ fluorescent reporter groups or biotin, and ten proximity pairs were tested at 1 ug/mL each on FFPE-prepared human breast tumor cell lines. The performance of each antibody pair was evaluated by their ability to parallel the relative Her-2 protein expression levels, determined by FACS analysis and other independent methods in SK-BR-3 ($6 \times 10^5$ per cell), MDA-MB-453 ($1.5 \times 10^5$ per cell); BT-20 ($6 \times 10^4$ per cell); MCF-7 ($2 \times 10^4$ per cell), and MDA-MB-468 cells (negative control; $<10^4$ per cell). The Her-2 antibody pair Ab15 and Ab8 generated the greatest dynamic range of signal, consistent with the relative Her-2 expression level quantified by other methods. Representative electropherograms of the eTag™ signal generated for four well characterized FFPE breast cancer cell lines are shown in FIG. 3, along with a parallel Her-2 IHC micrographs utilizing DAB color development. The peak area of the eTag™ generated from the Her-2 eTag™ assay parallels IHC signal intensity and is consistent with accepted IHC test categories of Her-2 expression level (i.e., HercepTest: SK-BR-3=3+; MDA-MB-453=2+; MCF-7=0-1+; MDA-MB-468=0).

Example 10: eTag™ Antibody and Assay Optimization

Having identified an antibody pair suitable for eTag™ assay development in the proximity format, relative affinity and specificity were determined for the individual antibodies under non-proximal, direct eTag™ release conditions, as well as a $K_{1/2}$ and saturating concentrations under proximal conditions. Antibody titrations were performed with eTag™-conjugated Ab8-Pro11 or Ab15-Pro11 on positive (SKBR-3) and negative (MDA-MB-468) Her-2-expressing FFPE cell lines utilizing a saturating concentration (200 uM) of the $O_2$ sensitizer methylene blue for eTag™ release. This non-proximal release of Pro11 eTag™ from increasing concentrations of bound antibody reflects the antibody's relative affinity. The multi-parameter curve fitting result for Ab8-Pro11 is most consistent with a single binding site of $K_D$=6-8 ug/mL (40-50 nM) and similar to the single site binding of Ab8-Pro11 with a $K_D$ of 2-3 ug/mL (12-18 nM). The non-specific binding of Ab8-Pro11 can be estimated from the negative control MDA-MB-468 as <4% percent of the total SK-BR-3 signal, whereas the non-specific binding of Ab15-Pro11 is estimated to be 10%.

Optimal Ab8-Pro11 and Ab15-biotin concentrations for the proximity assay of total Her-2 were determined by antibody titrations on FFPE breast cancer cell lines and human breast tumor samples. The concentrations of both antibodies were held equal during the titration from 0.25 ug/mL to 8 ug/mL. A $K_{112}$ of maximal eTag™ signal equal to approximately 2 ug/mL was observed for both antibodies, and a saturating concentration reached at 3-4 ug/mL. In this and other similar titration studies, the optimal signal-to-background ratio of 100-200 is 2-4 ug/mL for both Ab8-Pro11 and Ab15-biotin. Additional optimization experiments determined that the concentration of the $O_2$-sensitizing reagent SA-MB of 2.5 ug/mL is saturating under most conditions and the optimal illumination time is 2 hours. Given these results, a concentration of 4 ug/mL (26 nM) was chosen for both Ab8-Pro11 and Ab15-biotin, and 2.5 ug/mL for SA-MB, for further assay optimization and characterization of performance.

Three Her-2 eTag™ assay formats were compared at 4 ug/mL antibody concentration to identify conditions that result in the best assay performance. These are two proximity formats, consisting of Ab15-biotin plus Ab8-Pro11 and Ab8-biotin plus Ab15-Pro11, and the non-proximity direct release of eTag™ from Ab8-Pro11 in the presence of saturating methylene blue. Although the methylene blue direct release format provides highest overall signal, both proximity assay methods result in lower background, higher signal to background ratio and dynamic range, and tracked most closely with expected receptor number per cell determined by independent methods. The proximity format using Ab15-biotin and Ab8-Pro11 results in the best signal to background ratio and was selected as the final assay format for further study.

Example 11: Her-2 Assay Specificity

The specificity of the total Her-2 proximity assay was tested by several approaches. First, the Her-2 antibodies were determined to be Her-2-specific by immunoblotting against purified Her-1 and Her-2 tyrosine kinase domains and recombinantly expressed Her-3. Non-specific background signal in the Her-2 eTag™ proximity assay was also evaluated by competition studies with excess unlabelled Her-2 or Her-1 antibodies. A 20-fold excess of unlabelled Ab8 competes nearly all Ab8-Pro11 signal, with <2% background signal in FFPE SKBR-3 cell sections, <7% in MDA-MB-453 cell sections and <30% in MCF-7, whereas a 20-fold excess of the HER1 antibody Ab15 has no effect. Assay antibody specificity was further demonstrated by the replacement of the Her-2 Ab15-biotin antibody with Her-1 Ab15-biotin. Under these conditions only 2% of the total Her-2 signal is observed in SKBR-3 cells that express $1 \times 10^5$ Her-1 plus $6 \times 10^5$ Her-2 per cell or in MDA-MB-468 cells that express $>10^6$ Her-1 per cell and $<10^4$ Her-2. These results indicate the highly specific antibody recognition of Her-2 when presented in the eTag™ proximity format.

Since Her-2 antibodies Ab15 and Ab8 are both directed to the tyrosine kinase domain (Tandon et al, 1989; DiGiovonni and Stern, Labvision), they were tested for epitope exclusivity. The absence of cross-competition between Ab15-Pro11 and Ab8 and visa-versa in direct-release eTag™ assays indicates that they bind to distinct, non-overlapping epitopes on Her-2. Lastly, the contribution of each component of the dual antibody Her-2 eTag™ proximity assay to the background signal was evaluated by the selective omission of each reagent, or replacement of Ab8-Pro11 or Ab15-biotin with IgG1-Pro11 or IgG1-biotin isotype control antibodies. The most significant contribution to the assay background signal is the non-specific release of Pro11 eTag™ from Her-2 Ab8-Pro11 in the presence of IgG1-biotin isotype control. This background represents 4% of the total signal from high levels of Her-2 (SK-BR-3) to 15% with low levels of Her-2 (MCF-7). The release of eTag™ is also completely light dependent. Taken together, the results indicate that this proximity format of the Her-2 eTag™ assay, utilizing Ab8 and Ably antibodies, is highly specific over a broad dynamic range of receptor level and signal.

Example 12: Homodimer eTag™ Assay

Figure 4:
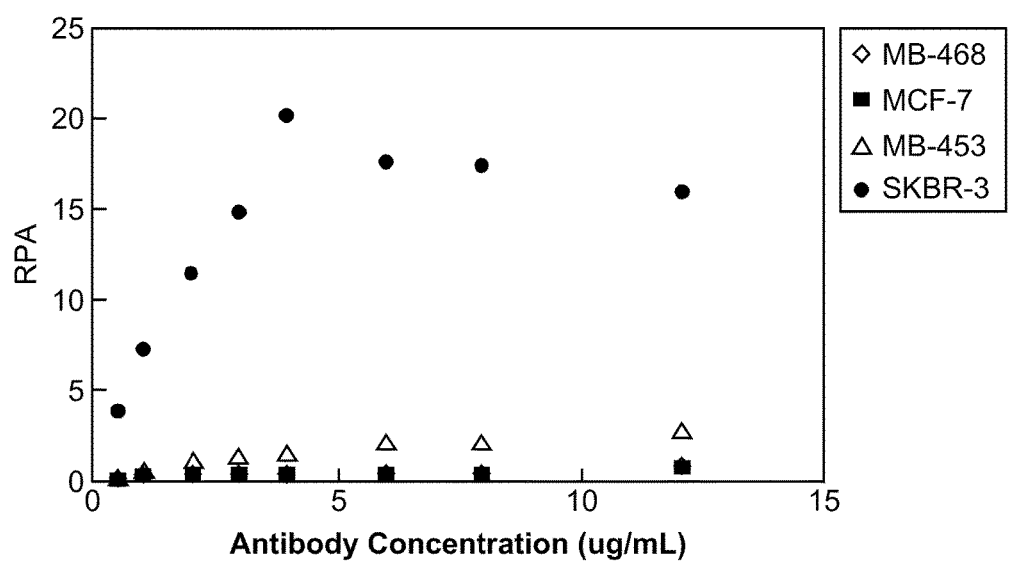
FIG. 4 shows the results of an antibody titration experiment with Ab8-biotin and Ab8-Pro11 added at equal concentrations resulting in an increasing eTag™ signal of approximately 4 ug/mL as set forth in Example 4. The x-axis shows RPA and the y-axis show shows antibody concentration. The inset at the right provides a key for the type of cell charted in each position in the graph.

Through chemical crosslinking and immunoblotting, and FRET, it has been demonstrated that Her-2 can exist as homodimers when overexpressed in highly amplified breast tumor cells such as SKBR-3 cells (Citri et al, 2003; Nagy et al 2002). The Her-2 eTag™ assay specificity produced by Ab8 and Ab5 in the proximity format was utilized to develop an eTag™-based assay compatible with the measure of Her-2 homodimers. The close proximity of HER2 subunits within a homodimer can facilitate generation of an overlapping $O_2$-generating sphere as a result of Her-2-bound Ab8-biotin-SA-MB within functional proximity of bound Ab8-Pro11. An antibody titration experiment with Ab8-biotin and Ab8-Pro11 added at equal concentrations results in an increasing eTag™ signal up to approximately 4 ug/mL (See FIG. 4). Similar results were observed with an independent titration of Ab15-Pro11 and Ab15-biotin. Given the single binding sites on Her-2 for either Ab8-Pro11 or Ab15-Pro11 observed in antibody titration experiments, these results are most consistent with the detection of Her-2 homodimers through proximity of an eTag™ antibody bound to one subunit and a biotin antibody bound to the other subunit of the dimer. This is supported by the observation that the Her-2 homodimer eTag™ assay activity tracks with the relative level of Her-2 homodimer observed by chemical crosslinking and immunoprecipitation/immunoblotting.

In Her-2 amplified breast cancer cells, Her-2 has been proposed to cluster within secondary domains such as receptor patches or rafts (Nagy et al) or localized in specialized membrane protrusions, primarily as Her-2 homodimers stabilized by Hsp90 (Citri et al, Neckers). Her-2 has also been shown to co-isolate with other signaling proteins suggesting that it exists as part of a functional signaling complex, including other Her receptors. Specificity and proximity of the Her-2 homodimer eTag™ assay were evaluated by exchanging Her-2 Ab8-biotin with biotinylated control antibodies to other co-localized proteins or isotype control antibodies. In the absence of Ab8-biotin antibody, or in the presence of 4 ug/mL IgG1-biotin isotype control or Ab8-biotin plus 40 ug/mL unlabelled Ab8 (10-fold excess), the non-specific signal is 4-8% of the Her-2 homodimer signal measured in SKBR-3 cells or human breast tumor tissue at either 2 or 4 ug/mL Ab8-biotin and Ab8-Pro11. The specificity of the Her-2 homodimer assay was then evaluated by replacement of Ab8-biotin with biotinylated antibodies directed to membrane-associated proteins having various degrees of proximity to Her-2. Biotinylated antibodies to the low abundant Her-2 signaling complex protein PTEN and the moderately abundant co-signaling receptor Her-1, both of which could exist at a steady state level within a Her-2 receptor signaling complex, resulted in a non-specific signal that is 15-20% of the Her-2 homodimer signal in SKBR-3 or human breast tumor tissue. A biotinylated antibody to the highly abundant structural and cytosolic and membrane associated protein cytokeratin also results in a background signal that is 15-20% of the Her-2 homodimer signal. Overall, the non-specific signal was generally 5-10% lower at 2 ug/mL antibody compared to 4 ug/mL. Taken together with the demonstration of the cognate antigen detection by these antibodies in SKBR-3 cells, the results are consistent with the specificity of the Her-2 homodimer assay. For these reasons, and to minimize potential non-specific signal, the Her-2 homodimer assay utilizing 2 ug/mL Ab8-biotin and Ab8-Pro11 was further evaluated.

Example 13: Normalization of Assays

Figure 5:
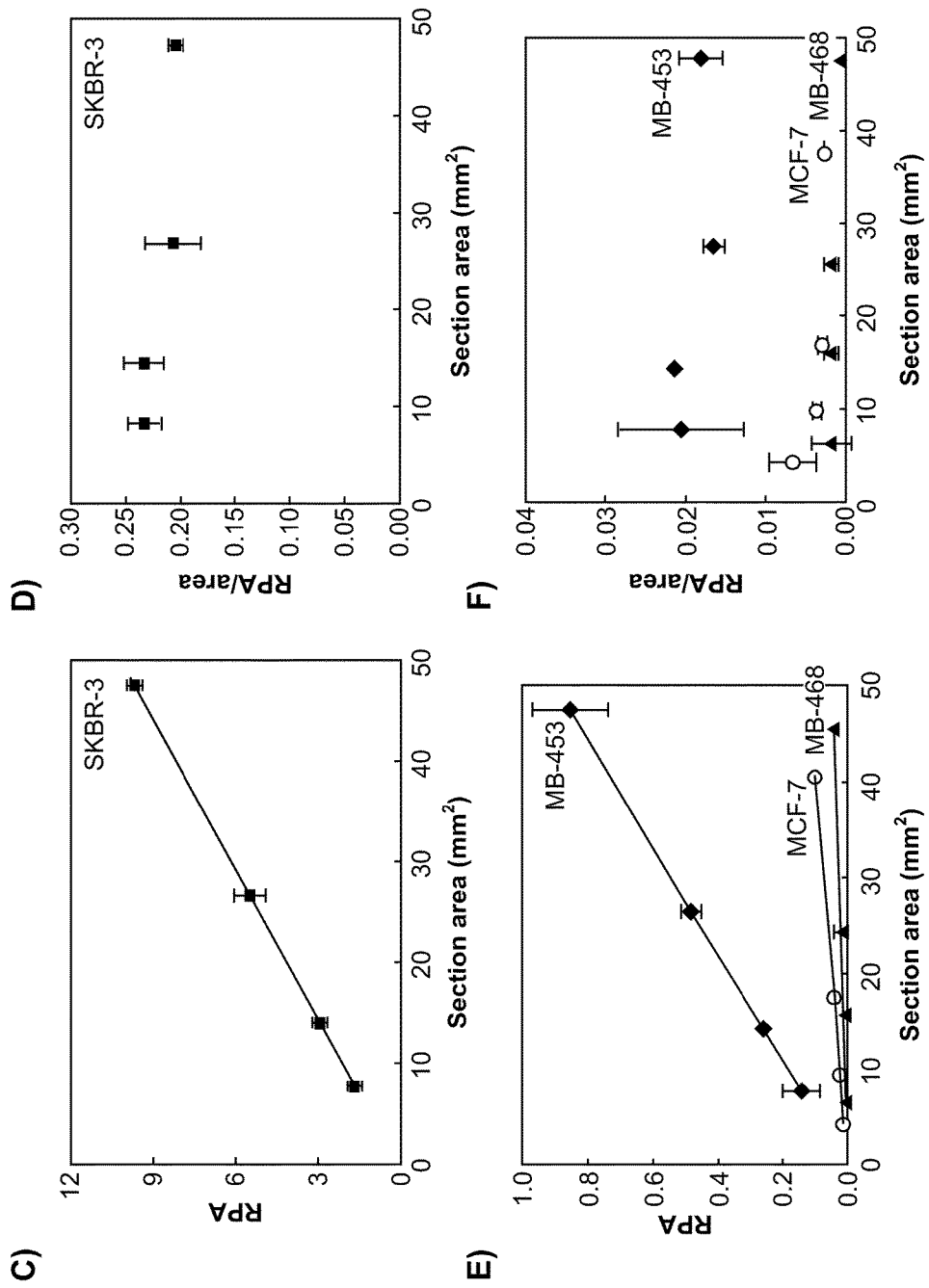
FIG. 5 shows the section size titration of Her-2 control breast cancer cell lines and normalization as set forth in Example 13. The left top graph displays results for the SKBR-3 cell line and the bottom left graph displays results for the MB-453, MCF-7 and MB-468 cell lines. The x-axis shows section area and the y-axis shows RPA. The graphs on the right display respective normalizations, the top graph displaying SKBR-3 cell lines and the bottom graph displaying MB-453, MCF-7 and MB-468 cell lines. The x-axis shows tumor section area and the y-axis shows RPA divided by tumor area.

The Her-2 level measured in a FFPE breast tumor sample can vary as a consequence of the tumor content, as well as differences in the receptor level per cell. Therefore, besides a reliable measure of the Her-2 level, it is necessary to normalize the Her 2 Tag eTag™ assay signal to a measure of the tumor content. The tumor content of a sample is determined by pathologist measurement of the tumor area that had been stained with hematoxylin-eosin. Since the amount of antigen will be proportional to the tumor area for a given level of Her-2 expression, the linearity of the Her-2 eTag™ assay signal as a function of antigen level was evaluated by the use of FFPE section-size or tumor area titrations. FFPE blocks and sections of decreasing area were generated for the four breast tumor Her-2+ cell lines SK-BR-3, MDA-MB-453, MCF-7, and MDA-MB-468, and from three different human breast tumors with Her-2 IHC staining levels of 3+, 1+, and 0. Her-2 eTag™ assay signal increases linearly as a function of sectional or tumor area for all cell line samples from 5-50 mm$^2$ and for the three breast tumor samples from 10-250 mm$^2$, whether collected in a constant or increasing volume of illumination buffer (See FIG. 5).

Example 14: Comparison of eTag™ to IHC and FISH

Having demonstrated that the Her-2 total and Her-2 homodimer eTag™ assays are specific, linear over a wide range of tumor area and sensitive over a broad dynamic range of receptor number per cell in breast tumors and cell lines, Her-2 levels in human breast cancer samples were measured by the eTag™ assay and compared with the characterized methods of IHC and FISH. Over 230 tumors were processed by FFPE and 7 um sections were evaluated for tumor content by H&E staining. Of these, 170 were found to have appreciable tumor area of 10 mm.sup.2 or greater. Sections of these samples were then assayed for Her-2 total and homodimer levels by the eTag™ assays, and compared with Her-2 IHC staining intensity quantified by standard test categories as well as using a Histological score. A selected subset of 20 tumors having a range of Her-2 levels was also analyzed for Her-2 gene amplification by FISH. All Her-2 eTag™ measurements were adjusted for eTag™ assay collection volume, and normalized to tumor area (RPA*vol/tumor area, as set forth below). Characteristic distributions of sample properties indicate that the majority of tissue section areas are 20-200 mm$^2$ (88%), the tumor area is 20-100 mm$^2$ (76%) and the tumor percentage is therefore 30-60%. The Her-2 total eTag™ signal in 174 breast cancers represents a continuum measurement over a dynamic range greater than 2 logs, in contrast with conventional IHC categories (0, 1+, 2+, 3+). The correlation between Her-2 total eTag™ signal and IHC categories was significant (correlation=0.84, p<0.0001), but the Her-2 total signal overlapped with the adjacent IHC categories. The IHC H-score correlates well within the lower range of Her-2 total eTag™ assay signal, but displayed a plateau at the higher range of Her-2 total. Her-2 gene amplification (Her-2/CEP17 ratio and gene copy #) by FISH loosely correlates with IHC categories and Her-2 total values, although for a given Her-2/CEP17 ratio or gene copy number the Her-2 eTag™ signal can elaborate over a 4-5-fold range. Correlation between Her-2 homodimer and Her-2 total levels measured by eTag™ assays was observed ($r^2$=0.7, P<0.001). These results demonstrate that eTag™ assays reliably measure Her-2 total and homodimer levels in FFPE human breast cancer samples, yet differs in several respects from the traditional Her-2 measures.

The accuracy of Her-2 eTag™ assays was demonstrated by the ability to detect Her-2 and Her-2 homodimerization in an evaluation of 174 human breast tumor samples. Her-2 IHC was conducted in parallel, and although there was general agreement between the eTag™ assay and Her-2 IHC in both IHC test categories and a Histoscore that considers the percentage of Her-2+ cells, differences with IHC were observed. The Her-2 protein level distribution detected by eTag™ assay overlapped between the IHC test categories. Also, while the Her-2 protein levels by eTag™ assay are consistent with the Histoscore at low Her-2 levels, at higher levels the Histoscore plateaus while the eTag™ assay values extend the dynamic range. Clinically meaningful information regarding the relative response to Her-2-targeted therapies may be contained in a continuous, quantitative Her-2 protein and homodimerization measurement in this highly expressed range (i.e., $10^5$-$10^6$ receptors per cell).

Example 15: Application of eTag™ Assay to a Clinical Cohort

The Jules Bordet clinical cohort (Brussels, Belgium) consisting of 71 patients with metastatic breast cancer was examined, the cohort was enrolled into the trastuzumab Expanded Access Program or the Identified Patient Program sponsored by F. Hoffman-LaRoche in Belgium prior to May of 2002. The patients were required to have metastatic breast cancer and to have had prior treatment with at least two chemotherapy regimens. Patients received trastuzumab as single agent or in combination with chemotherapy, primarily paclitaxel. Patients enrolled but never treated and patients receiving incomplete administrations of trastuzumab (1-5 weeks) were excluded from the analysis, unless discontinuation was unequivocally ascribed to progressive disease. Patients with previous or concomitant cancer other than breast were excluded, as were patients without archival samples of their invasive breast cancer. Central confirmation of Her-2 over-expression by FISH(N=64) or IHC(N=7) was mandatory.

Example 16: Comparison of eTag™ and IHC and FISH in a Clinical Cohort

The eTag™ assay was used to quantitate Her-2 expression and Her-2 homodimers in FFPE specimens from the clinical cohort of metastatic breast cancer patients who were treated with a trastuzumab-containing regimen following failure of chemotherapy. The eTag™ signal readout from capillary electrophoresis represents the total amount of eTag™ of an entire tissue section. Since section size and tumor percentage differ with various individual specimens, the eTag™ signal needed to be normalized by the total amount of tumor (tumor content) for each specimen in order to compare eTag™ measurements among different specimens. Tumor content was measured as the total surface area of the tumor. Since the thickness of a tissue section is typically constant, total tumor area represents a good surrogate for total tumor content in an eTag™ assay.

An H&E stained slide was first examined microscopically by a board-certified pathologist to confirm pathologic diagnosis. All areas of viable tumor cells were then marked out with a black marker pen by the pathologist. Care was taken to exclude non-tumor elements and necrotic tissue so that marked areas represented areas of viable tumor. The marked slide was then scanned by a standard flatbed scanner (HP ScanJet 4890) to create a digital image. The digital image was analyzed with ImageProJ software (ImageJ 1.36b) and total pixels of the marked areas were converted to surface area (mm2). eTag™ measurement was then expressed as amount of eTag™ signal per $mm^2$ of tumor area.

Figure 7B:
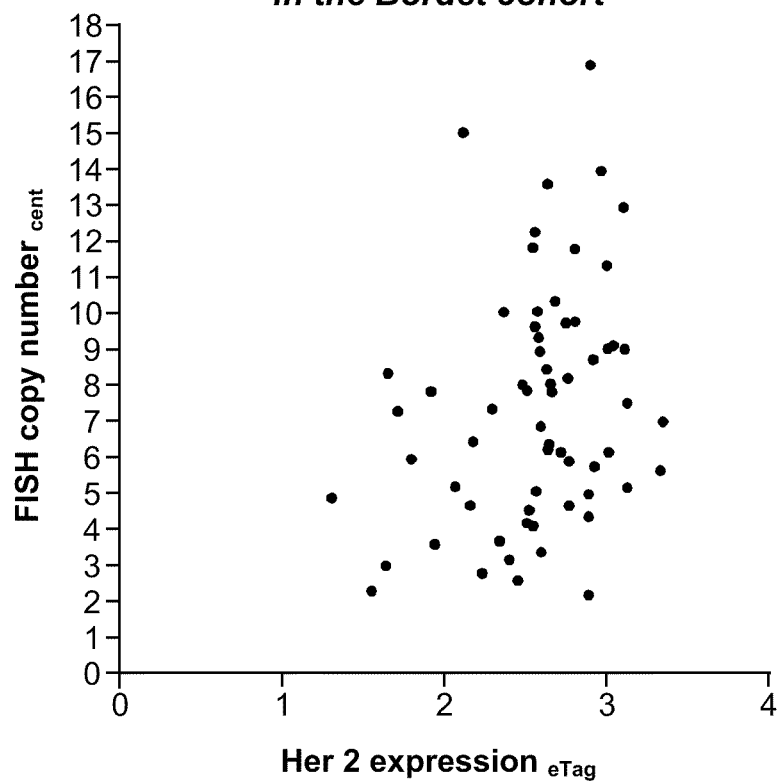
FIG. 7B shows the correlation of Her-2 expression by eTag™ (y-axis) with centromere-corrected FISH (x-axis).
Figure 8:
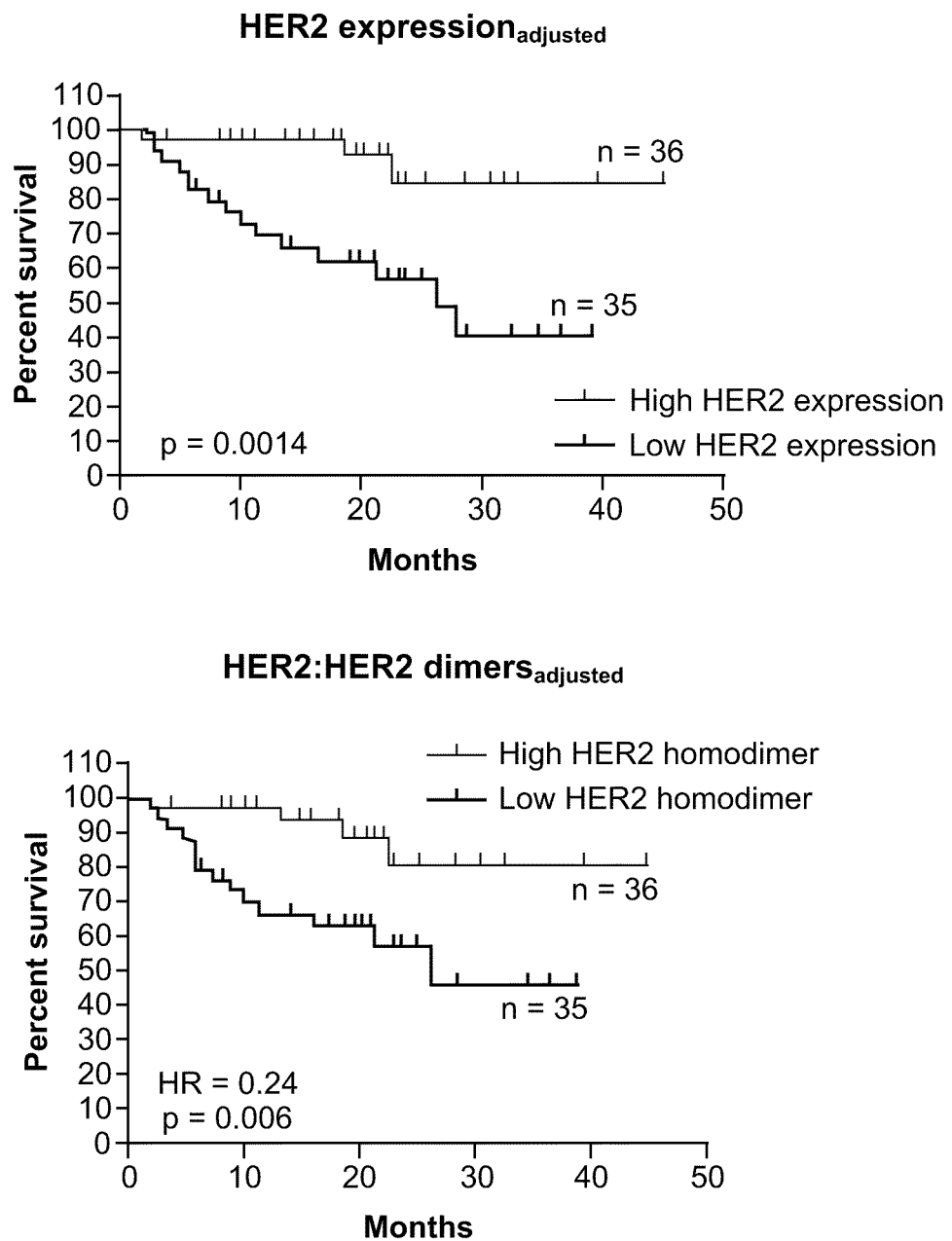
FIG. 8 displays a Kaplan-Meier curve showing the relationship between Her-2 expression or Her-2 homodimers and survival accounting for the impact of other significant variables as defined by the Cox model as set forth in Example 18. Adjusted values for Her-2 expression and Her-2 homodimers are given by the formulas $$\{\log(H2_{adj}) = \log(H2) + (\beta_{mets}/\beta_{H2})[\#mets] + (\beta_{traz\ only}/\beta_{H2})[\text{traz only}]\}$$ and $$\{\log(H22D_{adj}) = \log(H22D) + (\beta_{mets}/\beta_{H22D})[\#mets] + (\beta_{traz\ only}/\beta_{H22D})[\text{traz only}]\}$$

Data generated using 170 FFPE breast tumors demonstrate that the eTag™ assay measures subtle differences in Her-2 expression that are distributed over a 3-log dynamic range compared to the semi-quantitative readout of IHC assessed on a 0-3+ scale (See FIG. 6), or using the more quantitative histoscore (H score), where staining intensity is corrected for percent tumor involvement. Using 19 FFPE breast tumors assessed by FISH at an independent clinical laboratory (PhenoPath Laboratories, Seattle, Wash.), eTag™ measures of Her-2 expression demonstrate a general correlation with total FISH copy number and centromere 17-corrected FISH copy number, however the data suggest that similarly gene-amplified tumors may express significantly different amounts of Her-2 (See FIG. 7).

Example 17: Measurement and Statistical Analysis

Measurements of Her-2 expression and Her-2 homodimers were tested for correlation with overall survival. Deaths not attributed to breast cancer were considered as censored at the time of death. Time to progression was also used as an endpoint. Patients were classified as either high or low for each of the two eTag™-related variables, Her-2 expression and Her-2 homodimers, using the median of the distribution. High and low groups were compared for time-to-event end points using Kaplan-Meier analysis. Cox proportional hazards regression was performed to determine the most significant correlates with outcome. Variables tested included Her-2 expression, Her-2 homodimers, Her-2 gene copy number per chromosome 17, treatment group (trastuzumab-only or trastuzumab plus chemotherapy), estrogen and progesterone receptor status, exposure to adjuvant hormonal therapy or adjuvant chemotherapy, presence of metastases in the liver, lung, skin, bone, lymph nodes, and total number of sites where metastases were found. Metastatic sites occurring in less than 10% of the total cohort were not considered as individual variables, but were included in the calculation of the total number of sites. Continuous variables including Her-2 expression, Her-2 homodimers, and Her-2 gene copy number were tested both as linear variables and in logarithmic form.

Example 18: Quantitation and Analysis of an Adjusted Model

The eTag™ assay was used to quantitate Her-2 expression and Her-2 homodimers in FFPE specimens from the clinical cohort of metastatic breast cancer patients who were treated with a trastuzumab-containing regimen following failure of chemotherapy. Eighty percent of the cohort received treatment in the adjuvant setting and 58% received chemotherapy concomitantly with trastuzumab, while the remainder were treated with trastuzumab alone. Of note, greater than 90% of the patients were selected for inclusion on the basis of FISH positivity. Table 1 provides a description of the clinical features of the cohort. There was mandatory confirmation of Her-2 status as well as centralized collection of clinical data.

TABLE 1

Description of the clinical features of the Bordet cohort.
Characteristics of the clinical cohort

| Characteristic | Jules Bordet cohort |
| --- | --- |
| Geographic origin | Belgium |
| Type of cohort | Expanded access |
| Centralized HER2 assessment | yes |
| Centralized clinical data collection | yes |
| Length of follow-up (months) | 2.6-44.9 |
| Total number of patients | 71 |

| Parameter | Number of patients (%) |
| --- | --- |
| HER2 status by IHC | 7 (9.9) |
| HER 2 status by FISH | 64 (90.1) |
| Hormone receptor status | |
| ER+ PR+ | 11 (15.5) |
| ER+ PR− | 11 (15.5) |
| ER− PR+ | 6 (8.5) |
| ER− PR− | 36 (50.7) |
| ER unknown, PR− | 2 (2.8) |
| ER unknown, PR unknown | 5 (7.1) |
| Nodal status | |
| Negative | 17 (23.9) |
| 1 to 3 positive nodes | 16 (22.5) |
| 4 to 10 positive nodes | 13 (18.3) |
| >=10 positive nodes | 19 (26.8) |
| Status missing | 6 (8.5) |
| Tumor size | |
| $^2$ cm | 24 (33.8) |
| >2 cm & $^2$5 cm | 23 (32.4) |
| >5 cm | 7 (9.9) |
| Missing | 17 (23.9) |

TABLE 1-continued

Description of the clinical features of the Bordet cohort.
Characteristics of the clinical cohort

| Prior adjuvant therapy | |
|---|---|
| Adjuvant hormonal therapy | 29 (40.9) |
| Adjuvant chemotherapy | 47 (66.2) |
| Adjuvant hormonal therapy only | 10 (14.1) |
| Adjuvant chemotherapy only | 28 (39.4) |
| Adjuvant hormonal + adjuvant chemotherapy | 19 (26.8) |
| None | 14 (19.7) |
| Number of metastatic sites | |
| 1 or 2 | 55 (77.5) |
| 3 or 4 | 16 (22.5) |
| Treatment | |
| trastuzumab + chemotherapy | 41 (57.8) |
| trastuzumab only | 30 (42.3) |

| Characteristic | Jules Bordet cohort |
|---|---|
| Geographic origin | Belgium |
| Type of cohort | Expanded access |
| Centralized HER2 assessment | yes |
| Centralized clinical data collection | yes |
| Length of follow-up (months) | 2.6-44.9 |
| Total number of patients | 71 |

| Parameter | Number of patients (%) |
|---|---|
| HER2 status by IHC | 7 (9.9) |
| HER 2 status by FISH | 64 (90.1) |
| Hormone receptor status | |
| ER+ PR+ | 11 (15.5) |
| ER+ PR− | 11 (15.5) |
| ER− PR+ | 6 (8.5) |
| ER− PR− | 36 (50.7) |
| ER unknown, PR− | 2 (2.8) |
| ER unknown, PR unknown | 5 (7.1) |
| Nodal status | |
| Negative | 17 (23.9) |
| 1 to 3 positive nodes | 16 (22.5) |
| 4 to 10 positive nodes | 13 (18.3) |
| >=10 positive nodes | 19 (26.8) |
| Status missing | 6 (8.5) |
| Tumor size | |
| $^2$2 cm | 24 (33.8) |
| >2 cm & $^2$5 cm | 23 (32.4) |
| >5 cm | 7 (9.9) |
| Missing | 17 (23.9) |
| Prior adjuvant therapy | |
| Adjuvant hormonal therapy | 29 (40.9) |
| Adjuvant chemotherapy | 47 (66.2) |
| Adjuvant hormonal therapy only | 10 (14.1) |
| Adjuvant chemotherapy only | 28 (39.4) |
| Adjuvant hormonal + adjuvant chemotherapy | 19 (26.8) |
| None | 14 (19.7) |
| Number of metastatic sites | |
| 1 or 2 | 55 (77.5) |
| 3 or 4 | 16 (22.5) |
| Treatment | |
| trastuzumab + chemotherapy | 41 (57.8) |
| trastuzumab only | 30 (42.3) |

Cox proportional hazards analysis were performed using overall survival and time to progression as endpoints as set forth in Table 2.

TABLE 2

Cox proportional hazards models for OS and TTP.

| Model | Variable | P Value | Hazard Ratio (95% CI) |
|---|---|---|---|
| Cox Proportional Hazards Models: Independent correlates of overall survival HER2 expression | | | |
| A | Number of metastatic sites | 0.00019 | 2.4/site (1.5-3.9) |
| N = 71 | HER2 expression by eTag ™ | 0.0058 | 0.24/log H2* (0.09-0.7) |
| | Trastuzumab-only treatment arm | 0.036 | 2.8 (1.1-7.2) |
| | Likelihood ratio test: model p-value = 0.00009 | | |
| B | Number of metastatic sites | 0.0012 | 3.4/site (1.6-7.1) |
| N = 54 | Trastuzumab-only treatment arm | 0.0452 | 3.8 (1.0-13.8) |
| | Tumor size (N = 54) | 0.0469 | 0.6 (0.4-1.0) |
| | HER2 expression by eTag ™ | 0.1368 | |
| C | Number of metastatic sites | 0.00008 | 3.4/site (1.8-6.2) |
| N = 71* | Trastuzumab-only treatment arm | 0.014 | 3.5 (1.3-9.3) |
| | Tumor size (* missing values assigned mean) | 0.034 | 0.7 (0.5-1.0) |
| | HER2 expression by eTag ™ | 0.005 | |
| *H2 = HER2 expression | | | |
| HER2 homodimers | | | |
| D | Number of metastatic sites | 0.00024 | 2.4/site (1.5-3.8) |
| N = 71 | HER2 homodimer by eTag ™ | 0.016 | 0.42/log H22D* (0.21-0.85) |
| | Trastuzumab-only treatment arm | 0.021 | 3.2 (1.2-8.6) |
| | Likelihood ratio test: model p-value = 0.00018 | | |
| E | Number of metastatic sites | 0.0011 | 2.5 (1.5-4.0) |
| N = 66 | HER2 homodimer by eTag ™ | 0.004 | 0.33/log H22D* (0.16-0.71) |
| | Trastuzumab-only treatment arm | 0.0014 | 7.0 (2.1-23) |
| | Progesterone Receptor positive (N = 66) | 0.0345 | 0.18 (0.04-0.88) |
| *H22D = HER2 homodimer | | | |

TABLE 2-continued

Cox Proportional Hazards Models: Independent correlates of time to progression
HER2 expression

| | | | |
|---|---|---|---|
| F | Number of metastatic sites | 0.0056 | 1.62/site (1.15-2.3) |
| N = 71** | HER2 expression by eTag™ | 0.035 | 0.51/log H2* (0.28-0.95) |
| | Trastuzumab-only treatment arm | 0.0041 | 2.7 (1.4-5.3) |
| | Likelihood ratio test: model p-value = 0.0038 | | |
| G | Lung metastases | 0.0021 | 2.8 (1.4-5.3) |
| N = 71** | Trastuzumab-only treatment arm | 0.02 | 2.1 (1.1-4.0) |
| | HER2 expression by eTag™ | 0.17 | |

*H2 = HER2 expression

HER2 homodimers

| | | | |
|---|---|---|---|
| H | Number of metastatic sites | 0.0098 | 1.57/site (1.1-2.2) |
| N = 71** | HER2 homodimer by eTag™ | 0.047 | 0.62/log H22D* (0.38-0.99) |
| | Trastuzumab-only treatment arm | 0.004 | 2.8 (1.4-5.5) |
| | Likelihood ratio test: model p-value = 0.0048 | | |
| I | Lung metastases | 0.0021 | 2.8 (1.4-5.3) |
| N = 71** | Trastuzumab-only treatment arm | 0.02 | 2.1 (1.1-4.0) |
| | HER2 homodimer by eTag™ | 0.12 | |

*H22D = HER2 homodimer
**21 patients censored early for change in Rx prior to progression The relationship between Her-2 expression and clinical benefit as assessed by RECIST criteria (complete response (CR)+partial response (PR)+stable disease (SD)>6 months) suggest that higher Her-2 expression portends better responses to trastuzumab. Her-2 homodimers appear to correlate with response even better.

Kaplan-Meier (KM) analyses were performed to examine the relationship between the quantitative levels of Her-2 expression or Her-2 homodimers and overall survival. In the absence of data suggesting an optimum cutoff, we defined high as≥the median value of the distribution and low as below the median of the distribution as defined herein.

Example 19: Quantitation and Analysis of Unadjusted and Adjusted Models

As shown in FIG. 9, treatment response appears to differ between patient groups with high Her-2 expression and homodimers and those with low Her-2 expression and homodimers. Those in the high group gained little from the addition of chemotherapy (See FIG. 9) while those in the low group benefited significantly from concomitant chemotherapy and trastuzumab. In the subgroup of patients treated with trastuzumab alone (N=30), patients with high Her-2 expression or homodimers survived longer than those in the low group (HR=0.27, p=0.035 for Her-2 expression, HR=0.29, p=0.049 for Her-2 homodimers).

The left panel of FIG. 9(a) shows univariate analysis of the affect of Her-2 (H2T) levels on survival, before correcting for the confounding influence of other significant variables identified in the Cox model, and likely underestimates the true impact of Her-2 on survival. In FIG. 10, the same plot is shown, now accounting for the confounding variables "number of metastatic sites" and "treatment arm". Correspondingly, the left panel of FIG. 9(b) shows the univariate KM analysis for Her-2 homodimer (H22D), and FIG. 10(b) shows the Cox-adjusted model. The univariate plot for the homodimer approaches statistical significance (p=0.07) even before Cox-adjustments.

In the subgroup of patients treated with trastuzumab alone (N=30), patients with high Her-2 (H2T) or Her-2 homodimer (H22D) survived longer than those in the low group (HR=0.27, p=0.035 for HER2 expression; HR=0.29, p=0.049 for HER2 dimers). This was observed even before Cox adjustment for confounding variables. Although these data are derived from a small sample, they make sense because the relationship between the measurement H2T, the target of the drug, and outcome following treatment with trastuzumab, is not confounded by the concomitant administration of chemotherapy. Therefore, since the survival benefit realized is due solely to trastuzumab, the relationship between H2T or H22D and outcome is more apparent.

In summary, in this cohort of patients that was stringently selected (64/71 selected by FISH with independent review and confirmation of HER2 status) to be HER2 amplified or HER2 over-expressed (7/71 IHC 3+), quantitative measures of HER2 expression or HER2 homodimers, as provided by VeraTag assays, describe a continuum of outcomes following treatment with trastuzumab. Not all FISH+ or IHC 3+ patients have the same probability of response to trastuzumab. The OS and TTP analyses in particular suggest that higher HER2 expression or homodimer levels portend better clinical outcomes than lower levels, following trastuzumab treatment.

Example 20: Results

The data set forth above have several interesting interpretations. First, in a cohort of patients considered to be Her-2 amplified or Her-2 over-expressed on the basis of FISH or IHC respectively (90% selected by FISH, 10% by IHC with mandatory confirmation of Her-2 status and independent review), quantitative measures of Her-2 expression or Her-2 homodimers, as provided by eTag™ describe a continuum of response to trastuzumab. The overall survival and response analyses in particular suggest that higher Her-2 expression or homodimer levels portend better responses and longer survival times than lower levels, following trastuzumab treatment.

Metastatic breast cancers that express very high levels of Her-2 or Her-2 homodimers may be more susceptible to trastuzumab because the signaling cascades that drive their proliferation and survival may be more dependent on associations that are targets of the drug, whereas those tumors that express lower levels of Her-2 or have lower levels of Her-2 homodimers may derive their proliferative potential from a more heterogeneous set of protein complexes, not all of which are specifically antagonized by trastuzumab.

Tumors that are more heterogeneous, from a signaling perspective, may be better equipped to develop resistance to trastuzumab via alternative signaling mechanisms than tumors that are more homogeneously dependent on signaling through protein complexes that are targeted by trastuzumab.

Second, the ability of the eTag™ assay to measure protein dimerization using FFPE specimens is a novel capability, and suggests a way to test the hypothesis that combination therapy regimens selected on the basis of "functional" pathway activation may be more clinically useful than measuring the presence or absence of a particular gene or gene product. In this study, we observed a good correlation between Her-2 expression levels and Her-2 homodimer levels, and that may reflect the biology of Her-2 self-association.

Third, the observation that patients whose tumors express high levels of Her-2 or Her-2 homodimers appear to benefit little from the addition of chemotherapy to trastuzumab while their counterparts in the lower half of the Her-2 distribution appear to benefit significantly from combination therapy is potentially important. While it would be incorrect to conclude that patients in the low eTag™ expression/homodimer group are not benefiting from trastuzumab, the data suggest that not all patients selected for trastuzumab therapy by the best currently available methods have the same probability of response and survival. This is consistent with what is already known about response and survival following trastuzumab therapy in patients with metastatic breast cancer, i.e. not all patients fare equally well on trastuzumab. eTag™ may offer the opportunity to discriminate between groups of patients with different probabilities of clinical response and to begin to make better decisions regarding their management. The knowledge that particular patients have a higher probability of early failure may identify them as better candidates for combination therapy trials than their counterparts who may be unlikely to show demonstrable benefit from the addition of other targeted inhibitors to a trastuzumab-based regimen. In addition, the identification of a subgroup of patients for whom concomitant chemotherapy adds little benefit, and who could be spared an unnecessary risk of toxicity, would be highly desirable.

Example 21: Analysis of Toi Clinical Cohort 75 patients with metastatic breast cancer were drawn from six oncology clinics in Japan and assayed for Her-2 and Her-2 homodimer expression in FFPEs using the eTag™ assay as set forth above. All patients received trastuzumab and at least one chemotherapeutic agent. Median clinical follow-up was 26 months. Cox proportional analysis and Kaplan-Meier analysis were performed as set forth above.

FIG. 12 shows a univariate Kaplan-Meier analysis of the IHC subgroups 0-1+, 2-3+ and 3+ alone. High expression are those groups above the median, and low expression are those groups below the median. In each of the graphs, the x-axis shows percent survival and the y-axis shows overall survival. From the graph, one can see that high Her-2 expression correlates with better overall survival. Table 3 sets forth the clinical characteristics of the cohort.

TABLE 3

Characteristics of the Toi cohort. Summary data

| Characteristic | Toi cohort |
|---|---|
| Geographic origin | Japan |
| Type of cohort | Clinic-based |
| Centralized HER2 assessment | no |
| Centralized clinical data collection | no |
| Length of follow-up (months) | 3.4-63.3 |
| Total Number of patients | 75 |

| Parameter | Number of patients (%) |
|---|---|
| HER2 status by IHC | 75 (100) |
| HER 2 status by FISH | 9 (12.0) |
| Hormone receptor status | |
| ER+ PR+ | 10 (13.3) |
| ER+ PR− | 2 (2.7) |
| ER− PR+ | 3 (4.0) |
| ER− PR− | 60 (80.0) |
| ER unknown, PR− | 0 |
| ER unknown, PR unknown | 0 |
| Nodal status | |
| Negative | 12 (16.0) |
| 1 to 3 positive nodes | 24 (32.0) |
| 4 to 10 positive nodes | 13 (17.3) |
| >=10 positive nodes | 21 (26.0) |
| Status missing | 5 (6.7) |
| Tumor size | |
| <=2 cm | 12 (16.0) |
| >2 cm & <=5 cm | 43 (57.3) |
| >5 cm | 14 (18.7) |
| Missing | 6 (8.0) |
| Prior adjuvant therapy | |
| Adj HT | 33 (44.0) |
| Adj CT | 51 (68.0) |
| Adj HT only | 9 (12.0) |
| Adj CT only | 27 (36.0) |
| Adj HT & Adj CT | 24 (32.0) |
| neither HT nor CT | 15 (20.0) |
| Number of rnet sites | |
| 1 Or 2 | 49 (65.3) |
| 3 or 4 | 25 (33.3) |
| unknown | 1 (1.3) |
| Treatment | |
| Herceptin + chemo | 63 (84.0) |
| Herceptin only | 12 (18.0) |

Cox regression analyses were performed on the subgroup of patients that scored IHC 2+ or 3+ on repeat testing. The models that best fit the observed data are shown above. Her-2 homodimer expression correlated with overall survival better than Her-2 total expression in this dataset. Table 4 shows a Cox proportional hazards regression analysis.

Cox Proportional Hazards Regression Analysis

| Model | Variable | p value | Hazard Ratio |
|---|---|---|---|
| A | Number metastatic sites | 0.015 | 1.7/site |
| | trastuzumab-only treatment | 0.00091 | 19 |
| | HER2:HER2 dimer level/ trastuzumab-only interaction term | 0.025 | 0.17/log HER2:HER2 |

-continued

| Cox Proportional Hazards Regression Analysis | | | |
|---|---|---|---|
| Model | Variable | p value | Hazard Ratio |
| B | Number metastatic sites | 0.019 | 1.7/site |
|  | trastuzumab-only treatment | 0.018 | 4.1 |
|  | HER2:HER2 dimer level | 0.081 | 0.44/log HER2:HER2 |

FIG. 13 shows the Kaplan-Meier analysis of Her-2 homodimer levels and overall survival using the sum of the weighted variables from Cox. As can be seen, adding the impact of the number of metastatic sites in the trastuzumab-only treatment group, higher Her-2 homodimer levels correlate with improved overall survival whether the cutoff is chosen arbitrarily at the median or optimized.

Example 22: Standardized IHC on the Toi Cohort Reveals False Positives in Initial Screening The Toi cohort represented a clinic-based "real world" cohort derived from 6 major cancer centers in Japan that lacked the same stringency for selection of HER2+ patients that characterized the Bordet cohort. Most significantly, they were selected for trastuzumab therapy based on non-standardized IHC tests (88%) performed by different pathologists in different institutions, and there was no confirmation of HER2 status or independent review of the screening IHC data. Almost all patients were treated with trastuzumab+ chemotherapy. The clinical data were pulled from chart reviews. The correlation between H2T and the screening IHC results is shown in FIG. 14a. No difference was observed in the distribution of H2T values in the IHC 2+ group compared with those in the IHC 3+ group. The IHC assays were repeated in a standardized fashion (with a single pathologist) and the results are shown in FIG. 14b. These results showed the same stair-step correlation observed in controlled experiments performed in 170 breast cancer specimens (see FIG. 6a). These data also demonstrated that at each point along the IHC scale (0, 1+, 2+, 3+), there was approximately a 1-log distribution of H2T values, with significant overlap between the groups. Thus, these repeat IHC data strongly suggested that one-third of the Toi cohort was comprised of false positives by the screening IHC.

Example 23: A Comparison of the Bordet Cohort with the Toi Cohort Using Repeated IHC Data A statistical method of examining the hazard associated with a continuous variable, in this case H2T, is referred to as the Martingale residual (FIG. 15). A Martingale residual (MR) with a negative slope denotes a hazard that is dropping continuously as the measured variable increases, whereas a MR with a positive slope denotes a hazard that is rising continuously as the measured variable increases. As shown in FIG. 15a, the MR observed in the Bordet cohort (dashed line) had a negative slope, while the MR derived from the Toi cohort tracked with the Bordet cohort above a certain H2T value, but at low H2T values, the hazard was opposite to that observed in the Bordet cohort. In other words, at higher levels of H2T, Toi appears to behave similarly to the Bordet cohort. However, at low levels of H2T, Toi does not behave at all like the Bordet cohort. When examining those patients who tested 0 or 1+ on repeat IHC testing (closed circles, as shown in FIG. 15b), an interesting pattern emerges. Nearly all of those patients that were "false positives" on repeat IHC testing lie on the left side of the graph, and are largely responsible for the "discordance" observed when comparing the MRs of the Bordet and Toi cohorts. Nearly all the patients that lie on the right side of the graph, where there is great similarity between the MRs of Bordet and Toi, tested 2+ or 3+ on repeat IHC testing, and exhibit a similar relationship to that observed in Bordet: higher H2T correlates with decreasing hazard for death. Using this type of analysis, cutoffs were established (dashed vertical line in FIG. 15b), in which most of the IHC 0 and 1+ samples were on the left of the line and the slope of the MR was positive (i.e., lower H2T correlates with increasing hazard for death) and in which most of the IHC 2+, 3+ samples were on the right side of the line and the slope of the MR was negative (i.e., higher H2T correlates with decreasing hazard for death).

Example 24: Analysis of the Toi Cohort Using Repeated IHC Data

KM analyses of subgroups within the Toi cohort demonstrate that those patients with higher H2T and who tested 2+ or 3+ on repeat IHC testing did indeed exhibit a similar correlation between H2T and OS as was observed in the Bordet cohort, while those patients in the lower range of H2T (IHC 0 or 1+ on repeat testing) showed the opposite relationship (FIG. 16). Indeed, Cox proportional hazards analyses of the higher H2T subgroup (those patients above the cutoff [dashed line] in FIG. 15b) yielded a model similar to that derived from the Bordet cohort. Here, instead of H2T, H22D appeared most closely correlated with OS. As a single variable, the relationship lacked statistical significance (p=0.081), but the interaction term containing both H22D and trastuzumab-only treatment arm reached statistical significance (p=0.025) (Table 6), consistent with the observation seen in FIGS. 10 and 11.

The best H2T cutoff (the vertical dashed line in FIG. 15b) is defined as the cutoff that discriminates best between the group including IHC0 and 1+ samples (group IHC−), and the group including IHC2+ and 3+ samples (group IHC+). Multiple candidate cutoffs were tested. The fisher exact test was used to test the significance between the number of IHC-samples and IHC+ above and below each candidate cutoff. The discrimination was very high when the comparison encompasses all the samples of the dataset, precluding the identification of the lowest p-value (most p-values <0.0001). We restricted the comparison within a window of 15 samples above and below the candidate cutoff. The best cutoff was found equal to Log 10-H2T=1.60.

Multivariate Cox proportional hazards models were generated using all available variables defined before trastuzumab treatment. These included those variables listed in Table 5 (below).

TABLE 5

Variables examined that were defined prior to trastuzumab treatment.

| variable name | description |
|---|---|
| H2T | log10 of total HER2 |
| H2D | log10 of HER2 homodimer |
| H2DbyH2T | log10 of the ratio of H2D/H2T |
| H2Tcut | H2T above or below cutoff |
| IHC | IHC score |
| Age | Age in years |
| noMetSites | Number of organs containing detectable metastases |
| Metcat | noMetSites ≥3 or <3 |
| ER | Estrogen receptor: negative, weak, medium or strong |
| ERcat | ER negative or positive (weak, medium or strong) |

TABLE 5-continued

Variables examined that were defined prior to trastuzumab treatment.

| variable name | description |
|---|---|
| PgR | Progesterone receptor: negative, weak, medium or strong |
| PgRcat | PgR negative or positive (weak, medium or strong) |
| H2TER | Interaction between H2Tcut an ERcat |
| Line | Line where trastuzumab was first included |
| Honly | Treatment with Herceptin-only vs. Herceptin + chemotherapy |
| setting | Metastatic vs. adjuvant setting |
| CNS | Central nervous system containing vs. absent metastases |
| Bone | Bone containing vs. absent metastases |
| Liver | Liver containing vs. absent metastases |
| Lung | Lung containing vs. absent metastases |
| Lym | Lymph nodes containing vs. absent metastases |
| Skin | Skin containing vs. absent metastases |
| Other | Metastases found in organs other than those listed above |
| p53 | Presence of p53 |
| PrimaryToMet | Time between primary tumor and detection of metastatic disease |
| SampleToTx | Time between acquisition of tumor and trastuzumab-containing treatment |
| TxLength | Duration of trastuzumab-containing treatment |
| 15.3 | Presence of 15.3 |
| CEA | Presence of CEA |

Models containing 1 to 5 variables in which all the variables had p<0.05 were considered. The best model was identified as that with the lowest p-value.

TABLE 6

Multivariate Cox proportional hazards analysis of the subgroup of patients from Toi who have H2T values >1.6 (cutoff = dotted vertical line in FIG. 7b), the "true positives", yields a model that approximates that derived from Bordet.
Cox Proportional Hazards Regression Analysis

| Model | Variable | p value | Hazard Ratio |
|---|---|---|---|
| A | Number metastatic sites | 0.015 | 1.7/site |
|  | trastuzumab-only treatment | 0.00091 | 19 |
|  | HER2:HER2 dimer level/ trastuzumab-only interaction term | 0.025 | 0.17/log HER2:HER2 |
| B | Number metastatic sites | 0.019 | 1.7/site |
|  | trastuzumab-only treatment | 0.018 | 4.1 |
|  | HER2:HER2 dimer level | 0.081 | 0.44/log HER2:HER2 |

These analyses suggested that the same relationship between H2T and OS that was evidenced in the Bordet cohort was also present in the Toi cohort. The presence of a "contaminating" false positive population in the Toi cohort was not surprising given the nature of the selection criteria used in this cohort (clinic-based population, IHC performed by ≥6 separate pathologists) compared to the stringent nature of the selection criteria applied to the Bordet cohort (>90% FISH+, confirmed and independently reviewed by a committee of pathologists).

Example 25: Description and Use of VeraTag™ on the Lipton Cohort of Patients with MBC The VeraTag™ assay was performed in a third independent cohort of patients with MBC. This cohort (N=92) was derived from the International Serum Her2/neu Study Group (ISHSG) (abstract accepted for poster presentation, SABCS in December 2007) and is called the Lipton cohort. Although, like the Toi cohort, these patients were selected primarily by IHC, the IHC was performed at a central location—the University of Vienna in Austria—by a single pathologist. 90% of patients were IHC 3+, and 80/92 received trastuzumab in combination with chemotherapy, while 12 received trastuzumab as a single drug. 88/92 patients had MBC, and they could have received trastuzumab either as first, second, or third line therapy.

As shown in FIG. 17, patients that were assessed as over-expressing HER2 by IHC at 3+ intensity demonstrated a broad range of H2T values as measured by VeraTag™ assay. Further, the patients who were called IHC 2+ shared an overlapping distribution of H2T values with those that were called 3+. The relationship between H2T by VeraTag™ and ER/PR positivity was also examined. Here, the reciprocal relationship that has been described in the literature previously (JNCI-2003. 95(2):142) was observed (see FIG. 18).

Example 26: Results for the Lipton Cohort of Patients with MBC

As was found in analyses of the Bordet cohort (FIG. 19), those patients in the Lipton cohort with H2T values experienced higher objective response rates than those with lower H2T values (FIG. 20).

Univariate Kaplan-Meier analyses demonstrated that those patients in the Lipton cohort with H2T or H22D values above the median of the distribution experienced statistically significantly longer TTP than those patients with H2T or H22D values in the lower half of the distribution (FIG. 21 a-b). For H2T, the median TTP for the high H2T group was 13-months, while the median TTP for the lower group was 4-months (p=0.0003). Since there is no data to suggest an optimum response cutoff, the median was arbitrarily selected. Using OS as the endpoint, the univariate KM analyses showed a trend in favor of the high group (>median, p=0.1), but no significant relationship was observed for H22D (FIG. 21c-d).

Example 27: Multivariate Cox Hazard Model Confirms H2T Correlated with TTP and OS Multivariate Cox proportional hazards models using all the patients in the cohort, and testing all possible combinations of all available variables, revealed that the best model contained three independently significant correlates of TTP: #metastatic sites, line of therapy, and log.sub.10H2T by VeraTag™ assay (Table 7). This model is remarkably similar to what had been observed previously, as the hazard ratio for H2T was 0.46 per 1-log increase in H2T. These data once again suggest a continuous relationship between H2T and outcome, this time TTP, such that higher HER2 expression as measured by VeraTag™ assay portends a better clinical outcome on trastuzumab.

TABLE 7

Multivariate Cox proportional hazards model that best explains the observed TTP outcomes. This model utilizes all patients from Lipton.
Best Multivariate Cox Model for TTP

| Variable | Hazard Ratio | p-value |
|---|---|---|
| # metastatic sites | 1.31 | 0.0003 |
| $\log_{10}H2T_{VeraTag™}$ | 0.46 | 0.0028 |
| Line of therapy | 1.73 | 0.0054 |

Model p-value = 2.8E−6

Examination of the Martingale residual for the Lipton cohort revealed a biphasic curve, similar to what was observed in the Toi cohort (FIG. 22). At higher H2T values, the MR slope is negative indicating a decreasing hazard as H2T increases, like the Bordet cohort. However, at lower levels of H2T, we once again see the hazard behaving oppositely, with a positive slope as H2T increases. Since Cox models are incapable of fitting to non-linear data distributions, the data was transformed using second order polynomials. This allows the Cox model to fit non-linear data. When that is done, the model that best fits the observed data is shown in Table 8. This model is consistent with other Cox models derived previously, once again suggesting a reduction in risk of death with increasing H2T level.

TABLE 8

Multivariate Cox proportional hazards model that best explains the observed OS outcomes. This model utilizes all patients from Lipton, and transforms the data into a second order polynomial so that the Cox model can be fit to a non-linear distribution (first order Cox models are incapable of fitting non-linear data distributions).
Best Multivariate Cox Model for OS

| Variable | Hazard Ratio | p-value |
| --- | --- | --- |
| # metastatic sites | 1.74 | 1.00E−08 |
| $\log_{10}H2T_{VeraTag^{TM}}$ | 0.16 | 0.0021 |
| Line of Therapy | 0.52 | 0.0004 |

Model p-value = 1.1E−7

Example 28: Analysis of the Lipton Cohort Using the Cutoff Established with Toi Cohort Data An alternative approach to analyzing the Lipton cohort is to apply the cutoff derived from the Toi cohort (vertical dotted line from FIG. 15b) to the Lipton cohort following normalization of H2T signals using shared controls, and exclude those patients that fall in the low H2T range below the cutoff—the "false positives." When this is done and Cox models are derived using only those patients with H2T values above the Toi cutoff, the best model is shown in Table 9. This method yields almost exactly the same results as the previous statistical approach, with a hazard ratio of 0.15 per 1-log increase in H2T and the same three variables.

TABLE 9

Multivariate Cox proportional hazards model that best explains the observed OS outcomes following exclusion of the "false positives" as defined by the cutoff derived from Toi.
Best Multivariate Cox Model for OS (imposing H2T cutoff from Toi)

| Variable | Hazard Ratio | p-value |
| --- | --- | --- |
| # metastatic sites | 1.76 | 3.00E−07 |
| $\log_{10}H2T_{VeraTag^{TM}}$ | 0.15 | 0.0006 |
| $Age_{hi/low}$ | 0.54 | 0.0022 |

Taken together, data from these 3 metastatic breast cancer cohorts suggest that within a population of patients selected by IHC and/or FISH to receive trastuzumab treatment, not all the patients have the same probability of response. In those patients who were truly over-expressing HER2, higher HER2 expression (H2T) by VeraTag™ assay correlated with better response rates, longer overall survival (OS) and longer time-to-progression (TTP). Furthermore, in the two cohorts selected by IHC (Toi and Lipton), those patients with the lowest H2T levels appeared to behave differently than the "true over-expressers" (true positives). For those patients, the directionality of the relationship between H2T and outcome appeared to be opposite of the true positives. While these relationships require confirmation in larger well-controlled studies, the data are consistent in two separate cohorts, and suggest that for those patients in the low H2T range below the cutoff, something other than HER2 may be driving outcome. The existence of a reciprocal relationship between the HER signaling pathways and other pathways not targeted by trastuzumab (e.g., ER signaling), suggests at least one testable hypothesis. Moreover, given the extremely stringent nature of the selection criteria applied in the Bordet cohort, Toi and Lipton, with their "contaminating" false positive subpopulations, may be more reflective of the reality of clinical practice. If true, these data suggest that validation of a lower cutoff by VeraTag™ assay offers an opportunity to sharply reduce the overall false positive rate for trastuzumab treatment, and shunt those patients toward potentially more effective regimens.

Finally, as seen in Bordet, patients with high HER2 expression appeared to derive little additional benefit from concomitant chemotherapy (CT), while patients with low HER2 expression benefited significantly from the addition of CT to trastuzumab. These data suggest alternative treatment strategies that could be enormously advantageous for patients who are unable to tolerate the toxicity associated with concomitant chemotherapy.

Example 29: Description of the ISHSG Cohort

Another cohort of patients from the ISHSG (International Serum HER2/neu Study Group), who were selected primarily by IHC that was centrally performed at the University of Vienna, were tested with the VeraTag™ assay (n-106). Specifically, 98/106 were IHC 3+ and 8/106 were IHC 2+, FISH+. All but 9 of these patients were initially treated in the adjuvant setting (no trastuzumab) and subsequently failed with metastases, at which point they received trastuzumab in the 1st, 2nd, or 3rd line of treatment, almost all in combination with chemotherapy. H2T and H22D in the original tumor specimens were measured and correlated with ORR, TTP, and OS. In addition, the amount of time that had passed between the initiation of adjuvant therapy and the time to first metastasis was known, prior to any treatment with trastuzumab. Therefore, the correlation between our VeraTag™ measurements and the time from primary to met, or PTM was also examined. A schematic diagram of the time course and treatment for patients in the ISHSG cohort is shown in FIG. 23.

Example 30: ER Status Effects Correlation of HRT Level with Response

Higher levels of H2T correlated with higher levels of response (FIG. 24) in the ISHSG cohort. A similar relationship was found for H22D. Of particular interest was the finding that the relationship between the measurement H2T and response was very highly correlated in those patients who were ER negative, but not highly correlated in those who were ER positive.

Example 31: Higher H2T Correlates with Longer TTP, Particularly in ER Negative Patients Univariate Kaplan-Meier (KM) analyses using the median of the H2T distribution as a cutoff or an optimized H2T cutoff showed longer TTP with higher H2T (FIG. 25). To define an optimized cutoff for H2T, Kaplan-Meier survival curves were generated by comparing groups above and below the candidate cutoff. The "optimal" cutoff was defined as that associated with the smallest p-value.

To relate values for H2T or H22D to physical measurements, they are evaluated in standard, well-characterized cell lines, which are used to create a relative scale. For example, the following relative units were obtained for H2T and H22D in three cell lines, MCF7, MDA-MB-453, and SKBR3, each of which has been extensively characterized in the literature.

MCF7: H2T=12, H22D=1.7
MDA-MB-453: H2T=110, H22D=17
SKBR3: H2T=410, H22D=190

Example 32: Higher H2T Correlates with Longer OS, Particularly in ER Negative Patients When the same analysis was performed using OS as the endpoint, the plots shown in FIG. 26 were generated. Using the optimal cutoff, a statistically significant relationship for overall survival in the ER negative sub-population was observed, even before adjusting for multivariate effects.

Example 33: A High H22D Subpopulation of High H2T Expressors Show Interesting Pattern in KM Plots Once an "optimal cutoff" had been identified, analyses were restricted to those patients with H2T values above the cutoff—the best responders—to determine if further subpopulations of patients that behaved in a distinct manner could be identified. Using this approach, another sub-group in the upper range of the H2T distribution was identified. These patients were best discriminated by H22D rather than H2T. As shown below in FIG. 27a, there appear to be two different types of patients that express high levels of H2T—those who express a low level of H22D (group B in FIG. 27a), and those that express higher levels of H22D (group C in FIG. 27a). They appear to perform differently over time. As shown in FIG. 27c, these "high H2T, high H22D/H2T" patients have the best initial response rates. However, over time they appear to undergo a transition and ultimately have the worst OS of the three groups identified. What is even more interesting is that they appear to fare just as well as the "high H2T, low H2D" group until about 30 months, when they appear to progress at a more rapid rate than their counterparts. As shown in FIGS. 27b and 27d, this subgroup with high H2T with apparent time-dependent hazards can be identified as either high H22D/H2T or high H22D alone.

A similar analysis was performed using H22D (dimer) to discern sub-populations of the high H2T group. Similar results were obtained, as seen in FIG. 28. To define an optimized cutoff for H2T and H22D, Kaplan-Meier survival curves were generated by comparing groups above and below the candidate cutoff. The "optimal" cutoff was defined as that associated with the smallest p-value.

Example 34: Multivariate Analyses Identify H2T as a Significant Correlate of Longevity (TTP and OS)

Multivariate Cox proportional hazards analyses performed on the entire Lipton cohort yielded several models that explained the observed data. Best subset models were considered with all combinations of up to 5 variables using all available pre-treatment clinical data. Some variables including number of organs with detectable metastases (noMetSites), Age, ER, PgR, H2T and H22D were also included in the variable sets as categorical variables. All of the models contained some version of the VeraTag™ variables, H2T or H22D. Many models identified the continuous variable H2T as a significant correlate of TTP and OS, however the best models (as defined by the lowest model p-values) for TTP and OS contained H2T as a categorical variable, using the identified optimal cutoff as the discriminator (see Table 10).

TABLE 10

Multivariate Cox models in the ISHSG cohort.
Cox Proportional Hazards Models
ISHSG

| Best overall model for TTP | | Best overall model for OS | |
|---|---|---|---|
| | HR | p | | HR | p |
| Age | 0.98 | 0.037 | Age | 0.967 | 0.003 |
| Skin | 2.23 | 0.004 | noMetSites | 1.645 | 1.6e–08 |
| H2Tcutoff | 0.41 | 0.0002 | ERcat | 0.421 | 0.007 |
| Metcat | 3.31 | 2.3e–07 | H2Tcutoff | 0.446 | 0.009 |
| p = 1.69e–08 n = 105 (1 missing) | | | p = 3.28e08 n103 (3 missing) | | |

H2T cutoff = H2T categorical*
Metcat = No. met sites categorical
noMetSites = No. Met sites continuous
ERcat = Er+ or ER–
*other models contain H2T as a continuous variable Finally, for the 97 patients for whom the time from primary diagnosis to the development of metastases was known, the VeraTag™ variables with the time from primary to met (PTM) were examined. As this occurred in the absence of trastuzumab, this provided an estimate of the prognostic value of the measurements. Conclusions drawn from PTM in this cohort only consider the subset of those patients with primary breast cancer that actually progressed. As shown in Table 11, univariate Cox analyses demonstrated that the H22D/H2T ratio and H22D were significantly correlated with PTM, but the relationship was opposite to what was observed when TTP on trastuzumab was examined. Here, higher levels of H22D/H2T or H22D correlated with shorter PTM. Multivariate analyses failed to identify more than one significant variable. Of note, this relationship was evident only in the ER positive sub-population.

TABLE 11

Correlation of VeraTag ™ measures with PTM (adjuvant setting, no trastuzumab)

| | Variable | HR | p-value |
|---|---|---|---|
| All patients (N = 97) | H2D/H2T | 9.04 | 0.028 |
| | H2D | 1.38 | 0.025 |
| | H2T | 1.40 | 0.11 |
| | IHC | 1.42 | 0.36 |
| ER – (N = 62) | H2D/H2T | 1.72 | 0.25 |
| | H2D | 1.23 | 0.23 |
| | H2T | 1.56 | 0.31 |
| | IHC | 1.93 | 0.31 |
| ER + (N = 35) | H2D/H2T | 3.25 | 0.034 |
| | H2D | 1.23 | 0.064 |
| | H2T | 1.36 | 0.33 |
| | IHC | 1.55 | 1.55 |

Example 35: Prognostic Value of HERMark Measurements in Disease Free Survival Total HER2 protein expression (H2T) and HER2 homodimer levels (H2D) were measured using the HERMark assay in a cohort of breast cancer patients treated with trastuzumab (FIG. 29). All patients were given trastuzumab based on HER2 IHC 3+ or HER2-FISH-positive measurements made on FFPE sections from the primary tumor. At a later date, FISH measurements were made for all patients at a central laboratory. Total HER2 expression and HER2 homodimer levels were measured on additional FFPE sections from the same tumor. The results are shown in FIG. 29A. Both H2T and H2D correlated somewhat with FISH positivity. The proportion of HER2 in homodimer form (H2D/H2T) also trended higher for FISH-positive patients than FISH-negative patients. A plot of H2D/H2T versus continuous FISH/CEP17 (HER2 gene copies per chromosome 17) shows a positive correlation ($R^2$=0.40).

For the patients described in FIG. 29, the time between surgery to remove the primary tumor and the time when metastatic disease was detected was known (disease free survival=DFS). This was prior to the time when trastuzumab was given, as illustrated in the upper panel of FIG. 35. In the absence of trastuzumab, DFS was not significantly different between the tertiles of H2T (FIG. 29B; trend p=0.2). However, tertiles of H2D or H2D/H2T showed a significant difference in DFS (trend p=0.048, 0.026, respectively) with the lowest H2D or lowest H2D/H2T tertiles showing longest DFS. When considered as continuous variables (FIG. 35), log(H2T) trends towards a prediction of worse outcome with higher H2T (HR=1.4/log(H2T); p=0.09), but log(H2D) and H2D/H2T are significant predictors of outcome with higher values correlating with worse outcome (p=0.02 and 0.03, respectively). This would be consistent with the idea that a measure of dimer levels or a proportion of HER2 involved in dimers, measures more indicative of actively signaling receptor, could be more accurate at predicting disease recurrence than the measurement of total HER2.

Example 36: Correlations of Phospho-HER2 with Other HERMark Measures

Eighteen tumors were purchased from Asterand as freshly frozen samples. All tumors were fixed with formalin, embedded in paraffin and sectioned for mounting on slides. Measurements for H2T, H2D and phosphor-HER2 (H2P) were measured using VeraTag™ assays. Significant correlations of H2P with H2T, H2D and H2D/H2T were found for this cohort (FIG. 29C). The strongest correlation with H2P was found for H2D/H2T with an $R^2$ of 0.55.

Example 37: H2T and H2D are Stronger than FISH at Prediction of Outcome on Trastuzumab For the same set of patients considered in Example 35, HERMark measures and HER2 FISH were considered for their ability to predict outcomes in the metastatic setting while patients were on trastuzumab. Cutoffs for H2T and H2D were derived as shown in FIG. 34 by testing all possible cutoffs. The optimal cutoff was deemed to be the one with the lowest p-value shown near the point log(H2T) ~1.2. For these analyses Cox proportional hazards analysis was employed as shown in FIG. 30. For time to progression (TTP) a model containing FISH showed FISH to be significant with a p-value of 0.02. However, when either H2T or H2D was included in this same model, FISH was found to no longer be a significant variable (p=0.8 in both cases). H2T was found to be significant (p=0.018) and H2D was trending predictive (p=0.092). Similar results were found for the overall survival (OS) endpoint, except that H2D was found to be significantly predictive of outcome (p=0.026). These results indicate that when compared directly, either H2T or H2D are stronger predictors of outcome for the patients in this cohort.

In the lower half of FIG. 30, Cox analysis was repeated for those patients categorized as FISH-positive (n=77). For this subset presumed to show the best outcomes using conventional HER2 testing methods (i.e. FISH-positive), it is still possible to subdivide these patients into better and worse TTP and OS using H2T (p=0.0015 and p=0.02, respectively).

In the case of univariate correlations with outcome, H2T and H2D are similarly stronger predictors than FISH. FIG. 31 shows the significant difference in patients above and below the H2T cutoff (HR=0.48; p<0.001). FIG. 32 shows a direct comparison of the H2T and FISH cutoffs and their ability to predict outcome on trastuzumab. The plot at the top left of FIG. 32 highlights three groups that are defined by the FISH and H2T cutoffs. For two of these groups labeled as concordant, H2T-low/FISH-negative and H2T-high/FISH-positive both assays agree in that they predict worse and better outcomes, respectively. However, for the discordant group, H2T-low/FISH-positive, the HERMark assay would predict an outcome similar to the H2T-low/FISH-negative group, while the FISH measurement would predict an outcome similar to H2T-high/FISH-positive group. As shown in the 2-panels on the right of FIG. 32, for both TTP and OS it is the H2T result rather than FISH that accurately predicts outcome for this discordant group of H2T-low/FISH-positive subgroup (b similar c). The lower left panel of FIG. 32 shows that these results cannot be explained by a number of patients in the discordant group falling very close to the FISH cutoff. The H2T-low/FISH-positive subgroup showed a similar range and median of FISH scores to the H2T-high/FISH-positive subgroup. These results are consistent with the idea that in tumors largely driven by HER2 receptor activity the highly quantitative measure of HER2 receptor content (H2T) is more predictive than a measure of gene copy number (FISH), which strongly influences but is does not have a one-to-one relationship with HER2 protein levels. A similar result for H2D is shown in FIG. 33.

Example 38: Use of HERMark Assays in FIN HER

FIN HER was a clinical trial containing arms designed to test the use of 9 weeks of trastuzumab with chemotherapy versus chemotherapy alone in the adjuvant setting for HER2+ breast cancer, as illustrated in FIG. 36. Inclusion into the trastuzumab randomization arms was determined by a combination of standard IHC and CISH (Chromogenic In Situ Hybridization) as shown in FIG. 37. FFPE tumor slides from the FIN HER study were obtained and assayed for H2T and H2D using the HERMark assay.

A comparison of IHC, CISH and HERMark measures is shown in FIG. 38. The cutoff derived in FIG. 34 is shown as a horizontal line in FIG. 38. The value becomes log(H2T) =1.14 from the previously mentioned log(H2T)~1.2 only due to a change in scale from the previous R&D scaling system to the current commercial scaling system. In general, this clinical cutoff is based on outcomes of patients discussed in Example 37 and is generally well correlated with the HER2 status based on IHC and CISH. As patients were subdivided more stringently, organized from left to right in FIG. 38, the cutoff log(H2T)=1.14 appears to be increasingly concordant in the order of local IHC<central IHC<Central CISH<both Central IHC and Central CISH. This last comparison shows the best concordance with the H2T cutoff and the most stringent subgrouping using currently available technology: those that are both central IHC and CISH negative versus those that are both central IHC and CISH positive.

Example 39: Use of HERMark Measures to Stratify HER2-CISH Positive Patients in FIN HER Slides from approximately 200 of the 232 CISH-positive patients randomized into the chemo+/−trastuzumab arms were available for HERMark measurements. Within this group, H2T, H2D and H2D/H2T were first tested as independent correlates responsiveness to trastuzumab as measured by time to distant recurrence (TDR), time to any recurrence (TAR) and time to death (TD). Neither H2T nor H2D were found to be independent correlates of outcomes (FIG. 39). However increasing H2D/H2T was found to be an independent correlate of TAR with marginal significance (p=0.05) and trending towards significance in TDR (p=0.07).

Each variable H2T, H2D and H2D/H2T was next tested for the ability to identify a subgroup with enhanced or reduced benefit from the addition of trastuzumab to chemotherapy using STEPP analysis. Hazard ratios between trastuzumab+chemotherapy versus chemotherapy alone were assessed for bin sizes of 80 patients, scanning from the lowest to highest 80 for each variable of interest. FIGS. 40-42 show the results of these calculations with the hazard ratio for each bin plotted versus the mean value for each variable within the bin. Within this CISH+ cohort, there may be a subset with very high H2T that show a reduced benefit from trastuzumab (FIG. 40). Additionally, there may be a subset with H2D/H2T~0.5 that show a reduced benefit from trastuzumab.

In FIG. 43, the STEPP plot for H2D/H2T from FIG. 42, now with the y-axis on a linear scale, is compared against a gene found on 8q shown to have a significant interaction with trastuzumab treatment in the NSABP B-31 trial. As shown from the right panel of FIG. 43, the dotted line curve fit moves from a hazard ratio of 1 (no benefit) for low expression to a hazard ratio of 0.4 (trastuzumab benefit) with high expression. The comparison suggests that the H2D/H2T may be useful in identifying patients with lesser and greater benefit from the addition of trastuzumab to chemotherapy. Further, those with reduced benefit may be candidates for additional therapies.

What is claimed is:

1. A method of quantitating an amount of HER-2 protein in a sample of a cancer from a subject, the method comprising:
   (a) measuring the amount of HER-2 protein in a sample of cancer from a subject, wherein the sample is deposited on a solid support, wherein the sample on the solid support comprises viable tumor tissue, necrotic tumor tissue and non-tumor tissue, and wherein the measuring is performed using an immunoassay comprising the steps of:
      (i) contacting the sample with a first antibody that binds specifically to HER-2 and comprises a molecular tag attached thereto via a cleavable linkage,
      (ii) cleaving the cleavable linkage thereby releasing the molecular tag in a buffer volume, and
      (iii) quantifying the amount of released molecular tag in the buffer volume;
   (b) after step (a), performing immunohistochemistry staining on the sample to distinguish viable tissue from non-viable tissue;
   (c) defining a total tumor surface area on the sample on the solid support based on imaging of the immunohistochemistry staining of step (b), wherein the total tumor surface area includes all areas of viable tumor and excludes necrotic tissue and non-tumor tissue in the sample on the solid support;
   (d) quantifying the size of the total tumor surface area; and
   (e) determining the amount of HER-2 protein in the sample based on the amount of released molecular tag in the buffer volume normalized to the size of the total tumor surface area.

2. The method of claim 1, wherein the amount of HER-2 protein is total HER-2 or HER-2 homodimer.

3. The method of claim 1, wherein the cancer from the subject is a HER-2 positive cancer.

4. The method of claim 1, wherein the cancer from the subject is breast cancer.

5. The method of claim 1, wherein the solid support is a histology slide.

6. The method of claim 1, wherein the sample is histologically stained before defining the total tumor surface area.

7. The method of claim 1, wherein the total tumor surface area of interest is defined by a pathologist.

8. The method of claim 1, wherein the size of the total tumor surface area is quantified using software.

9. The method of claim 1, wherein the released molecular tag is analyzed by electrophoretic separation to generate an electropherogram.

10. The method of claim 9, wherein an internal reference control molecule having a known concentration is co-analyzed with the released molecular tag by electrophoretic separation.

11. The method of claim 10, wherein the released molecular tag and the internal reference control molecule are quantified by measuring relative fluorescence units (RFU) of an electropherogram peak area of the released molecular tag and RFU of an electropherogram peak area of the internal reference control molecule, and wherein a relative peak area (RPA) representing the amount of the released molecular tag is calculated as a ratio of the RFU of the electropherogram peak area of the released molecular tag to the RFU of the electropherogram peak area of the internal reference control molecule.

12. The method of claim 1, wherein cleaving the cleavable linkage comprises contacting the sample with a second antibody that binds specifically to HER-2 and comprises a cleaving agent attached thereto.

13. The method of claim 12, wherein the first antibody and the second antibody are each specific for a first epitope of HER-2 when quantitating the amount of HER-2 homodimer in the sample.

14. The method of claim 12, wherein the first antibody binds a first epitope of HER-2 and the second antibody binds a second epitope of HER-2 when quantitating the total amount of HER-2 protein in the sample.

15. The method of claim 12, wherein the cleaving agent produces an active species that cleaves the cleavable linkage.

16. The method of claim 15, wherein the cleaving agent has an effective proximity that is the distance within which the cleaving agent can effectively cleave the cleavable linkage.

17. The method of claim 15, wherein at least one of the first antibody and the second antibody comprise a sensitizer attached thereto, wherein the sensitizer induces the cleaving agent to produce the active species.

18. The method of claim 1, wherein the method quantitates the amount of HER-2 in the sample over a dynamic range greater than 2 logs.

19. The method of claim 1, wherein the step of quantifying the size of the total tumor surface area comprises: (i) scanning the total tumor surface area, (ii) obtaining the total pixels of the total tumor surface area scanned area, and (iii) converting the total pixels into the size of the total tumor surface area.

20. The method of claim 1, wherein the step of determining the amount of HER-2 protein is based on the amount of released molecular tag multiplied by the buffer volume and divided by the total tumor surface area, wherein the calculated amount of HER-2 protein is expressed in pmol per mm2.

21. The method of claim 1, wherein the immunohistochemistry staining in step (b) is an hematoxylin and eosin (H&E) staining.

\* \* \* \* \*